US009540642B2

(12) United States Patent
Inberg et al.

(10) Patent No.: US 9,540,642 B2
(45) Date of Patent: Jan. 10, 2017

(54) COMPOSITIONS AND METHODS FOR CONTROLLING ARTHROPOD PARASITE AND PEST INFESTATIONS

(71) Applicants: Monsanto Technology LLC, St. Louis, MO (US); Beeologics, Inc., St. Louis, MO (US); The United States of America, as represented by the Secretary of Agriculture, Washington, DC (US)

(72) Inventors: Alex Inberg, Ballwin, MO (US); Mahak Kapoor, Chesterfield, MO (US); Jay Evans, Harwood, MD (US)

(73) Assignees: The United States of America, as represented by the Secretary of Agriculture, Washington, DC (US); Beeologics, Inc., St. Louis, MO (US); Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/532,596

(22) Filed: Nov. 4, 2014

(65) Prior Publication Data

US 2015/0159156 A1 Jun. 11, 2015

Related U.S. Application Data

(60) Provisional application No. 61/899,772, filed on Nov. 4, 2013.

(51) Int. Cl.

| | |
|---|---|
| ***C12N 15/113*** | (2010.01) |
| ***A01K 51/00*** | (2006.01) |
| ***A61K 31/713*** | (2006.01) |
| ***A01N 37/46*** | (2006.01) |
| ***A01N 63/02*** | (2006.01) |

(52) U.S. Cl.

CPC ............. *C12N 15/113* (2013.01); *A01K 51/00* (2013.01); *A01N 37/46* (2013.01); *A01N 63/02* (2013.01); *A61K 31/713* (2013.01); *C12N 2310/14* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,469,863 | A | 9/1984 | Ts'o et al. |
| 4,476,301 | A | 10/1984 | Imbach et al. |
| 4,535,060 | A | 8/1985 | Comai |
| 4,581,847 | A | 4/1986 | Hibberd et al. |
| 4,666,828 | A | 5/1987 | Gusella |
| 4,683,202 | A | 7/1987 | Mullis |
| 4,761,373 | A | 8/1988 | Anderson et al. |
| 4,769,061 | A | 9/1988 | Comai |
| 4,801,531 | A | 1/1989 | Frossard |
| 4,810,648 | A | 3/1989 | Stalker |
| 4,879,219 | A | 11/1989 | Wands et al. |
| 4,940,835 | A | 7/1990 | Shah et al. |
| 4,971,908 | A | 11/1990 | Kishore et al. |
| 5,004,863 | A | 4/1991 | Umbeck |
| 5,011,771 | A | 4/1991 | Bellet et al. |
| 5,013,659 | A | 5/1991 | Bedbrook et al. |
| 5,015,580 | A | 5/1991 | Christou et al. |
| 5,023,243 | A | 6/1991 | Tullis |
| 5,034,506 | A | 7/1991 | Summerton et al. |
| 5,094,945 | A | 3/1992 | Comai |
| 5,141,870 | A | 8/1992 | Bedbrook et al. |
| 5,145,783 | A | 9/1992 | Kishore et al. |
| 5,159,135 | A | 10/1992 | Umbeck |
| 5,166,315 | A | 11/1992 | Summerton et al. |

(Continued)

FOREIGN PATENT DOCUMENTS

| | | | |
|---|---|---|---|
| CN | 101279950 | A | 10/2008 |
| CN | 101279951 | A | 10/2008 |

(Continued)

OTHER PUBLICATIONS

Alarcón-Reverte et al., "Resistance to ACCase-inhibiting herbicides in the weed *Lolium multiflorum," Comm. Appl. Biol. Sci.*, 73(4):899-902 (2008).

Amarzguioui et al., "An algorithm for selection of functional siRNA sequences," *Biochemical and Biophysical Research Communications*, 316:1050-1058 (2004).

Ambrus et al., "The Diverse Roles of RNA Helicases in RNAi," *Cell Cycle*, 8(21):3500-3505 (2009).

An et al., "Transient RNAi Induction against Endogenous Genes in Arabidopsis Protoplasts Using in Vitro-Prepared Double-Stranded RNA," *Biosci Biotechnol Biochem*, 69(2):415-418 (2005).

Andersson et al., "A novel selection system for potato transformation using a mutated AHAS gene," *Plant Cell Reports*, 22(4):261-267 (2003).

(Continued)

*Primary Examiner* — Tracy Vivlemore

(74) *Attorney, Agent, or Firm* — Amanda Carmany-Rampey; David R. Marsh; Arnold & Porter LLP

(57) ABSTRACT

This application provides and discloses anti-parasitic, anti-pest or insecticidal nucleic acid molecules and their calmodulin target genes for the control of arthropod parasites and pests. This application further provides methods and compositions for the control and treatment of parasites and pests in *Apis mellifera* (honey bee) hives.

15 Claims, 7 Drawing Sheets

(56) References Cited

U.S. PATENT DOCUMENTS

| | | |
|---|---|---|
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,642,435 B1 | 11/2003 | Antoni et al. |
| 6,644,341 B1 | 11/2003 | Chemo et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |

(56) References Cited

U.S. PATENT DOCUMENTS 7,304,209 B2 12/2007 Zink et al.
7,312,379 B2 12/2007 Andrews et al.
7,323,310 B2 1/2008 Peters et al.
7,371,927 B2 5/2008 Yao et al.
7,392,379 B2 6/2008 Le Pennec et al.
7,405,347 B2 7/2008 Hammer et al.
7,406,981 B2 8/2008 Hemo et al.
7,462,379 B2 12/2008 Fukuda et al.
7,485,777 B2 2/2009 Nakajima et al.
7,525,013 B2 4/2009 Hildebrand et al.
7,550,578 B2 6/2009 Budworth et al.
7,622,301 B2 11/2009 Ren et al.
7,657,299 B2 2/2010 Huizenga et al.
7,671,254 B2 3/2010 Tranel et al.
7,714,188 B2 5/2010 Castle et al.
7,738,626 B2 6/2010 Weese et al.
7,807,791 B2 10/2010 Sekar et al.
7,838,263 B2 11/2010 Dam et al.
7,838,733 B2 11/2010 Wright et al.
7,842,856 B2 11/2010 Tranel et al.
7,884,262 B2 2/2011 Clemente et al.
7,910,805 B2 3/2011 Duck et al.
7,935,869 B2 5/2011 Pallett et al.
7,943,819 B2 5/2011 Baum et al.
7,973,218 B2 7/2011 McCutchen et al.
8,090,164 B2 1/2012 Bullitt et al.
8,143,480 B2 3/2012 Axtell et al.
8,548,778 B1 10/2013 Hart et al.
8,554,490 B2 10/2013 Tang et al.
2001/0042257 A1 11/2001 Connor-Ward et al.
2002/0114784 A1 8/2002 Li et al.
2003/0150017 A1 8/2003 Mesa et al.
2003/0154508 A1 8/2003 Stevens et al.
2003/0167537 A1 9/2003 Jiang
2004/0053289 A1 3/2004 Allen et al.
2004/0055041 A1 3/2004 Labate et al.
2004/0072692 A1 4/2004 Hoffmann et al.
2004/0082475 A1 4/2004 Hoffman et al.
2004/0123347 A1 6/2004 Hinchey et al.
2004/0126845 A1 7/2004 Eenennaam et al.
2004/0133944 A1 7/2004 Hake et al.
2004/0147475 A1 7/2004 Li et al.
2004/0177399 A1 9/2004 Hammer et al.
2004/0216189 A1 10/2004 Houmard et al.
2004/0244075 A1 12/2004 Cai et al.
2005/0005319 A1 1/2005 della-Cioppa et al.
2005/0215435 A1 9/2005 Menges et al.
2006/0009358 A1 1/2006 Kibler et al.
2006/0021087 A1 1/2006 Baum et al.
2006/0111241 A1 5/2006 Gerwick, II et al.
2006/0130172 A1 6/2006 Whaley et al.
2006/0135758 A1 6/2006 Wu
2006/0200878 A1 9/2006 Lutfiyya et al.
2006/0223708 A1 10/2006 Hoffmann et al.
2006/0223709 A1 10/2006 Helmke et al.
2006/0247197 A1 11/2006 Van De Craen et al.
2006/0272049 A1 11/2006 Waterhouse et al.
2006/0276339 A1 12/2006 Windsor et al.
2007/0011775 A1 1/2007 Allen et al.
2007/0021360 A1* 1/2007 Nyce .................... A61K 31/122
514/44 A
2007/0050863 A1 3/2007 Tranel et al.
2007/0124836 A1 5/2007 Baum et al.
2007/0199095 A1 8/2007 Allen et al.
2007/0250947 A1 10/2007 Boukharov et al.
2007/0259785 A1 11/2007 Heck et al.
2007/0281900 A1 12/2007 Cui et al.
2007/0300329 A1 12/2007 Allen et al.
2008/0022423 A1 1/2008 Roberts et al.
2008/0050342 A1 2/2008 Fire et al.
2008/0092256 A1 4/2008 Kohn
2008/0113351 A1* 5/2008 Naito .................. A61K 31/713
435/6.11
2008/0155716 A1 6/2008 Sonnewald et al.
2008/0214443 A1 9/2008 Baum et al.
2009/0011934 A1 1/2009 Zawierucha et al.
2009/0018016 A1 1/2009 Duck et al.
2009/0036311 A1 2/2009 Witschel et al.
2009/0054240 A1 2/2009 Witschel et al.
2009/0075921 A1* 3/2009 Ikegawa ............ A61K 38/1709
514/44 R
2009/0098614 A1 4/2009 Zamore et al.
2009/0118214 A1 5/2009 Paldi et al.
2009/0137395 A1 5/2009 Chicoine et al.
2009/0165153 A1 6/2009 Wang et al.
2009/0165166 A1 6/2009 Feng et al.
2009/0205079 A1 8/2009 Kumar et al.
2009/0215628 A1 8/2009 Witschel et al.
2009/0293148 A1 11/2009 Ren et al.
2009/0298787 A1 12/2009 Raemaekers et al.
2009/0307803 A1 12/2009 Baum et al.
2010/0005551 A1 1/2010 Roberts et al.
2010/0048670 A1* 2/2010 Biard ..................... C12N 15/86
514/44 A
2010/0068172 A1 3/2010 Van De Craen
2010/0071088 A1 3/2010 Sela et al.
2010/0099561 A1 4/2010 Selby et al.
2010/0100988 A1 4/2010 Tranel et al.
2010/0152443 A1 6/2010 Hirai et al.
2010/0154083 A1 6/2010 Ross et al.
2010/0247578 A1 9/2010 Salama
2011/0015084 A1 1/2011 Christian et al.
2011/0015284 A1 1/2011 Dees et al.
2011/0028412 A1 2/2011 Cappello et al.
2011/0035836 A1 2/2011 Eudes et al.
2011/0053226 A1 3/2011 Rohayem
2011/0098180 A1 4/2011 Michel et al.
2011/0105327 A1 5/2011 Nelson
2011/0105329 A1 5/2011 Song et al.
2011/0112570 A1 5/2011 Mannava et al.
2011/0126310 A1 5/2011 Feng et al.
2011/0126311 A1 5/2011 Velcheva et al.
2011/0152339 A1 6/2011 Brown et al.
2011/0152346 A1 6/2011 Karleson et al.
2011/0152353 A1 6/2011 Koizumi
2011/0160082 A1 6/2011 Woo et al.
2011/0166022 A1 7/2011 Israels et al.
2011/0166023 A1 7/2011 Nettleton-Hammond et al.
2011/0171176 A1 7/2011 Baas et al.
2011/0171287 A1 7/2011 Saarma et al.
2011/0177949 A1 7/2011 Krapp et al.
2011/0185444 A1 7/2011 Li et al.
2011/0185445 A1 7/2011 Bogner et al.
2011/0191897 A1 8/2011 Poree et al.
2011/0201501 A1 8/2011 Song et al.
2011/0296555 A1 12/2011 Ivashuta et al.
2011/0296556 A1 12/2011 Sammons et al.
2012/0036594 A1 2/2012 Cardoza et al.
2012/0107355 A1 5/2012 Harris et al.
2012/0108497 A1 5/2012 Paldi et al.
2012/0137387 A1 5/2012 Baum et al.
2012/0150048 A1 6/2012 Kang et al.
2012/0156784 A1 6/2012 Adams, Jr. et al.
2012/0164205 A1 6/2012 Baum et al.
2012/0185967 A1 7/2012 Sela et al.
2012/0230565 A1 9/2012 Steinberg et al.
2012/0258646 A1 10/2012 Sela et al.
2013/0041004 A1 2/2013 Drager et al.
2013/0047297 A1 2/2013 Sammons et al.
2013/0047298 A1 2/2013 Tang
2013/0060133 A1 3/2013 Kassab et al.
2013/0067618 A1 3/2013 Ader et al.
2013/0084243 A1 4/2013 Goetsch et al.
2013/0096073 A1 4/2013 Sidelman
2013/0097726 A1 4/2013 Ader et al.
2013/0212739 A1 8/2013 Giritch et al.
2013/0226003 A1 8/2013 Edic et al.
2013/0247247 A1 9/2013 Ader et al.
2013/0254940 A1 9/2013 Ader et al.
2013/0254941 A1 9/2013 Ader et al.
2013/0288895 A1 10/2013 Ader et al.
2013/0318657 A1 11/2013 Avniel et al.
2013/0318658 A1 11/2013 Ader et al.
2013/0324842 A1 12/2013 Mittal et al.

(56) References Cited

U.S. PATENT DOCUMENTS

2013/0326731 A1 12/2013 Ader et al.
2014/0018241 A1 1/2014 Sammons et al.
2014/0057789 A1 2/2014 Sammons et al.
2014/0109258 A1 4/2014 Van De Craen et al.
2014/0230090 A1 8/2014 Avniel et al.
2014/0274712 A1 9/2014 Finnessy et al.
2014/0296503 A1 10/2014 Avniel et al.
2015/0096079 A1 4/2015 Avniel et al.
2015/0143580 A1 5/2015 Beattie et al.
2015/0159156 A1 6/2015 Inberg et al.
2015/0203867 A1 7/2015 Beattie et al.
2015/0240258 A1 8/2015 Beattie et al.
2016/0015035 A1 1/2016 Tao
2016/0029644 A1 2/2016 Tao

FOREIGN PATENT DOCUMENTS

CN 101914540 A 12/2010
DE 10000600 A1 7/2001
DE 10116399 A1 10/2002
DE 10256353 A1 6/2003
DE 10256354 A1 6/2003
DE 10256367 A1 6/2003
DE 10204951 A1 8/2003
DE 10234875 A1 2/2004
DE 10234876 A1 2/2004
DE 102004054666 A1 5/2006
DE 102005014638 A1 10/2006
DE 102005014906 A1 10/2006
DE 102007012168 A1 9/2008
DE 102010042866 A1 5/2011
EP 0 804 600 A1 11/1997
EP 1 157 991 A2 11/2001
EP 1 238 586 A1 9/2002
EP 1 416 049 A1 5/2004
EP 2 147 919 A1 1/2010
EP 2 160 098 B1 11/2010
EP 2 530 159 A1 3/2011
EP 2 305 813 A2 4/2011
EP 2 545 182 A1 1/2013
JP 2001253874 A 9/2001
JP 2002080454 A 3/2002
JP 2002138075 A 5/2002
JP 2002145707 A 5/2002
JP 2002220389 A 8/2002
JP 2003064059 A 3/2003
JP 2003096059 A 4/2003
JP 2004051628 A 2/2004
JP 2004107228 A 4/2004
JP 2005008583 A 1/2005
JP 2005239675 A 9/2005
JP 2005314407 A 11/2005
JP 2006232824 A 9/2006
JP 2006282552 A 10/2006
JP 2007153847 A 6/2007
JP 2007161701 A 6/2007
JP 2007182404 A 7/2007
JP 2008074840 A 4/2008
JP 2008074841 A 4/2008
JP 2008133207 A 6/2008
JP 2008133218 A 6/2008
JP 2008169121 A 7/2008
JP 2009067739 A 4/2009
JP 2009114128 A 5/2009
JP 2009126792 A 6/2009
JP 2009137851 A 6/2009
WO WO 89/11789 A1 12/1989
WO WO 95/34659 A1 12/1995
WO WO 95/34668 A2 12/1995
WO WO 96/05721 A1 2/1996
WO WO 96/33270 A1 10/1996
WO WO 96/38567 A2 12/1996
WO WO 96/40964 A2 12/1996
WO WO 99/24585 A1 5/1999
WO WO 99/26467 A1 6/1999
WO WO 99/27116 A2 6/1999
WO WO 99/32619 A1 7/1999
WO WO 99/61631 A1 12/1999
WO WO 99/67367 A1 12/1999
WO WO 00/32757 A2 6/2000
WO WO 00/44914 A1 8/2000
WO WO 02/14472 A2 2/2002
WO WO 02/066660 A2 8/2002
WO WO 03/000679 A2 1/2003
WO WO 03/006422 A1 1/2003
WO WO 03/013247 A1 2/2003
WO WO 03/016308 A1 2/2003
WO WO 03/020704 A1 3/2003
WO WO 03/022051 A1 3/2003
WO WO 03/022831 A1 3/2003
WO WO 03/022843 A1 3/2003
WO WO 03/029243 A2 4/2003
WO WO 03/037085 A1 5/2003
WO WO 03/037878 A1 5/2003
WO WO 03/045878 A2 6/2003
WO WO 03/050087 A2 6/2003
WO WO 03/051823 A1 6/2003
WO WO 03/051824 A1 6/2003
WO WO 03/051846 A2 6/2003
WO WO 03/064625 A2 8/2003
WO WO 03/076409 A1 9/2003
WO WO 03/077648 A2 9/2003
WO WO 03/087067 A1 10/2003
WO WO 03/090539 A1 11/2003
WO WO 03/091217 A1 11/2003
WO WO 03/093269 A2 11/2003
WO WO 03/104206 A2 12/2003
WO WO 2004/002947 A1 1/2004
WO WO 2004/002981 A2 1/2004
WO WO 2004/005485 A2 1/2004
WO WO 2004/009761 A2 1/2004
WO WO 2004/011429 A1 2/2004
WO WO 2004/022771 A2 3/2004
WO WO 2004/029060 A1 4/2004
WO WO 2004/035545 A2 4/2004
WO WO 2004/035563 A1 4/2004
WO WO 2004/035564 A1 4/2004
WO WO 2004/037787 A1 5/2004
WO WO 2004/049806 A1 6/2004
WO WO 2004/062351 A2 7/2004
WO WO 2004/067518 A1 8/2004
WO WO 2004/067527 A1 8/2004
WO WO 2004/074443 A2 9/2004
WO WO 2004/077950 A1 9/2004
WO WO 2005/000824 A1 1/2005
WO WO 2005/003362 A2 1/2005
WO WO 2005/007627 A1 1/2005
WO WO 2005/040152 A1 5/2005
WO WO 2005/047233 A1 5/2005
WO WO 2005/047281 A1 5/2005
WO WO 2005/061443 A2 7/2005
WO WO 2005/061464 A1 7/2005
WO WO 2005/068434 A1 7/2005
WO WO 2005/070889 A1 8/2005
WO WO 2005/089551 A1 9/2005
WO WO 2005/095335 A1 10/2005
WO WO 2005/107437 A2 11/2005
WO WO 2005/110068 A2 11/2005
WO WO 2006/006569 A1 1/2006
WO WO 2006/024820 A1 3/2006
WO WO 2006/029828 A1 3/2006
WO WO 2006/029829 A1 3/2006
WO WO 2006/037945 A1 4/2006
WO WO 2006/050803 A1 5/2006
WO WO 2006/074400 A2 7/2006
WO WO 2006/090792 A1 8/2006
WO WO 2006/123088 A2 11/2006
WO WO 2006/125687 A1 11/2006
WO WO 2006/125688 A1 11/2006
WO WO 2006/138638 A1 12/2006
WO WO 2007/003294 A1 1/2007
WO WO 2007/007316 A1 1/2007
WO WO 2007/024783 3/2007
WO WO 2007/026834 A1 3/2007

(56) References Cited

FOREIGN PATENT DOCUMENTS

WO WO 2007/035650 A2 3/2007
WO WO 2007/039454 A1 4/2007
WO WO 2007/070389 A2 6/2007
WO WO 2007/071900 A1 6/2007
WO WO 2007/074405 A2 7/2007
WO WO 2007/077201 A1 7/2007
WO WO 2007/077247 A1 7/2007
WO WO 2007/080126 A2 7/2007
WO WO 2007/080127 A2 7/2007
WO WO 2007/096576 A1 8/2007
WO WO 2007/051462 A2 10/2007
WO WO 2007/119434 A1 10/2007
WO WO 2007/134984 A1 11/2007
WO WO 2008/007100 A2 1/2008
WO WO 2008/009908 A1 1/2008
WO WO 2008/029084 A1 3/2008
WO WO 2008/042231 A2 4/2008
WO WO 2008/059948 A1 5/2008
WO WO 2008/063203 A2 5/2008
WO WO 2008/071918 A1 6/2008
WO WO 2008/074991 A1 6/2008
WO WO 2008/084073 A1 7/2008
WO WO 2008/100426 A2 8/2008
WO WO 2008/102908 A1 8/2008
WO WO 2008/148223 A1 12/2008
WO WO 2008/152072 A2 12/2008
WO WO 2008/152073 A2 12/2008
WO WO 2009/000757 A1 12/2008
WO WO 2009/005297 A2 1/2009
WO WO 2009/035150 A2 3/2009
WO WO 2009/046384 A1 4/2009
WO WO 2009/063180 A1 5/2009
WO WO 2009/068170 A2 6/2009
WO WO 2009/068171 A2 6/2009
WO WO 2009/086041 A1 7/2009
WO WO 2009/090401 A2 7/2009
WO WO 2009/090402 A2 7/2009
WO WO 2009/115788 A1 9/2009
WO WO 2009/116558 A1 9/2009
WO WO 2009/125401 A2 10/2009
WO WO 2009/152995 A1 12/2009
WO WO 2009/158258 A1 12/2009
WO WO 2010/012649 A1 2/2010
WO WO 2010/026989 A1 3/2010
WO WO 2010/034153 A1 4/2010
WO WO 2010/049270 A1 5/2010
WO WO 2010/049369 A1 5/2010
WO WO 2010/049405 A1 5/2010
WO WO 2010/049414 A1 5/2010
WO WO 2010/056519 A1 5/2010
WO WO 2010/063422 A1 6/2010
WO WO 2010/069802 A1 6/2010
WO WO 2010/078906 A2 7/2010
WO WO 2010/078912 A1 7/2010
WO WO 2010/104217 A1 9/2010
WO WO 2010/108611 A1 9/2010
WO WO 2010/112826 A2 10/2010
WO WO 2010/116122 A2 10/2010
WO WO 2010/119906 A1 10/2010
WO WO 2010/130970 A1 11/2010
WO WO 2011/001434 A1 1/2011
WO WO 2011/003776 A2 1/2011
WO WO 2011/035874 A1 3/2011
WO WO 2011/045796 A1 4/2011
WO WO 2011/065451 A1 6/2011
WO WO 2011/067745 A2 6/2011
WO WO 2011/080674 A2 7/2011
WO WO 2011/112570 A1 9/2011
WO WO 2011/132127 A1 10/2011
WO WO 2012/001626 A1 1/2012
WO WO 2012/056401 A1 5/2012
WO WO 2012/092580 A2 7/2012
WO WO 2013/010691 A1 1/2013
WO WO 2013/025670 A1 2/2013
WO WO 2013/039990 A1 3/2013
WO WO 2013/040005 A1 3/2013
WO WO 2013/040021 A1 3/2013
WO WO 2013/040033 A1 3/2013
WO WO 2013/040049 A1 3/2013
WO WO 2013/040057 A1 3/2013
WO WO 2013/040116 A9 3/2013
WO WO 2013/040117 A9 3/2013
WO WO 2013/153553 A2 10/2013
WO WO 2013/175480 A1 11/2013
WO WO 2014/022739 A2 2/2014
WO WO 2014/106837 A2 7/2014
WO WO 2014/106838 A2 7/2014
WO WO 2014/151255 A1 9/2014
WO WO 2014/164761 A1 10/2014
WO WO 2014/164797 A1 10/2014
WO WO 2015/010026 A2 1/2015

OTHER PUBLICATIONS

Anonymous, "A handbook for high-level expression and purification of 6xHis-tagged proteins," *The QUIexpressionist*, (2003).

Anonymous, "Agronomy Facts 37: Adjuvants for enhancing herbicide performance," *n.p.*, 1-8, (Jan. 26, 2000), *Web*, (Jan. 21, 2014).

Anonymous, "Devgen, The mini-Monsanto," KBC Securities (2006).

Anonymous, "Do Monsanto have the next big thing?," *Austalian Herbicide Resistance Initiative* (*AHRI*), (Apr. 23, 2013) *Web*. (Jan. 19, 2015).

Aoki et al., "In Vivo Transfer Efficiency of Antisense Oligonucleotides into the Myocardium Using HVJ-Liposome Method," Biochem Biophys Res Commun, 231:540-545 (1997).

Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).

Artmymovich, "Using RNA interference to increase crop yield and decrease pest damage," *MMG 445 Basic Biotech.*, 5(1):7-12 (2009).

Australian Patent Examination report No. 1 issued Nov. 11, 2013, in Australian Application No. 2011224570.

Axtell et al., "A Two-Hit Trigger for siRNA Biogenesis in Plants," *Cell*, 127:565-577 (2006).

Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).

Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).

Baulcombe, "RNA silencing and heritable epigenetic effects in tomato and Arabidopsis," Abstract $13^{th}$ Annual Fall Symposium, Plant Genomes to Phenomes, Donald Danforth Plant Science Center, 28-30 (2011).

Bayer et al., "Programmable ligand-controlled riboregulators of eukaryotic gene expression," *Nature Biotechnol.*, 23(3):337-343 (2005).

Beal, et al., "Second Structural Motif for Recognition of DNA by Oligonucleotide-Directed Triple-Helix Formation," *Science*, 251:1360-1363 (1992).

Becker et al., "Fertile transgenic wheat from microprojectile bombardment of scutellar tissue," *The Plant Journal*, 5(2):299-307 (1994).

Bhargava et al., "Long double-stranded RNA-mediated RNA interference as a tool to achieve site-specific silencing of hypothalamic neuropeptides," *Brain Research Protocols*, 13:115-125 (2004).

Boletta et al., "High Efficient Non-Viral Gene Delivery to the Rat Kidney by Novel Polycationic Vectors," *J. Am Soc. Nephrol.*, 7:1728 (1996).

Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).

Bolter et al., "A chloroplastic inner envelope membrane protease is essential for plant development," *FEBS Letters*, 580:789-794 (2006).

(56) References Cited

OTHER PUBLICATIONS

Breaker et al., "A DNA enzyme with Mg2+-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chee et al., "Transformation of Soybean (*Glycine max*) by Infecting Germinating Seeds with *Agrobacterium tumefaciens,*" *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens,*" *Plant Cell Reports*, 15:653-657 (1996).
Chi et al., "The Function of RH22, a DEAD RNA Helicase, in the Biogenesis of the 50S Ribosomal Subunits of Arabidopsis Chloroplasts," *Plant Physiology*, 158:693-707 (2012).
Chinese Office Action issued Aug. 28, 2013 in Chinese Application No. 201180012795.2.
Clough et al., "Floral dip: a simplified method for Agrobacterium-mediated transformation of *Arabidopsis thaliana,*" *The Plant Journal*, 16(6):735-743 (1998).
CN101914540 Patent Diclosure, "Introduction of RNA into plant by interference," (2010).
Colbourne et al., "The Ecoresponsive Genome of Daphnia pulex," *Science*, 331(6017):555-561 (2011).
Colombian Office Action issued Aug. 2, 2013 in Application No. 12 152898.
Colombian Office Action issued Feb. 21, 2014 in Application No. 12 152898.
Cooney et al., "Site-Specific Oligonucleotide Binding Represses Transcription of the Human c-myc Gene in Vitro," *Science* ,241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Dalmay et al., "An RNA-Depenedent RNA Polymerase Gene in *Arabidopsis* is Required for Posttranscriptional Gene Silencing Mediated by a Transgene but Not by a Virus," *Cell*, 101:543-553 (2000).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Dietemann et al., "*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action issued Feb. 24, 2014, in Application No. 201201264.
European Cooperation in the field of Scientific and Technical Research—Memorandum of Understanding for Cost Action FA0806 (2008).
European Supplemental Search Report issued Oct. 8, 2013 in Application No. 11753916.3.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Feb. 2, 2015, in European Patent Application No. 12 830 932.5.
Extended European Search Report dated Feb. 3, 2015, in European Patent Application No. 12 831 945.6.
Extended European Search Report dated Feb. 27, 2015, in European Patent Application No. 12 832 160.1.
Extended European Search Report dated Mar. 3, 2015, in European Patent Application No. 12 831 166.9.
Extended European Search Report dated Mar. 17, 2015, in European Patent Application No. 12 831 684.1.
Partial Supplementary European Search Report dated Mar. 2, 2015, in European Patent Application No. 12 831 494.5.
Farooq et al., "Rice seed priming," *IPRN*, 30(2):45-48 (2005).
Fire et al., "Potent and specific genetic interference by double-stranded RNA in *Caenorhabditis elegans*," Nature, 391:806-811 (1998).
First Examination Report issued on Apr. 23, 2013, in New Zealand Patent Application No. 601784.
First Examination Report issued on Jul. 28, 2014, in New Zealand Patent Application No. 627060.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 on May 16, 2014.
Gaines et al., "Gene amplification confers glyphosate resistance in *Amaranthus palmeri,*" *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor: Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.

(56) References Cited

OTHER PUBLICATIONS

GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. AY545657.1, published 2004.
GenBank accession No. GI:186478573, published Jan. 22, 2014.
GenEmbl FJ861243, published Feb. 3, 2010.
Gong et al., "Silencing of Rieske iron—sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus?," Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus," Science*, 222:1346-1349 (1983).
Hoekema et al., "A binary plant vector strategy based on separation of *vir*- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability issued on Sep. 11, 2014, in International Application No. PCT/IL13/50447.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
International Search Report and the Written Opinion dated Oct. 1, 2013, in International Application No. PCT/IL2013/050447.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636(2012).
Jones-Rhoades et al., "MicroRNAs and Their Regulatory Roles in Plants," *Annu. Rev. Plant Biol.*, 57:19-53 (2006).
Josse et al., "A DELLA in Disguise: Spatula Restrains the Growth of the Developing *Arabidopsis* Seedling," Plant Cell, 23:1337-1351 (2011).
Kam et al., "Nanotube Molecular Transporters: In—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana," Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes are Able to Penetrate Plant Seed Coat and Dramatically Affect Seed Germination and Plant Growth," *ACS Nano*, 3(10):3221-3227 (2009).

(56) References Cited

OTHER PUBLICATIONS

Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Kronenwett et al., "Oligodeoxyribonucleotide Uptake in Primary Human Hematopoietic Cells is Enhanced by Cationic Lipids and Depends on the Hematopoietic Cell Subset," *Blood*, 91(3):852-862 (1998).
Kumar et al., "Sequencing, De Novo Assembly and Annotation of the Colorado Potato Beetle, *Leptinotarsa decemlineata*,Transcriptome," *PLoS One*, 9(1):e86012 (2014).
Kusaba et al., "*Low glutelin content1* : A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli," Nucleic Acids Research*, 29(17):3583-3594 (2001).
Li et al., "Establishment of a highly efficient transformation system for pepper (*Capsicum amiuum* L.)," *Plant Cell Reports*, 21: 785-788 (2003).
Li et al., "The FAST technique: a simplified Agrobacterium-based transformation method for transient gene expression analysis in seedlings of Arabidopsis and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli," BMC Biotechnology*, 10:85 (2010).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding; proteins by oligonticleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana," Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene *crtl* in transgenic plants showing an increase of β-carotene biosynthesis activity and resistance to the bleaching herbicide norflurazon," *The Plant Journal*, 4(5):833-840 (1993).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis yellow variegated* Mutants," *The Plant Cell*, 19:1313-1328 (2007).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants are Mobile and Direct Epigenetic Modification in Recipient Cells," *Science*, 328:872-875 (2010).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action issued on Jan. 6, 2015, in Japanese Patent Application No. 2012-557165.
Office Action issued on Nov. 19, 2014, in Eurasian Patent Application No. 201201264/28.
Office Action issued on Nov. 3, 2014, in Chinese Patent Application No. 201180012795.2.
Ongvarrasopone et al., "A Simple and Cost Effective Method to Generate dsRNA for RNAi Studies in Invertebrates," *Science Asia*, 33:35-39 (2007).
Ouellet et al., "Members of the Acetohydroxyacid Synthase Muligene Family of Brassica Napus Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of *Shrunken*-2 Corn," *J. Amer. Soc. Hort. Sci.*, 119(3):629-635 (1994).

(56) References Cited

OTHER PUBLICATIONS

Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by Arabidopsis induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola," Pesticide Biochem. Physiol.*, 84(3):227-235 (2006).
Qiwei,"Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Sharma et al., "A simple and efficient *Agrobacterium*-mediated procedure for transformation of tomato," *J. Biosci.*, 34(3):423 433 (2009).
Sijen et al. "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Temple et al., "Can glutamine synthetase activity levels be modulated in transgenic plants by the use of recombinant DNA technology?" *Transgenic Plants and Plant Biochemistry*, 22:915-920 (1994).
Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "Clustal W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.* ;573(1-3):127-134 (2004).
Turina et al., "Tospoviruses in the Mediterranean Area," *Advances in Virus Research*, 84:403-437 (2012).
Tuschl, "RNA Interference and Small Interfering RNAs," *ChemBiochem.* 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).

(56) References Cited

OTHER PUBLICATIONS

Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010) Herewith.
van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "Agrobacterium-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al., "*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata,*" *Pest Manag Sci*, 67:175-182 (2010).
Agrios, *Plant Pathology* (Second Edition), 2:466-470 (1978).
Bai et al., "Naturally Occurring Broad-Spectrum Powdery Mildew Resistance in a Central American Tomato Accession is Caused by Loss of *Mlo* Function," *MPMI*, 21(1):30-39 (2008).
Bourgeois et al., "Field and producer survey of ACCase resistant wild oat in Manitoba," *Canadian Journal of Plant Science*, 709-715 (1997).
Brugière et al., "Glutamine Synthetase in the Phloem Plays a Major Role in Controlling Proline Production," *The Plant Cell*, 11:1995-2011 (1999).
Campbell et al., "Gene-knockdown in the honey bee mite *Varroa destructor* by a non-invasive approach: studies on a glutathione S-transferase," *Parasites & Vectors*, 3(1):73, pp. 1-10 (2010).
Chang et al., "Cellular Internalization of Fluorescent Proteins via Arginine-rich Intracellular Delivery Peptide in Plant Cells," *Plant Cell Physiol.*, 46(3):482-488 (2005).
Chupp et al., "Chapter 8: White Rust," *Vegetable Diseases and Their Control*, The Ronald Press Company, New York, pp. 267-269 (1960).
Communication pursuant to Article 94(3) EPC dated Jun. 26, 2015, as received in European Patent Application No. 11 753 916.3.
Communication pursuant to Article 94(3) EPC dated Oct. 23, 2015, as received in European Patent Application No. 12 831 945.6.
Communication pursuant to Article 94(3) EPC dated Jan. 14, 2016, in European Patent Application No. 12 832 415.9.
Desai et al., "Reduction in deformed wing virus infection in larval and adult honey bees (*Apis mellifera* L.) by double-stranded RNA ingestion," *Insect Molecular Biology*, 21(4):446-455 (2012).
Emery et al., "Radial Patterning of *Arabidopsis* Shoots by Class III HD-ZIP and Kanadi Genes," *Current Biology*, 13:1768-1774 (2003).
Extended European Search Report dated Jun. 29, 2015, in European Patent Application No. 12 831 494.5.
Extended European Search Report dated Jan. 20, 2016, in European Patent Application No. 13 794 339.5.
Final Office Action dated Nov. 10, 2015, in U.S. Appl. No. 13/612,985.
Final Office Action dated Nov. 7, 2013, in U.S. Appl. No. 13/042,856.
Final Office Action dated Nov. 30, 2015, in U.S. Appl. No. 13/612,948.
First Office Action issued Mar. 2, 2015, in Chinese Patent Application No. 201280054819.5.
First Office Action issued Mar. 12, 2015, in Chinese Patent Application No. 201280053984.9.
First Office Action issued May 27, 2015, in Chinese Patent Application No. 201280054179.8.
First Office Action issued Jul. 7, 2015, in Chinese Patent Application No. 201280054820.8.
First Office Action issued Aug. 31, 2015, in Chinese Patent Application No. 201280053985.3.

(56) References Cited

OTHER PUBLICATIONS

First Office Action issued Sep. 9, 2015, in Chinese Patent Application No. 201280055409.2.
First Office Action dated Feb. 2, 2016, in Chinese Patent Application No. 201380039346.6.
International Preliminary Report on Patentability (Chapter II) mailed Jul. 24, 2015, in International Application No. PCT/US2014/047204.
International Search Report and Written Opinion mailed Jul. 8, 2015, in International Application No. PCT/US2015/011408.
International Search Report and Written Opinion mailed Mar. 26, 2015, in International Application No. PCT/US2014/069353.
International Search Report and Written Opinion mailed Nov. 24, 2015, in International Application No. PCT/US2015/037522.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Jofre-Garfias et al., "*Agrobacterium*-mediated transformation of *Amaranthus hypochondriacus*: light- and tissue-specific expression of a pea chlorophyll a/b-binding protein promoter," *Plant Cell Reports*, 16:847-852 (1997).
Khan et al., "Matriconditioning of Vegetable Seeds to Improve Stand Establishment in Early Field Plantings," *J. Amer. Soc. Hort. Sci.*, 117(1):41-47 (1992).
Kim et al., "Synthetic dsRNA Dicer substrates enhance RNAi potency and efficacy," *Nature Biotechnology*, 23(2):222-226 (2005).
Lein et al., "Target-based discovery of novel herbicides," *Current Opinion in Plant Biology*, 7:219-225 (2004).
Leopold et al., "Chapter 4: Moisture as a Regulator of Physiological Reaction in Seeds," *Seed Moisture, CSSA Special Publication* No. 14, pp. 51-69 (1989).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Office Action dated Jul. 23, 2015, in Ukrainian Patent Application No. 201211548.
Office Action issued on Oct. 5, 2015, in Eurasian Patent Application No. 201201264/28.
Office Action mailed Sep. 9, 2015, in Chinese Patent Application No. 201280055409.2.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Patent Examination Report No. 1 dated Feb. 8, 2016, in Australian Patent Application No. 2014262189.
Pratt et al., "*Amaranthus rudis* and *A. tuberculatus*, One Species or Two?," *Journal of the Torrey Botanical Society*, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Schweizer et al., "Double-stranded RNA interferes with gene function at the single-cell level in cereals," *The Plant Journal*, 24(6):895-903 (2000).
Senthil-Kumar et al., "A systematic study to determine the extent of gene silencing in *Nicotiana benthamiana* and other *Solanaceae* species when heterologous gene sequences are used for virus-induced gene silencing," *New Phytologist*, 176:782-791 (2007).
Snead et al., "Molecular basis for improved gene silencing by Dicer substrate interfering RNA compared with other siRNA variants," *Nucleic Acids Research*, 41(12):6209-6221 (2013).
Stevens et al., "New Formulation Technology—Silwet® Organosilicone Surfactants Have Physical and Physiological Properties Which Enhance the Performance of Sprays," *Proceedings of the 9th Australian Weeds Conference*, pp. 327-331 (1990).
Street, "Why is DNA (and not RNA) a stable storage form for genetic information?," *Biochemistry Revisited*, pp. 1-4 (2008).
Sutton et al., "Activity of mesotrione on resistant weeds in maize," *Pest Manag. Sci.*, 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).
Tranel et al., "Resistance of weeds to ALS-inhibiting herbicides: what have we learned?," *Weed Science*, 50:700-712 (2002).
Tsugawa et al., "Efficient transformation of rice protoplasts mediated by a synthetic polycationic amino polymer," *Theor Appl Genet*, 97:1019-1026 (1998).
Vermeulen et al., "The contributions of dsRNA structure to Dicer specificity and efficiency," *RNA*, 11(5):674-682 (2005).
Wang et al., "Foliar uptake of pesticides—Present status and future challenge," ScienceDirect, 87:1-8 (2007).

* cited by examiner

COMPOSITIONS AND METHODS FOR CONTROLLING ARTHROPOD PARASITE AND PEST INFESTATIONS

CROSS REFERENCE TO RELATED APPLICATIONS

This application claims the benefit under 35 U.S.C. §119 of U.S. Provisional Application No. 61/899,772, filed Nov. 4, 2013, which is herein incorporated by reference in its entirety.

INCORPORATION OF SEQUENCE LISTING

A computer readable form of the Sequence Listing is filed with this application by electronic submission and is incorporated into this application by reference in its entirety. The Sequence Listing is contained in the file created on Mar. 2, 2015, having the file name P34094US01_SEQ.txt, and is 64,071 bytes in size (as measured in the MS-Windows® operating system).

FIELD OF THE DISCLOSURE

Methods and compositions for controlling parasite and pest infestations of arthropods are provided. Also provided are methods and compositions for controlling *Varroa* mite infestation in bees.

BACKGROUND

Arthropods of various species are increasingly cultured on a commercial scale. Insects and their grubs are nutritious and are eaten both raw and cooked in many cultures. Crustaceans such as crabs, lobsters, crayfish, shrimp and prawns are farmed on a large commercial scale and are an important part of the human diet. In addition to the culture of arthropod species for food, arthropods are also cultured as part of pest management strategies, including for the biological control of other arthropods, for example the culture parasitic wasps for the control of roaches and fire ants. Arthropods may also serve as the source of raw materials such as dyes, drugs, medicines, and antibiotics. Growing with the increasing importance of arthropod culture, are various pests and parasites that destroy the arthropod colonies or greatly reduce the yields of products obtained from arthropod culture. Accordingly, there is an increasing need for methods to control arthropod pests and parasites.

Among the most important species of cultured arthropods is the honey bee. Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor.*

*Varroa* (*Varroa destructor*) mites are the number one parasite of managed honey bees (*Apis mellifera*) and the biggest global threat to commercial beekeeping (Rosenkranz et al. 2010). An adult mite typically enters the worker and drone brood cells before they are capped, primed by honeybee brood pheromone. The mite submerges into the brood food that the bees put inside the cell in anticipation of capping, most probably to avoid being recognized and removed by nurse bees. Following capping of the brood cells by the nurse bees, the mite adheres to the larva and starts to ingest bee larval hemolymph. This process primes oogenesis in the mites, and is followed several days later in laying of male and female eggs. Eventually, the adult *Varroa* exit the cell and cling onto the emerging bees. *Varroa* directly damages the honeybees in multiple ways, most notably by draining resources, adversely affecting the innate honey bee immune system, and by being a very effective vector of viruses (Di Prisco et al. 2011), some of which are known to replicate in the mite, thus dramatically increasing the viral load.

A safe, efficacious and long-lasting solution to the *Varroa* problem is an ongoing challenge that has yet to be met. Currently, beekeepers use a plethora of methods to control *Varroa* levels that include various chemical miticides, most of which have lost efficacy and are toxic and/or leave residues in wax and honey. Other methods include application of oxalic or formic acid, monoterpenes (thymol) and a variety of other management practices, with highly variable outcomes, including toxicity to the treated colonies. Breeding of bees for resistance to *Varroa*, such as selection for Hygienic behavior which results in the removal of infested brood, has provided a limited practical success.

Colony Collapse Disorder (CCD) of honeybees is threatening to annihilate U.S. and world agriculture. Indeed, in the recent outbreak of CCD in the U.S in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on *Varroa* mite control, sanitation and removal of affected hives, treating for opportunistic infections (such as *Nosema*) and improved nutrition. No effective preventative measures have been developed to date.

*Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality.

Current methods of treating *Varroa* infestations are proving to be ineffective as the mites develop resistance to existing miticides. In addition, the use of such miticides may introduce injurious chemicals into honey that is intended for human consumption.

SUMMARY OF THE INVENTION

The present disclosure provides for, and includes, selective insecticide compositions comprising an anti-parasitic, anti-pest or insecticidal nucleic acid molecule having a sequence that is essentially complementary or essentially identical to a region of a calmodulin gene sequence or an RNA transcribed therefrom. In some aspects, the composition further comprises an excipient.

In one aspect, the nucleic acid molecule in the selective insecticide composition is a dsRNA. In some aspects, the dsRNA is an siRNA.

In one aspect, the calmodulin gene sequence has at least 80%, 85%, 90%, 95%, 96%, 97%, 98%, 99% or 100% sequence identity to a sequence selected from SEQ ID NOs:1-4, 6, 23, 26-35, and 69-89. In some aspects, the calmodulin gene sequence comprises at least 18 contiguous nucleotides of a sequence selected from SEQ ID NOs: 1-4, 6, 23, 26-35, and 69-89.

In one aspect, the selective insecticide composition further comprises one or more anti-parasitic, anti-pest or insecticidal nucleic acid molecules that are essentially complementary or essentially identical to a first region of a calmodulin gene sequence. In some aspects, the one or more nucleic acid molecules comprise a second nucleic acid sequence complementary to a second region of a calmodulin gene sequence.

In one aspect, the selective insecticide composition is bee-ingestible, bee-absorbable, mite-ingestible, or mite-absorbable.

In one aspect, the expedient is selected from the group consisting of protein, pollen, carbohydrate, polymer, liquid solvent, sugar syrup, sugar solid, and semi-solid feed. In some aspects, the liquid solvent is selected from the group consisting of sucrose solution and corn syrup solution. In some aspects, the protein is selected from the group consisting of pollen and soy protein. In another aspect, the excipient is a solid selected from sugar, a sugar substitute, or a sugar supplement. In some aspects, the sugar solid comprises sugar microparticles impregnated with a dsRNA nucleic acid sequence.

In one aspect, the instant application discloses bee-ingestible compositions comprising a bee feed and a nucleic acid molecule having a sequence that is essentially identical or essentially complementary to one or more regions of a calmodulin gene sequence, or an RNA transcribed therefrom. In some aspects, the bee feed comprises a bee food selected from the group consisting of corn syrup, a pollen substitute, pollen, a pollen patty, and a fondant. In some aspects, the bee feed further comprises one or more of a mineral salt, an essential oil, Brewers Yeast, yeast extract, trehalose, tryptone, dry milk, lecithin, and Vitamin C. Examples of essential oils include, but are not limited to, wintergreen oil, spearmint oil, peppermint oil, lemongrass oil and tea tree oil.

In another aspect, the instant application discloses a nucleic acid construct comprising an anti-parasitic, anti-pest or insecticidal nucleic acid sequence that is essentially identical or complementary to a region of a calmodulin gene sequence, or an RNA transcribed therefrom, operably linked to a promoter sequence functional in a host cell and capable of producing a dsRNA when introduced into said host cell. In some aspects, the nucleic acid construct further comprises at least one regulatory element selected from the group consisting of translation leader sequences, introns, enhancers, stem-loop structures, repressor binding sequences, termination sequences, pausing sequences, and polyadenylation recognition sequences. In some aspects, the host cell is a bacterial or yeast cell.

In another aspect, the instant application discloses a method of providing a composition to a honeybee, comprising providing the bee an effective amount of a composition comprising an anti-parasitic, anti-pest or insecticidal nucleic acid that is essentially identical or essentially complementary to one or more regions of a calmodulin gene sequence, or an RNA transcribed therefrom, whereby the nucleic acid is present in honeybee tissue.

In another aspect, the instant application discloses a method of treating or preventing disease in a honeybee colony, comprising providing an effective amount of a composition comprising an anti-parasitic, anti-pest or insecticidal nucleic acid that is essentially identical or essentially complementary to one or more regions of a calmodulin gene sequence to a honeybee whereby the nucleic acid is present in honeybee tissue. In some aspects, the calmodulin gene sequence is a *Varroa destructor* calmodulin gene sequence.

In another aspect, the instant application discloses a method of reducing parasitation of a bee by *Varroa destructor*, comprising providing the bee an effective amount of an anti-parasitic, anti-pest or insecticidal nucleic acid composition, wherein the nucleic acid is essentially identical or essentially complementary to one or more regions of a *Varroa destructor* calmodulin gene sequence, or an RNA transcribed therefrom, thereby reducing the parasitation of the bee by *Varroa destructor*.

In another aspect, the instant application discloses a method of reducing the parasite load of a honeybee hive, comprising providing said hive an effective amount of an anti-parasitic, anti-pest or insecticidal nucleic acid that is essentially identical or essentially complementary to one or more regions of a parasite calmodulin gene sequence, or an RNA transcribed therefrom, whereby the parasite load of said hive is reduced.

In another aspect, the instant application discloses a method of selectively treating an arthropod species for parasites, comprising delivering an effective amount of an anti-parasitic, anti-pest or insecticidal nucleic acid that is essentially identical or essentially complementary to one or more regions of a parasite calmodulin gene sequence, or an RNA transcribed therefrom, to an arthropod species.

In another aspect, the instant application provides for, and discloses a method of treating or preventing Colony Collapse Disorder in a honeybee colony, comprising providing an effective amount of a composition to a honeybee colony comprising an anti-parasitic, anti-pest or insecticidal nucleic acid molecule having a sequence that is essentially identical to or essentially complementary to one or more regions of a *Varroa destructor* calmodulin gene sequence whereby the level of *Varroa destructor* infestation is reduced or prevented.

DETAILED DESCRIPTION

Figure 1:
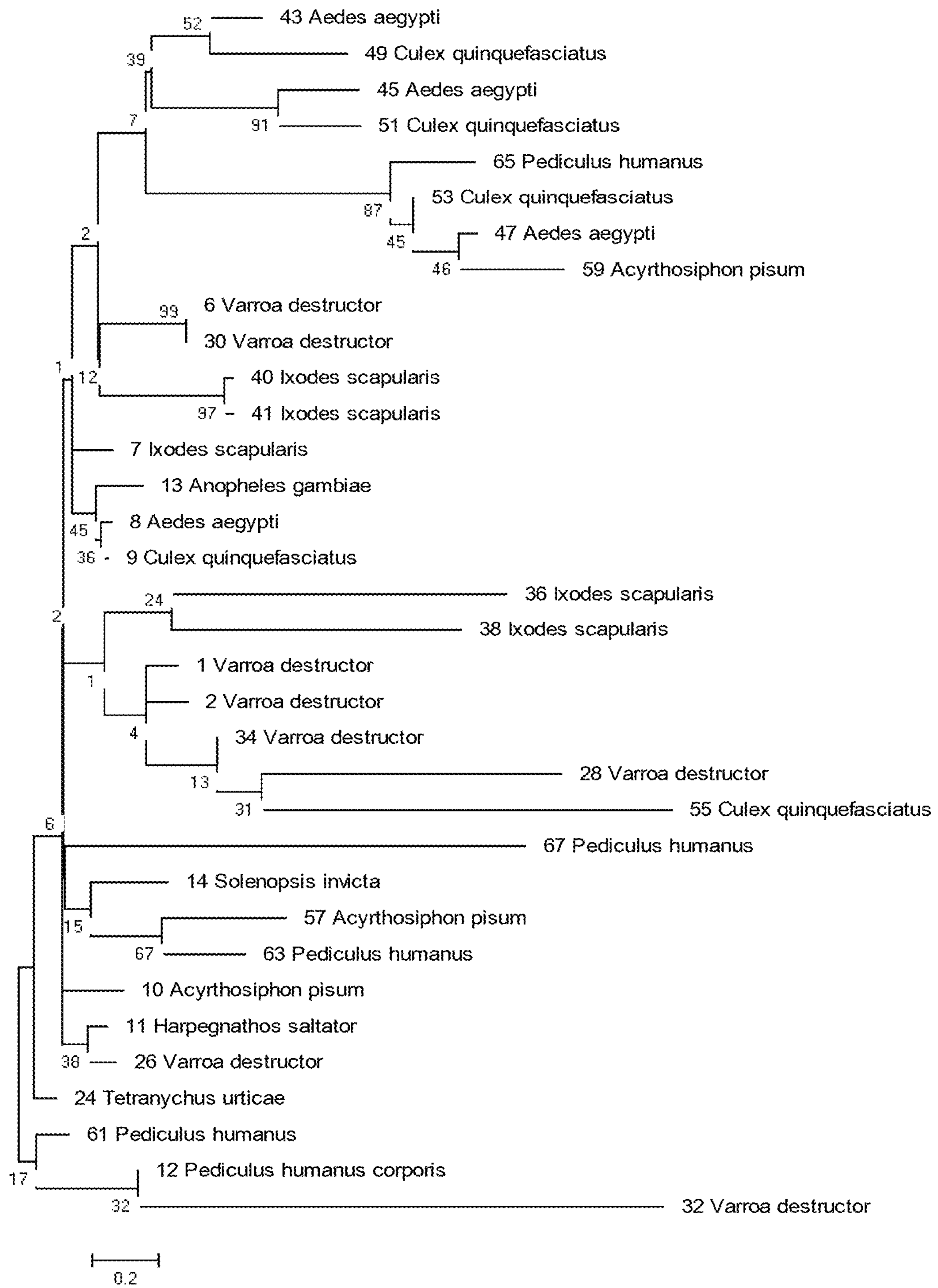
FIG. 1 presents a phylogenetic tree for *Calmodulin* (CAM) genes from different species. The number immediately preceding the species name corresponds to a Sequence Identification Number (SEQ ID NO).

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to a mature *Varroa destructor* calmodulin nucleic acid sequence, or the RNA sequence of a mature *Varroa destructor* calmodulin molecule nucleic acid sequence. Similarly, though SEQ ID NO: 3 is expressed in a RNA sequence format (e.g., reciting U for uracil), depending on the actual type of molecule being described, SEQ ID NO: 3 can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

As used herein the term "about" refers to ±10%.

As used herein, the singular form "a", "an" and "the" include plural references unless the context clearly dictates otherwise. For example, the term "a compound" or "at least one compound" may include a plurality of compounds, including mixtures thereof.

As used herein, "essentially identical" or "essentially complementary" refers to a nucleic acid (or at least one strand of a double-stranded nucleic acid or portion thereof, or a portion of a single strand nucleic acid) that hybridizes under physiological conditions to the endogenous gene, an RNA transcribed therefrom, or a fragment thereof, to effect regulation or suppression of the endogenous gene. For example, in some aspects, a nucleic acid has 100 percent sequence identity or at least about 83, 84, 85, 86, 87, 88, 89, 90, 91, 92, 93, 94, 95, 96, 97, 98, or 99 percent sequence identity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some aspects, a nucleic acid has 100 percent sequence complementarity or at least about 83, 84, 85, 86, 87, 88, 89, 90, 91, 92, 93, 94, 95, 96, 97, 98, or 99 percent sequence complementarity when compared to a region of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some aspects, a nucleic acid has 100 percent sequence identity with or complementarity to one allele or one family member of a given target gene (coding or non-coding sequence of a gene). In some aspects, a nucleic acid has at least about 83, 84, 85, 86, 87, 88, 89, 90, 91, 92, 93, 94, 95, 96, 97, 98, or 99 percent sequence identity with or complementarity to multiple alleles or family members of a given target gene. In some aspects, a nucleic acid has 100 percent sequence identity with or complementarity to multiple alleles or family members of a given target gene.

In some aspects, the nucleic acid is essentially identical or essentially complementary to at least about 10, 15, 20, 25, 30, 35, 40, 45, 50, 55, 60, 65, 70 or more contiguous nucleotides of an endogenous calmodulin gene of a targeted pest, or an RNA transcribed therefrom. The nucleic acid may be a single-stranded DNA, a single-stranded RNA, a double-stranded RNA, a double-stranded DNA, or a double-stranded DNA/RNA hybrid. In some aspects, the calmodulin gene sequence is a *Varroa destructor* calmodulin gene sequence. In an aspect, the calmodulin gene sequence is a calmodulin gene sequence selected from SEQ ID NO: 1. In an aspect, the calmodulin gene sequence is a calmodulin gene sequence selected from SEQ ID NO: 2. In an aspect, the calmodulin gene sequence is a calmodulin gene sequence selected from SEQ ID NO: 3. In an aspect, the calmodulin gene sequence is a calmodulin gene sequence selected from SEQ ID NO: 4. In an aspect, the calmodulin gene sequence is a calmodulin gene sequence selected from SEQ ID NO: 69. In an aspect, the calmodulin gene sequence is a calmodulin gene sequence selected from SEQ ID NO: 70. In an aspect, the calmodulin gene sequence is a calmodulin gene sequence selected from SEQ ID NOs: 71-87. In an aspect, the calmodulin gene sequence is a calmodulin gene sequence selected from SEQ ID NO: 88. In an aspect, the calmodulin gene sequence is a calmodulin gene sequence selected from SEQ ID NO: 89.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. In an aspect according to the present disclosure, a composition may be used to treat an organism or colony of organisms for the effects of parasitation. In an aspect, a nucleic acid composition may be used to treat a host organism or colony for parasites. In an aspect, the host organism is a bee and the parasite is the mite, *Varroa destructor*.

As used herein, the phrase "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene or bee pathogen RNA sequence. RNA silencing has been observed in many types of organisms, including plants, animals, and fungi. In aspects according the present disclosure, nucleic acid compositions provide for RNA silencing. In certain aspects, the nucleic acid compositions provide for RNA silencing and mortality in a parasite.

As used herein, the term "RNA silencing agent" refers to a nucleic acid which is capable of inhibiting or "silencing" the expression of a target gene. In certain aspects, the RNA silencing agent is capable of preventing complete processing (e.g., the full translation and/or expression) of an mRNA molecule through a post-transcriptional silencing mechanism. RNA silencing agents can be single- or double-stranded RNA or single- or double-stranded DNA or double-stranded DNA/RNA hybrids or modified analogues thereof. In some aspects, the RNA silencing agents are selected from the group consisting of (a) a single-stranded RNA molecule (ssRNA), (b) a ssRNA molecule that self-hybridizes to form a double-stranded RNA molecule, (c) a double-stranded RNA molecule (dsRNA), (d) a single-stranded DNA molecule (ssDNA), (e) a ssDNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III promoter that is transcribed to an RNA molecule, (i) a double-stranded, hybridized RNA/DNA molecule, or combinations thereof. In some aspects these polynucleotides include chemically modified nucleotides or non-canonical nucleotides. In some aspects, the RNA silencing agents are noncoding RNA molecules, for example RNA duplexes comprising paired strands, as well as precursor RNAs from which such small non-coding RNAs can be generated. In some aspects, the RNA silencing agents are dsRNAs such as siRNAs, miRNAs and shRNAs. In one aspect, the RNA silencing agent is capable of inducing RNA interference. In another aspect, the RNA silencing agent is capable of mediating translational repression. In an aspect, the RNA silencing agent is capable of inhibiting the expression of a calmodulin gene. In another aspect, the RNA silencing agent is capable of being used in methods to inhibit the expression of a target gene and thereby kill a target organism. In certain aspects, the target gene is a calmodulin gene and the target organism is *Varroa destructor*.

RNA interference refers to the process of sequence-specific post-transcriptional gene silencing in animals mediated by small RNAs. The corresponding process in plants is commonly referred to as post-transcriptional gene silencing or RNA silencing and is also referred to as quelling in fungi. While not being limited to any particular theory, the process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. In aspects according to the present disclosure, a nucleic acid composition results in RNA interference in a target organism. In certain aspects, the nucleic acid composition results in RNA interference in *Varroa destructor* when present in the host organism, the bee. According to aspects of the present disclosure, a selective insecticide may cause RNA interference in the targeted organism, while having no RNA interference activity in non-target organisms.

As used herein, "small RNA" refers to any RNA molecule that is at least 15 base pairs in length, generally 15-30 nucleotides long, preferably 20-24 nucleotides long. In aspects according to the present disclosure, a "small RNA" is greater than 50 base pairs in length. In an aspect, the small RNA is greater than 50 base pairs in length but less than about 500 base pairs. In an aspect, the small RNA is greater than 100 base pairs in length but less than about 500 base pairs. In an aspect, the small RNA is greater than 200 base pairs in length but less than about 500 base pairs. A small RNA can be either double-stranded or single-stranded. Small RNA includes, without limitation, miRNA (microRNA), ta-siRNA (trans activating siRNA), siRNA, activating RNA (RNAa), nat-siRNA (natural anti-sense siRNA), hc-siRNA (heterochromatic siRNA), cis-acting siRNA, 1miRNA (long miRNA), 1siRNA (long siRNA) and easiRNA (epigenetically activated siRNA) and their respective precursors. In some embodiments, siRNA molecules of the disclosure are miRNA molecules, to-siRNA molecules and RNAa molecules and their respective precursors. A small RNA may be processed in vivo by an organism to an active form. According to aspects of the present disclosure, a selective insecticide may be a small RNA.

In aspects according to the present disclosure, a small RNA is provided directly in a composition. In other aspects, a small RNA is produced by in vivo by an organism from either a DNA or an RNA precursor. In some aspects, the small RNA is produced as a product of a transgene in an organism, for example a yeast or bacterial cell. In certain aspects, a small RNA produced as a product of a transgene is produced as a precursor that is processed in vivo after ingestion or absorption by an organism. In other aspects, a small RNA produced as a product of a transgene is produced as a precursor that is processed in vivo after ingestion or absorption by an organism.

In some aspects, the RNA silencing agent may be an artificial microRNA. As used herein, an "artificial microRNA" (amiRNA) is a type of miRNA which is derived by replacing native miRNA duplexes from a natural miRNA precursor. Generally, an artificial miRNA is a non-naturally-existing miRNA molecule produced from a pre-miRNA molecule scaffold engineered by exchanging a miRNA sequence of a naturally-existing pre-miRNA molecule for a sequence of interest which corresponds to the sequence of an artificial miRNA. In aspects according to the present disclosure a nucleic acid composition may be an amiRNA composition.

Various studies demonstrate that long dsRNAs can be used to silence gene expression without inducing the stress response or causing significant off-target effects—see for example (Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134). The present disclosure provides for, and includes, methods and compositions having long dsRNAs.

As used herein, with respect to a nucleic acid sequence, nucleic acid molecule, or a gene, the term "natural" or "native" means that the respective sequence or molecule is present in a wild-type organism, that has not been genetically modified or manipulated by man. A small RNA molecule naturally targeting a target gene means a small RNA molecule present in a wild-type organism, the cell has not been genetically modified or manipulated by man which is targeting a target gene naturally occurring in the respective organism.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

As used herein, the terms "exogenous polynucleotide" and "exogenous nucleic acid molecule" relative to an organisms refer to a heterologous nucleic acid sequence which is not naturally expressed within that organism. An exogenous nucleic acid molecule may be introduced into an organism in a stable or transient manner. An exogenous nucleic acid molecule may comprise a nucleic acid sequence which is identical or partially homologous to an endogenous nucleic acid sequence of the organism or a pest or pathogen of that organism. In certain aspects, an "exogenous polynucleotide" and "exogenous nucleic acid molecule" may refer to a parasite nucleic acid sequence expressed or present in a host, either transiently or stably. The present disclosure provides for, and includes, compositions comprising exogenous polynucleotides and exogenous nucleic acid molecules and methods for introducing them into a target organism. In some aspects, the present disclosure provides for, and includes, compositions comprising exogenous polynucleotides and exogenous nucleic acid molecules and methods for introducing them into a non-target organism that is a host to the target organism.

As used herein, a "control organism" means an organism that does not contain the recombinant DNA, small RNA, or other nucleic acid (e.g., protein, miRNA, small RNA-resistant target mRNA, dsRNA, target mimic) that provides for control of a pest or parasite. Control organisms are generally from same species and of the same developmental stage which is grown under the same growth conditions as the treated organism. Similarly, a "control colony" means a colony of organisms that do not contain the recombinant DNA, small RNA, or other nucleic acid (e.g., protein, miRNA, small RNA-resistant target mRNA, target mimic) that provides for control of a pest or parasite. Control colonies of organisms are generally from same species and of the same developmental stage which are grown under the same growth conditions as the treated colony of organisms. As a non-limiting example, a control organism could be a bee provided with a composition that does not contain a nucleic acid of the present disclosure. In another non-limiting example, a control organism could be a bee provided with a composition that contains a nucleic acid that does not act a an RNA silencer in either a bee or a parasite, such as SEQ ID NO: 5.

As used herein, the terms "improving," "improved," "increasing," and "increased" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase in an organism or colony population, in increased productivity of an organism or colony (e.g., increased honey productions), increase growth rate of an organism or colony, or increased reproductive rate as compared to a control organism or colony. The present disclosure provides for methods of improving the health of an organism or colony by providing a selective insecticidal composition.

As used herein, "a reduction" of the level of an agent such as a protein or mRNA means that the level is reduced relative to an organism or colony lacking a nucleic acid capable of reducing the agent. Also as used herein, "a reduction" in reference to parasitation or parasite load, means that the level is reduced relative to an organism or colony lacking a nucleic acid, such as a dsRNA molecule, capable of reducing the viability, fecundity or number of the parasite. The present disclosure provides for, and includes, methods and compositions for reducing the level of a protein or mRNA and reducing the level or number of parasites.

As used herein, the term "at least a partial reduction" of the level of an agent, such as a protein or mRNA, means that the level is reduced at least 25% relative to an organism or colony lacking a nucleic acid, such as a dsRNA molecule, capable of reducing the agent. Also as used herein, "at least a partial reduction" in reference to parasitation or parasite load, means that the level is reduced at least 25% relative to an organism or colony lacking a nucleic acid, such as a dsRNA molecule, capable of reducing the viability, fecundity or number of the parasite. The present disclosure provides for, and includes, methods and compositions for at least partially reducing the level of a protein or mRNA and at least partially reducing the level or number of parasites.

As used herein, "a substantial reduction" of the level of an agent such as a protein or mRNA means that the level is reduced relative to an organism or colony lacking a nucleic acid, such as a dsRNA molecule, capable of reducing the agent, where the reduction of the level of the agent is at least 75%. Also as used herein, "a substantial reduction" in reference to parasitation or parasite load, means that the level is reduced at least 75% relative to an organism or colony lacking a nucleic acid, such as a dsRNA molecule, capable of reducing the viability, fecundity or number of the parasite. The present disclosure provides for, and includes, methods and compositions for substantially reducing the level of a protein or mRNA and substantially reducing the level or number of parasites.

As used herein, "an effective elimination" of an agent such as a protein or mRNA is relative to an organism or colony lacking a dsRNA molecule capable of reducing the agent, where the reduction of the level of the agent is greater than 95%. An agent, such as a dsRNA molecule, is preferably capable of providing at least a partial reduction, more preferably a substantial reduction, or most preferably effective elimination of another agent such as a protein or mRNA, or a parasite, wherein the agent leaves the level of a second agent, or host organism, essentially unaffected, substantially unaffected, or partially unaffected. Also as used herein, "an effective elimination" in reference to parasitation or parasite load, means that the level is reduced at least 95% relative to an organism or colony lacking a nucleic acid, such as a dsRNA molecule, capable of reducing the viability, fecundity or number of the parasite. The present disclosure provides for, and includes, methods and compositions for the effective elimination of a protein or mRNA and effectively eliminating parasites.

As used herein, the terms "suppress," "repress," and "downregulate" when referring to the expression or activity of a nucleic acid molecule in an organism are used equivalently herein and mean that the level of expression or activity of the nucleic acid molecule in a cell of an organism after applying a method of the present disclosure is lower than its expression or activity in the cell of an organism before applying the method, or compared to a control organism lacking a nucleic acid molecule of the disclosure. The present disclosure provides for, and includes, methods and compositions for suppressing, repressing and down-regulating the level of a protein or mRNA and suppressing, repressing and down-regulating the level or number of parasites.

The terms "suppressed," "repressed" and "downregulated" as used herein are synonymous and mean herein lower, preferably significantly lower, expression or activity of a targeted nucleic acid molecule. Also as used herein, "suppressed," "repressed" and "downregulated" in reference to parasitation or parasite load, means that the level of parasitation or parasite load is lower, preferably significantly lower, relative to an organism or colony lacking a nucleic acid, such as a dsRNA molecule, capable of reducing the viability, fecundity or number of the parasite. The present disclosure provides for, and includes, methods and compositions for suppressing, repressing and down-regulating the expression or activity of a protein or mRNA and suppressing, repressing and down-regulating the activity of parasites.

As used herein, a "suppression," "repression," or "downregulation" of the level or activity of an agent such as a protein, mRNA, or RNA means that the level or activity is reduced relative to a substantially identical cell, organism or colony grown under substantially identical conditions, lacking a nucleic acid molecule of the disclosure, for example, lacking the region complementary to at least a part of the precursor molecule of a dsRNA or siRNA, the recombinant construct or recombinant vector of the disclosure. As used herein, "suppression," "repression," or "downregulation" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell, organism or colony lacking a recombinant nucleic acid molecule of the disclosure. The present disclosure provides for, and includes, methods and compositions for suppression, repression and downregulation of an agent such as a protein, mRNA, RNA, or parasite compared to an untreated organism or colony.

As used herein, the term "arthropod" refers to both adult and pupa of invertebrate animals having an exoskeleton (external skeleton), a segmented body, and jointed appendages. Arthropods are members of the phylum Arthropoda and includes the insects, arachnids, and crustaceans. Arthropods according to the present disclosure, include but are not limited to *Apis mellifera, Apis cerana, Trigona minima, Halictidae, Bombus* sp., fleas, flies, lice, ticks, mites, and beneficial insects. The present disclosure provides for, and includes, methods and compositions for treating arthropods as either a host or as a parasite or pest.

In an aspect, an arthropod may be an insect. In certain aspects, an insect may be a bee. As used herein, the term "bee" refers to both an adult bee and pupal cells thereof. According to one aspect, the bee is in a hive. An adult bee is defined as any of several winged, hairy-bodied, usually stinging insects of the superfamily Apoidea in the order Hymenoptera, including both solitary and social species and characterized by sucking and chewing mouthparts for gathering nectar and pollen. Examples of bee species include, but are not limited to, *Apis, Bombus, Trigona, Osmia* and the like. In one aspect, bees include, but are not limited to bumblebees (*Bombus terrestris*), honeybees (*Apis mellifera*) (including foragers and hive bees) and *Apis cerana*. The present disclosure provides for, and includes, methods and compositions for treating bees as a host for parasites, such as *Varroa* mites.

According to one aspect, a bee is part of a colony. The term "colony" refers to a population of bees comprising dozens to typically several tens of thousands of bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage. The present disclosure provides for, and includes, methods and compositions for treating insects colonies.

As used herein, the term "pest" refers to both adult and immature forms of an organism that is invasive or prolific, detrimental, troublesome, noxious, destructive, a nuisance to either plants or animals, or ecosystems. A parasite is a type of pest. It is possible for an organism to be a pest in one setting but beneficial, domesticated, or acceptable in another.

As used herein, the term "parasite" refers to both adult and immature forms of organisms that directly benefit at the expense of another, host, organism, for example by feeding on the blood or fluids of the host, living intracellularly in a host organism cell, or living within a body of a host organism. Parasites include organisms that are animals, fungi, bacterial or plants and are identified by their negative or detrimental interaction with a host. In some aspects, a parasite as used herein may in turn serve as a host to a second parasite. In some aspects, a parasite and host may be of the same type of organism (e.g., an arthropod host and an arthropod parasite). Parasites include, but are not limited to, *Acari* (ticks, mites), *Hippoboscoidea* (flies), *Ichneumonoidea* (parasitic wasps), *Oestridae* (bot flies), *Phthiraptera* (lice), *Siphonaptera* (fleas), *Tantulocarida*, Pea crab, and *Sacculina*. As used herein, a pest may include both parasitic and non-parasitic life stages. The present disclosure provides for, and includes, methods and compositions for treating parasites. In an aspect, the parasite may be *Varroa destructor*.

As provided for, and included, in the present disclosure, parasites and/or pests include *Varroa destructor, Ixodes scapularis, Solenopsis invicta, Tetranychus urticae, Aedes*

*aegypti, Culex quinquefasciatus, Acyrthosiphon pisum*, and *Pediculus humanus*. In aspects according to the present disclosure, selective insecticides may be selective for *Varroa destructor, Ixodes scapularis, Solenopsis invicta, Tetranychus urticae, Aedes aegypti, Culex quinquefasciatus, Acyrthosiphon pisum*, and *Pediculus humanus* and inactive, or significantly less active, against a non-target organisms, such as the host organism.

As used herein, the term “excipient” refers to any inactive substance in a formulation having an active ingredient such as an anti-parasitic, anti-pest or insecticidal nucleic acid, including without limitation dsRNA, small RNAs, miRNAs and antisense RNAs. In some embodiments, an excipient includes substances that may provide additional functionality to a composition that is distinct to the anti-parasitic, anti-pest, or insecticidal nucleic acids. Excipient functions include, but are not limited to “bulking agents,” “fillers,” “diluents,” and “carriers.” Bulking up allows convenient and accurate dispensation of compositions of the present disclosure. Excipients can also serve to facilitate ingestion of the compositions by organisms and include various carbohydrates, proteins, fatty acids, pollens, and pollen substitutes. Excipients can also serve to facilitate absorption of compositions by organisms an include, for example, both aqueous and non-aqueous solutions of active ingredients. Non-limiting examples of excipients include corn syrup, sugar syrup, sugar solid, sugar semi-solids, pollen, soy protein, pollen and protein mixtures. Excipients may further comprise attractants, buffers and nutrient supplements. Compositions of the present disclosure may be coated with, encapsulated in, dissolved in, mixed with, or otherwise combined with an excipient. As used herein, the term excipient may refer to a mixture of inactive substances.

This application provides and discloses anti-parasitic, anti-pest or insecticidal nucleic acid molecules that are substantially homologous or complementary to a polynucleotide sequence of a calmodulin target gene or an RNA expressed from the calmodulin target gene or a fragment thereof and functions to suppress the expression of the calmodulin target gene or produce a knock-down phenotype. The anti-parasitic, anti-pest or insecticidal nucleic acid molecules are capable of inhibiting or “silencing” the expression of a calmodulin target gene. These nucleic acid molecules are generally described in relation to their “target sequence.” In some embodiments, the target sequence is selected from SEQ ID NOs. 1, 2 and 6-77. The anti-parasitic, anti-pest or insecticidal nucleic acid molecules may be single-stranded DNA (ssDNA), single-stranded RNA (ssRNA), double-stranded RNA (dsRNA), double-stranded DNA (dsDNA), or double-stranded DNA/RNA hybrids. The nucleic acid molecules may comprise naturally-occurring nucleotides, modified nucleotides, nucleotide analogues or any combination thereof. In some embodiments, a anti-parasitic, anti-pest or insecticidal nucleic acid molecule may be incorporated within a larger polynucleotide, for example in a pri-miRNA molecule. In some embodiments, a anti-parasitic, anti-pest or insecticidal nucleic acid molecule may be processed into a small interfering RNA (siRNA). In some embodiments, nucleic acid molecules are provided or disclosed that are selectively anti-parasitical or miticidal, and methods of modulating expression or activity of their target genes to reduce or eliminate parasites from a colony or population.

In aspects according to the present disclosure, a anti-parasitic, anti-pest or insecticidal nucleic acid moleculecomprises a nucleotide sequence having at least 80%, 85%, 88%, 90%, 92%, 95%, 96%, 97%, 98%, or 99% sequence identity to a sequence or a portion of a sequence selected from the group consisting of SEQ ID NOs: 1 to 89. In certain aspects, the nucleic acid molecule is sleeted from the group consisting of ssDNA, ssRNA, dsRNA, dsDNA, or DNA/RNA hybrids. Several embodiments relate to a dsRNA comprising a nucleotide sequence having at least 80%, 85%, 88%, 90%, 92%, 95%, 96%, 97%, 98%, or 99% sequence identity to a sequence or a portion of a sequence selected from the group consisting of SEQ ID NOs: 1 to 89. In another aspect, a DNA encoding at least one nucleic acid, such as a ssRNA or dsRNA, comprises a nucleotide sequence or a portion of a nucleotide sequence selected from the group consisting of SEQ ID NOs: 1 to 89, or having at least 80%, 85%, 88%, 90%, 92%, 95%, 96%, 97%, 98%, or 99% sequence identity to SEQ ID NOs: 1 to 89 or a portion thereof is provided. In yet another aspect, a recombinant DNA encoding at least one nucleic acid, such as a ssRNA or dsRNA, comprises a nucleotide sequence or a portion of a nucleotide sequence selected from the group consisting of SEQ ID NOs: 1 to 89, a heterologous promoter and a transcription terminator sequence are provided. In another aspect, the present disclosure provides a recombinant DNA encoding at least one nucleic acid, such as a ssRNA or dsRNA, that comprises a nucleotide sequence having at least 80%, 85%, 88%, 90%, 92%, 95%, 96%, 97%, 98%, or 99% sequence identity to a sequence or a portion of a sequence selected from the group consisting of SEQ ID NOs: 1 to 89, and further comprising a heterologous promoter and a transcription terminator.

In aspects according to the present disclosure, a composition comprises an anti-parasitic, anti-pest or insecticidal nucleic acid molecule having 100 percent sequence identity to a region of 10 to 17 or more contiguous nucleotides in the target gene or RNA transcribed from the target gene. In an aspect, a composition comprises an anti-parasitic, anti-pest or insecticidal nucleic acid molecule having 100 percent sequence identity to a region of 18 to 25, or more contiguous nucleotides in the target gene or RNA transcribed from the target gene. In an aspect, a composition comprises an anti-parasitic, anti-pest or insecticidal nucleic acid molecule having 100 percent sequence identity to a region of 20 to 30, or more contiguous nucleotides in the target gene or RNA transcribed from the target gene. In an aspect, a composition comprises an anti-parasitic, anti-pest or insecticidal nucleic acid molecule having 100 percent sequence identity to a region of 25 to 35, or more contiguous nucleotides in the target gene or RNA transcribed from the target gene. In an aspect, a composition comprises an anti-parasitic, anti-pest or insecticidal nucleic acid molecule having 100 percent sequence identity to a region of 30 to 40, or more contiguous nucleotides in the target gene or RNA transcribed from the target gene. In an aspect, a composition comprises an anti-parasitic, anti-pest or insecticidal nucleic acid molecule having 100 percent sequence identity to a region of 40 to 50, or more contiguous nucleotides in the target gene or RNA transcribed from the target gene. In an aspect, a composition comprises an anti-parasitic, anti-pest or insecticidal nucleic acid molecule having 100 percent sequence identity to a region of 50 to 60, or more contiguous nucleotides in the target gene or RNA transcribed from the target gene. In an aspect, a composition comprises an anti-parasitic, anti-pest or insecticidal nucleic acid molecule having 100 percent sequence identity to a region of 45 to 60, or more contiguous nucleotides in the target gene or RNA transcribed from the target gene. In an aspect, a composition comprises an anti-parasitic, anti-pest or insecticidal nucleic acid molecule having 100 percent sequence identity to a region up to 60 contiguous nucleotides in the target gene or RNA transcribed from the target gene. In an aspect, a composition comprises an anti-parasitic, anti-pest or insecticidal nucleic acid molecule having 100 percent sequence identity to a region up to 50 contiguous nucleotides in the target gene or RNA transcribed from the target gene. In an aspect, a composition comprises an anti-parasitic, anti-pest or insecticidal nucleic acid molecule having 100 percent sequence identity to a region up to 40 contiguous nucleotides in the target gene or RNA transcribed from the target gene. In an aspect, a composition comprises an anti-parasitic, anti-pest or insecticidal nucleic acid molecule having 100 percent sequence identity to a region of at least 25 contiguous nucleotides in the target gene or RNA transcribed from the target gene. In an aspect, a composition comprises an anti-parasitic, anti-pest or insecticidal nucleic acid molecule having 100 percent sequence identity to a region of at least 35 contiguous nucleotides in the target gene or RNA transcribed from the target gene. In an aspect, a composition comprises an anti-parasitic, anti-pest or insecticidal nucleic acid molecule having 100 percent sequence identity to a region of at least 40 contiguous nucleotides in the target gene or RNA transcribed from the target gene. In an aspect, a composition comprises an anti-parasitic, anti-pest or insecticidal nucleic acid molecule having 100 percent sequence identity to a region of at least 50 contiguous nucleotides in the target gene or RNA transcribed from the target gene. In an aspect, a composition comprises an anti-parasitic, anti-pest or insecticidal nucleic acid molecule having 100 percent sequence identity to a region of at least 60 contiguous nucleotides in the target gene or RNA transcribed from the target gene. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 99 percent sequence identity to a region of 10 to 17 or more contiguous nucleotides in the target gene or RNA transcribed from the target gene. In an aspect, a composition comprises an anti-parasitic, anti-pest or insecticidal nucleic acid molecule having 99 percent sequence identity to a region of 18 to 25, or more contiguous nucleotides in the target gene or RNA transcribed from the target gene. In an aspect, a composition comprises an anti-parasitic, anti-pest or insecticidal nucleic acid molecule having 99 percent sequence identity to a region of 20 to 30, or more contiguous nucleotides in the target gene or RNA transcribed from the target gene. In an aspect, a composition comprises an anti-parasitic, anti-pest or insecticidal nucleic acid molecule having 99 percent sequence identity to a region of 25 to 35, or more contiguous nucleotides in the target gene or RNA transcribed from the target gene. In an aspect, a composition comprises an anti-parasitic, anti-pest or insecticidal nucleic acid molecule having 99 percent sequence identity to a region of 30 to 40, or more contiguous nucleotides in the target gene or RNA transcribed from the target gene. In an aspect, a composition comprises an anti-parasitic, anti-pest or insecticidal nucleic acid molecule having 99 percent sequence identity to a region of 40 to 50, or more contiguous nucleotides in the target gene or RNA transcribed from the target gene. In an aspect, an anti-parasitic, anti-pest or insecticidal composition comprises a nucleic acid molecule having 99 percent sequence identity to a region of 50 to 60, or more contiguous nucleotides in the target gene or RNA transcribed from the target gene. In an aspect, a composition comprises an anti-parasitic, anti-pest or insecticidal nucleic acid molecule having 99 percent sequence identity to a region of 45 to 60, or more contiguous nucleotides in the target gene or RNA transcribed from the target gene. In an aspect, a composition comprises an anti-parasitic, anti-pest or insecticidal nucleic acid molecule having 99 percent sequence identity to a region up to 60 contiguous nucleotides in the target gene or RNA transcribed from the target gene. In an aspect, a composition comprises an anti-parasitic, anti-pest or insecticidal nucleic acid molecule having 99 percent sequence identity to a region up to 50 contiguous nucleotides in the target gene or RNA transcribed from the target gene. In an aspect, a composition comprises an anti-parasitic, anti-pest or insecticidal nucleic acid molecule having 99 percent sequence identity to a region up to 40 contiguous nucleotides in the target gene or RNA transcribed from the target gene. In an aspect, a composition comprises an anti-parasitic, anti-pest or insecticidal nucleic acid molecule having 99 percent sequence identity to a region of at least 25 contiguous nucleotides in the target gene or RNA transcribed from the target gene. In an aspect, a composition comprises an anti-parasitic, anti-pest or insecticidal nucleic acid molecule having 99 percent sequence identity to a region of at least 35 contiguous nucleotides in the target gene or RNA transcribed from the target gene. In an aspect, a composition comprises an anti-parasitic, anti-pest or insecticidal nucleic acid molecule having 99 percent sequence identity to a region of at least 40 contiguous nucleotides in the target gene or RNA transcribed from the target gene. In an aspect, a composition comprises an anti-parasitic, anti-pest or insecticidal nucleic acid molecule having 99 percent sequence identity to a region of at least 50 contiguous nucleotides in the target gene or RNA transcribed from the target gene. In an aspect, a composition comprises an anti-parasitic, anti-pest or insecticidal nucleic acid molecule having 99 percent sequence identity to a region of at least 60 contiguous nucleotides in the target gene or RNA transcribed from the target gene. In some aspects, an anti-parasitic, anti-pest or insecticidal nucleic acid has at least 98 percent sequence identity to a region of the target gene. In an aspect, an anti-parasitic, anti-pest or insecticidal nucleic acid has at least 97 percent sequence identity to a region of the target gene. In some aspects, an anti-parasitic, anti-pest or insecticidal nucleic acid has at least 96 percent sequence identity to a region of the target gene. In an aspect, an anti-parasitic, anti-pest or insecticidal nucleic acid has at least 95 percent sequence identity to a region of the target gene. In some aspects, an anti-parasitic, anti-pest or insecticidal nucleic acid has at least 94 percent sequence identity to a region of the target gene. In an aspect, an anti-parasitic, anti-pest or insecticidal nucleic acid has at least 93 percent sequence identity to a region of the target gene. In some aspects, an anti-parasitic, anti-pest or insecticidal nucleic acid has at least 92 percent sequence identity to a region of the target gene. In an aspect, an anti-parasitic, anti-pest or insecticidal nucleic acid has at least 91 percent sequence identity to a region of the target gene. In an aspect, an anti-parasitic, anti-pest or insecticidal nucleic acid has at least about 83, 84, 85, 86, 87, 88, 89, 90 percent identity to a region of the target gene as provided above. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 100 percent sequence identity to a region of 10 to 17 or more contiguous nucleotides in to one allele or one family member of a given target gene (coding or non-coding sequence of a gene). In an aspect, a composition comprises an anti-parasitic, anti-pest or insecticidal nucleic acid molecule having 100 percent sequence identity to a region of 18 to 25, or more contiguous nucleotides to one allele or one family member of a given target gene). In an aspect, a composition comprises an anti-parasitic, anti-pest or insecticidal nucleic acid molecule having 100 percent sequence identity to a region of 20 to 30, or more contiguous nucleotides to one allele or one family member of a given target gene. In an aspect, a composition comprises an anti-parasitic, anti-pest or insecticidal nucleic acid molecule having 100 percent sequence identity to a region of 25 to 35, or more contiguous nucleotides to one allele or one family member of a given target gene. In an aspect, a composition comprises an anti-parasitic, anti-pest or insecticidal nucleic acid molecule having 100 percent sequence identity to a region of 30 to 40, or more contiguous nucleotides to one allele or one family member of a given target gene. In an aspect, a composition comprises an anti-parasitic, anti-pest or insecticidal nucleic acid molecule having 100 percent sequence identity to a region of 40 to 50, or more contiguous nucleotides to one allele or one family member of a given target gene. In an aspect, a composition comprises an anti-parasitic, anti-pest or insecticidal nucleic acid molecule having 100 percent sequence identity to a region of 50 to 60, or more contiguous nucleotides to one allele or one family member of a given target gene. In an aspect, a composition comprises an anti-parasitic, anti-pest or insecticidal nucleic acid molecule having 100 percent sequence identity to a region of 45 to 60, or more contiguous nucleotides to one allele or one family member of a given target gene. In an aspect, a composition comprises an anti-parasitic, anti-pest or insecticidal nucleic acid molecule having 100 percent sequence identity to a region up to 60 contiguous nucleotides to one allele or one family member of a given target gene. In an aspect, a composition comprises an anti-parasitic, anti-pest or insecticidal nucleic acid molecule having 100 percent sequence identity to a region up to 50 contiguous nucleotides to one allele or one family member of a given target gene. In an aspect, a composition comprises an anti-parasitic, anti-pest or insecticidal nucleic acid molecule having 100 percent sequence identity to a region up to 40 contiguous nucleotides to one allele or one family member of a given target gene. In an aspect, a composition comprises an anti-parasitic, anti-pest or insecticidal nucleic acid molecule having 100 percent sequence identity to a region of at least 25 contiguous nucleotides to one allele or one family member of a given target gene. In an aspect, a composition comprises an anti-parasitic, anti-pest or insecticidal nucleic acid molecule having 100 percent sequence identity to a region of at least 35 contiguous nucleotides to one allele or one family member of a given target gene. In an aspect, a composition comprises an anti-parasitic, anti-pest or insecticidal nucleic acid molecule having 100 percent sequence identity to a region of at least 40 contiguous nucleotides to one allele or one family member of a given target gene. In an aspect, a composition comprises an anti-parasitic, anti-pest or insecticidal nucleic acid molecule having 100 percent sequence identity to a region of at least 50 contiguous nucleotides to one allele or one family member of a given target gene. In an aspect, a composition comprises an anti-parasitic, anti-pest or insecticidal nucleic acid molecule having 100 percent sequence identity to a region of at least 60 contiguous nucleotides to one allele or one family member of a given target gene. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 99 percent sequence identity to a region of 10 to 17 or more contiguous nucleotides to one allele or one family member of a given target gene. In an aspect, a composition comprises an anti-parasitic, anti-pest or insecticidal nucleic acid molecule having 99 percent sequence identity to a region of 18 to 25, or more contiguous nucleotides to one allele or one family member of a given target gene. In an aspect, a composition comprises an anti-parasitic, anti-pest or insecticidal nucleic acid molecule having 99 percent sequence identity to a region of 20 to 30, or more contiguous nucleotides to one allele or one family member of a given target gene. In an aspect, a composition comprises an anti-parasitic, anti-pest or insecticidal nucleic acid molecule having 99 percent sequence identity to a region of 25 to 35, or more contiguous nucleotides to one allele or one family member of a given target gene. In an aspect, a composition comprises an anti-parasitic, anti-pest or insecticidal nucleic acid molecule having 99 percent sequence identity to a region of 30 to 40, or more contiguous nucleotides to one allele or one family member of a given target gene. In an aspect, a composition comprises an anti-parasitic, anti-pest or insecticidal nucleic acid molecule having 99 percent sequence identity to a region of 40 to 50, or more contiguous nucleotides to one allele or one family member of a given target gene. In an aspect, a composition comprises an anti-parasitic, anti-pest or insecticidal nucleic acid molecule having 99 percent sequence identity to a region of 50 to 60, or more contiguous nucleotides to one allele or one family member of a given target gene. In an aspect, a composition comprises an anti-parasitic, anti-pest or insecticidal nucleic acid molecule having 99 percent sequence identity to a region of 45 to 60, or more contiguous nucleotides to one allele or one family member of a given target gene. In an aspect, a composition comprises an anti-parasitic, anti-pest or insecticidal nucleic acid molecule having 99 percent sequence identity to a region up to 60 contiguous nucleotides to one allele or one family member of a given target gene. In an aspect, a composition comprises an anti-parasitic, anti-pest or insecticidal nucleic acid molecule having 99 percent sequence identity to a region up to 50 contiguous nucleotides to one allele or one family member of a given target gene. In an aspect, a composition comprises an anti-parasitic, anti-pest or insecticidal nucleic acid molecule having 99 percent sequence identity to a region up to 40 contiguous nucleotides to one allele or one family member of a given target gene. In an aspect, a composition comprises an anti-parasitic, anti-pest or insecticidal nucleic acid molecule having 99 percent sequence identity to a region of at least 25 contiguous nucleotides to one allele or one family member of a given target gene. In an aspect, a composition comprises an anti-parasitic, anti-pest or insecticidal nucleic acid molecule having 99 percent sequence identity to a region of at least 35 contiguous nucleotides to one allele or one family member of a given target gene. In an aspect, a composition comprises an anti-parasitic, anti-pest or insecticidal nucleic acid molecule having 99 percent sequence identity to a region of at least 40 contiguous nucleotides to one allele or one family member of a given target gene. In an aspect, a composition comprises an anti-parasitic, anti-pest or insecticidal nucleic acid molecule having 99 percent sequence identity to a region of at least 50 contiguous nucleotides to one allele or one family member of a given target gene. In an aspect, a composition comprises an anti-parasitic, anti-pest or insecticidal nucleic acid molecule having 99 percent sequence identity to a region of at least 60 contiguous nucleotides to one allele or one family member of a given target gene. In some aspects, an anti-parasitic, anti-pest or insecticidal nucleic acid has at least 98 percent sequence identity to a region of the target gene. In an aspect, an anti-parasitic, anti-pest or insecticidal nucleic acid has at least 97 percent sequence identity to a region of the target gene. In some aspects, an anti-parasitic, anti-pest or insecticidal nucleic acid has at least 96 percent sequence identity to a region of the target gene. In an aspect, an anti-parasitic, anti-pest or insecticidal nucleic acid has at least 95 percent sequence identity to a region of the target gene. In some aspects, an anti-parasitic, anti-pest or insecticidal nucleic acid has at least 94 percent sequence identity to a region of the target gene. In an aspect, an anti-parasitic, anti-pest or insecticidal nucleic acid has at least 93 percent sequence identity to a region of the target gene. In some aspects, an anti-parasitic, anti-pest or insecticidal nucleic acid has at least 92 percent sequence identity to a region of the target gene. In an aspect, an anti-parasitic, anti-pest or insecticidal nucleic acid has at least 91 percent sequence identity to a region of the target gene. In an aspect, an anti-parasitic, anti-pest or insecticidal nucleic acid has at least about 83, 84, 85, 86, 87, 88, 89, 90 percent identity to a region of the target gene as provided above. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 100 percent sequence identity to a region of 10 to 17 or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 18 to 25, or more contiguous nucleotides to one allele or one family member of a given target gene. In an aspect, a composition comprises an anti-parasitic, anti-pest or insecticidal nucleic acid molecule having 100 percent sequence identity to a region of 20 to 30, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 25 to 35, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 30 to 40, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 40 to 50, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 50 to 60, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of 45 to 60, or more contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 60 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 50 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region up to 40 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 25 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 35 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 40 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 50 contiguous nucleotides of identity with or complementarity to multiple alleles or family members of a given target gene. In an aspect, a composition comprises an anti-parasitic, anti-pest or insecticidal nucleic acid molecule having 100 percent sequence identity to a region of at least 60 contiguous nucleotides of identity with or complementarity to multiple alleles or family members of a given target gene. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs:6-68.

In aspects according to the present disclosure, a composition comprises an anti-parasitic, anti-pest or insecticidal nucleic acid molecule having 99 percent sequence identity to a region of 10 to 17 or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 18 to 25, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 20 to 30, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 25 to 35, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 30 to 40, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 40 to 50, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 50 to 60, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of 45 to 60, or more contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 60 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 50 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region up to 40 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 25 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 35 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 40 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 50 contiguous nucleotides of identity with or complementarity to multiple alleles or family members of a given target gene. In an aspect, a composition comprises an anti-parasitic, anti-pest or insecticidal nucleic acid molecule having 99 percent sequence identity to a region of at least 60 contiguous nucleotides of identity with or complementarity to multiple alleles or family members of a given target gene. In some aspects, an anti-parasitic, anti-pest or insecticidal nucleic acid has at least 98 percent sequence identity to a region of a target gene. In an aspect, an anti-parasitic, anti-pest or insecticidal nucleic acid has at least 97 percent sequence identity to a region of a target gene. In some aspects, an anti-parasitic, anti-pest or insecticidal nucleic acid has at least 96 percent sequence identity to a region of a target gene. In an aspect, an anti-parasitic, anti-pest or insecticidal nucleic acid has at least 95 percent sequence identity to a region of a target gene. In some aspects, an anti-parasitic, anti-pest or insecticidal nucleic acid has at least 94 percent sequence identity to a region of a target gene. In an aspect, an anti-parasitic, anti-pest or insecticidal nucleic acid has at least 93 percent sequence identity to a region of a target gene. In some aspects, an anti-parasitic, anti-pest or insecticidal nucleic acid has at least 92 percent sequence identity to a region of a target gene. In an aspect, an anti-parasitic, anti-pest or insecticidal nucleic acid has at least 91 percent sequence identity to a region of a target gene. In an aspect, an anti-parasitic, anti-pest or insecticidal nucleic acid has at least about 83, 84, 85, 86, 87, 88, 89, 90 percent identity to a region of a target gene as provided above. In an aspect, a target gene may be a gene comprising SEQ ID NO: 1 to 89. In an aspect, a target gene may be a gene comprising SEQ ID NO: 1. In an aspect, a target gene may be a gene comprising SEQ ID NO: 2. In an aspect, a target gene may be a gene comprising SEQ ID NO: 3. In an aspect, a target gene may be a gene comprising SEQ ID NO: 4. In an aspect, a target gene may be a gene comprising SEQ ID NO: 69. In an aspect, a target gene may be a gene comprising SEQ ID NO: 70. In an aspect, a target gene may be a gene comprising SEQ ID NO: 88. In an aspect, a target gene may be a gene comprising SEQ ID NO: 89. In an aspect, a target gene may be a gene comprising a sequence selected from SEQ ID NOs:71-87. In an aspect, a target gene may be a gene comprising a sequence selected from SEQ ID NOs: 6-68.

This application provides and discloses compositions comprising an anti-parasitic, anti-pest or insecticidal nucleic acid molecule and an excipient substance. In an aspect, the excipient can be a combination of one or more inactive components. In some aspects, the excipient comprises a sugar. Exemplary sugars include hexoses, disaccharides, trisaccharides and higher sugars. Excipient sugars include, for example, fructose, glucose, sucrose, trehalose, lactose, galactose, ribose. In other aspects the excipient comprises a sugar and a solvent. In other aspects, the excipient comprises a protein. In an aspect, the protein is a soy protein. In other aspects the excipient may be pollen. In aspects according to the present disclosure, the excipient may be a bee food. In some aspects, the excipient comprises Tryptone. In some aspects, the excipient comprises yeast extract. In some aspects, the excipient comprises an essential oil.

Bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to percent pollen improves the quality and quantity of essential nutrients that are required by bees for vital activity. Cane or beet sugar, isomerized corn syrup, and type-50 sugar syrup are satisfactory substitutes for honey in the natural diet of honey bees. The last two can be supplied only as a liquid to bees. Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one aspect, pan or trays in which floating supports-such as wood chips, cork, or plastic sponge-are present are envisaged. Detailed descriptions of supplemental feeds for bees can be found in, for example, USDA publication by Standifer, et al. 1977, entitled "Supplemental Feeding of Honey Bee Colonies" (USDA, Agriculture Information Bulletin No. 413).

In aspects according to the present disclosure, an anti-parasitic, anti-pest or insecticidal nucleic acid, for example a dsRNA, is absorbable. As used herein "absorbable," refers to mechanisms the provide for the uptake of a nucleic acid that is not by ingestion. In an aspect, an anti-parasitic, anti-pest or insecticidal nucleic acid may be absorbed through the skin of an organism, or the exoskeleton of an arthropod. In an aspect, an absorbable nucleic acid is dissolved in an excipient. In other aspects, an absorbable nucleic acid is suspended in an excipient. Excipients for solvation or suspension may be aqueous or non-aqueous. In some aspects, the anti-parasitic, anti-pest or insecticidal nucleic acid is absorbed by a host organism and transferred to a parasitic organism by feeding. In other aspects, the anti-parasitic, anti-pest or insecticidal nucleic acid is absorbed by a host organism and transferred to a parasitic organism by absorption. In an aspect, an anti-parasitic, anti-pest or insecticidal nucleic acid of the present disclosure is absorbed directly by the parasite.

In aspects according to the present disclosure an anti-parasitic, anti-pest or insecticidal nucleic acid, for example a dsRNA, is combined with an excipient. In an aspect, the nucleic acid may be provided as a ratio of nucleic acid to excipient. In an aspect, the ratio may be one part nucleic acid to 4 parts excipient. In an aspect the ratio of nucleic acid to excipient may be 1:1, 1:2, 1:5, or 1:10. In other aspects, the ratio of nucleic acid to excipient may be 1:20, 1:25, 1:30, 1:40, or more. In an aspect, ratio of nucleic acid to excipient may be 1:50. In aspects according to the present disclosure, the ratio may be determined as a volume to volume (v/v) ratio, a weight:weight (w/w) ratio. In certain aspects, the ratio may be expressed as a weight:volume (w/v) ratio. In certain aspects, a nucleic acid and an excipient may be a dsRNA and an excipient.

In aspects according to the present disclosure, the composition may comprise a weight of an anti-parasitic, anti-pest or insecticidal nucleic acid combined with an excipient. In an aspect, the nucleic acid may comprise a percentage of the total weight of the composition. In an aspect, the nucleic acid may comprise about 0.1% by weight of the composition. In an aspect, the nucleic acid may comprise about 0.2% by weight of the composition. In an aspect, the nucleic acid may comprise about 0.3% by weight of the composition. In another aspect, the nucleic acid may comprise about 0.4% by weight of the composition. In an aspect, the nucleic acid may comprise up to 0.5% by weight of the composition. In an aspect, the nucleic acid may comprise up to 0.6% by weight of the composition. In an aspect, the nucleic acid may comprise up to 0.7% by weight of the composition. In an aspect, the nucleic acid may comprise up to 0.8% by weight of the composition. In another aspect, the nucleic acid may comprise up to 1.0% by weight of the composition. In other aspects, the nucleic acid may comprise up to 1.5% by weight of the composition. In yet other aspects, the nucleic acid may comprise up to 2.0% by weight, or 2.5% by weight of the composition. In certain aspects, a nucleic acid and an excipient may be a dsRNA and an excipient.

The present disclosure provides for, and includes, compositions having from 0.1% to 5% by weight of one or more anti-parasitic, anti-pest or insecticidal nucleic acids. In other aspects, a composition may comprise from 0.1 to 4%, 0.1 to 3%, 0.1 to 2%, 0.1 to 1%, 0.1 to 2%, 0.1 to 3%, or 0.1 to 4% by weight nucleic acid. In an aspect, a composition may comprise from 0.2% to 5% by weight nucleic acid. In other aspects, a composition may comprise from 0.2 to 4%, 0.2 to 3%, 0.2 to 2%, 0.2 to 1%, 0.2 to 2%, 0.2 to 3%, or 0.2 to 4% by weight nucleic acid. In other aspects, a composition may comprise up to 1%, up to 2%, up to 3%, up to 4%, or up to 5% nucleic acid. In other aspects, a composition may comprise up to 7.5%, up to 10%, or up to 15% nucleic acid. In certain aspects, a nucleic acid and an excipient may be a dsRNA and an excipient.

The present disclosure provides for, and includes, compositions having from 0.1 to 10 mg/ml of one ore more anti-parasitic, anti-pest or insecticidal nucleic acids. In other aspects, a composition may comprise from 0.1 to 1.0 mg/ml, 0.1 to 2.0 mg/ml, 0.1 to 2.5 mg/ml, 0.1 to 5 mg/ml, 0.1 to 10 mg/ml, 0.1 to 15 mg/ml, or 0.1 to 20 mg/ml nucleic acid. In certain aspects, a composition may comprise at least 0.1 μg/ml nucleic acid. In certain other aspects, a composition may comprise at least 1.0 μg/ml nucleic acid. In yet other aspects, a composition may comprise at least 10 μg/ml nucleic acid. In an aspect, a composition may comprise from 0.5 to 10 mg/ml nucleic acid. In other aspects, a composition may comprise from 0.5 to 1.0 mg/ml, 0.5 to 2.0 mg/ml, 0.5 to 2.5 mg/ml, 0.5 to 5 mg/ml, 0.5 to 10 mg/ml, 0.5 to 15 mg/ml, or 0.5 to 20 mg/ml nucleic acid. In an aspect, a composition may comprise from 1.0 to 10 mg/ml nucleic acid. In other aspects, a composition may comprise from 1.0 to 2.0 mg/ml, 1.0 to 2.5 mg/ml, 1.0 to 5 mg/ml, 1.0 to 10 mg/ml, 1.0 to 15 mg/ml, or 1.0 to 20 mg/ml nucleic acid. In certain aspects, the anti-parasitic, anti-pest or insecticidal nucleic acid in the composition comprises a dsRNA.

The present disclosure, provides for, and includes selective insecticide compositions and methods of using selective insecticide compositions.

As used herein, a "selective insecticide composition," is a composition that is more effective for one or more arthropod species and is less effective for one or more different arthropod species. A selective insecticide composition includes compositions that kill adults or immature arthropods and includes compositions that are larvicides and ovicides. A selective insecticide may be a systemic insecticides incorporated by treated food, including the blood or hemolymph obtained from a host organisms. A selective insecticide may be a contact insecticides are toxic to certain insects brought into direct contact, and are non-toxic or minimally toxic to certain other insects. In some embodiments, a selective insecticide composition is anti-pest. In some embodiments, a selective insecticide composition is anti-parasitic. In some embodiments, a selective insecticide composition is a miticide. In some embodiments, a selective insecticide composition is toxic to a targeted parasitic or pest insect and non-toxic or minimally toxic to non-target organisms. Examples of non-target organisms include, but are not limited to beneficial insects, nematodes, birds, mammals, and plants. In some embodiments, a selective insecticide composition is toxic to a parasitic insect, for example *Varroa* mite, and non-toxic or minimally toxic to the host organism, for example bees. In some embodiments, a selective insecticide composition is toxic to one or more pest or parasitic insects selected from the group consisting of: *Varroa destructor, Ixodes scapularis, Solenopsis invicta, Tetranychus urticae, Aedes aegypti, Culex quinquefasciatus, Acyrthosiphon pisum*, and *Pediculus humanus*.

In certain aspects according to the present disclosure, a selective insecticide may be incorporated into a bacteria or yeast by genetic modification (for example, a transgenic bacteria or yeast engineered to express a nucleic acid of the present disclosure). A selective insecticide introduced by genetic modification of a bacteria or yeast may act directly on the pest organism, or indirectly by being ingested by a host of the pest organism.

In an aspect according to the present disclosure, a selective insecticide may be a more effective insecticide against one or more first insects than against one or more second insects. In an aspect, a selective insecticide may be toxic to a first insect and have no effect on a second insect. In an aspect, a selective insecticide may be toxic to a first insect and require significantly higher concentrations or amounts to have an effect on a second insect. In an aspect, a selective insecticide may be 2 times or more toxic to a first insect compared to a second insect. In an aspect, a selective insecticide may be 4 times or more toxic to a first insect compared to a second insect. In an aspect, a selective insecticide may be 5 times or more toxic to a first insect compared to a second insect. In an aspect, a selective insecticide may be 10 times or more toxic to a first insect compared to a second insect.

In an aspect, a selective insecticide may inhibit the growth, development or fecundity of a first insect and have no effect on a second insect. In an aspect, a selective insecticide may inhibit the growth, development or fecundity a first insect and require significantly higher concentrations or amounts to have a similar effect on a second insect. In an aspect, a selective insecticide may require 2 times or more of the active ingredient to inhibit the growth, development or fecundity of a second insect. In an aspect, a selective insecticide may require 4 times or more of the active ingredient to inhibit the growth, development or fecundity of a second insect. In an aspect, a selective insecticide may require 5 times or more of the active ingredient to inhibit the growth, development or fecundity of a second insect. In an aspect, a selective insecticide may require 10 times or more of the active ingredient to inhibit the growth, development or fecundity of a second insect.

The present disclosure further includes, and provides for, methods of treating or preventing Colony Collapse Disorder in a honeybee colony, comprising providing an effective amount of a composition comprising a nucleic acid that is essentially identical or essentially complementary to a region of a *Varroa destructor* calmodulin gene sequence to a honeybee whereby the level of *Varroa destructor* infestation is reduced. In an aspect, the method comprises providing an effective amount of a composition comprising a nucleic acid that is essentially identical or essentially complementary to at least 19 contiguous nucleotides of SEQ ID NO: 1. In an aspect, the method comprises providing an effective amount of a composition comprising a nucleic acid that is essentially identical or essentially complementary to at least 19 contiguous nucleotides of SEQ ID NO: 2. In an aspect, the method comprises providing an effective amount of a composition comprising a nucleic acid that is essentially identical or essentially complementary to at least 19 contiguous nucleotides of SEQ ID NO: 69. In an aspect, the method comprises providing an effective amount of a composition comprising a nucleic acid that is essentially identical or essentially complementary to at least 19 contiguous nucleotides of SEQ ID NO: 70. In an aspect, the method comprises providing an effective amount of a composition comprising a nucleic acid according to SEQ ID NO: 3. In an aspect, the method comprises providing an effective amount of a composition comprising a nucleic acid according to SEQ ID NO: 4. In an aspect, the method comprises providing an effective amount of a composition comprising a nucleic acid according to SEQ ID NO: 88. In an aspect, the method comprises providing an effective amount of a composition comprising a nucleic acid according to SEQ ID NO: 89. In an aspect, the method comprises providing an effective amount of a composition comprising two or more nucleic acids having a sequence selected from the group consisting of: SEQ ID NOs: 3, 4, 88 and 89. In an aspect, the method comprises providing an effective amount of a composition comprising a nucleic acid that is essentially identical or essentially complementary to at least 19 contiguous nucleotides of a sequence selected from SEQ ID NOs:

71-87. In an aspect, the method comprises providing an effective amount of a composition comprising a nucleic acid that is essentially identical or essentially complementary to at least 23 contiguous nucleotides of a sequence selected from SEQ ID NOs: 71-87. In an aspect, the method comprises providing an effective amount of a composition comprising a nucleic acid that is essentially identical or essentially complementary to at least 30 contiguous nucleotides of a sequence selected from SEQ ID NOs: 71-87. In an aspect, the method comprises providing an effective amount of a composition comprising a nucleic acid that is essentially identical or essentially complementary to at least 40 contiguous nucleotides of a sequence selected from SEQ ID NOs: 71-87. In an aspect, the method comprises providing an effective amount of a composition comprising a nucleic acid that is essentially identical or essentially complementary to at least 50 contiguous nucleotides of a sequence selected from SEQ ID NOs: 71-87. In an aspect, the method comprises providing an effective amount of a composition comprising a nucleic acid that is essentially identical or essentially complementary to at least 60 contiguous nucleotides of a sequence selected from SEQ ID NOs: 71-87. In an aspect, the method comprises providing an effective amount of a composition comprising a nucleic acid that is essentially identical or essentially complementary to at least 70 contiguous nucleotides of a sequence selected from SEQ ID NOs: 71-87. In an aspect, the method comprises providing an effective amount of a composition comprising a nucleic acid that is essentially identical or essentially complementary to at least 80 contiguous nucleotides of a sequence selected from SEQ ID NOs: 71-87. In an aspect, the method comprises providing an effective amount of a composition comprising a nucleic acid that is essentially identical or essentially complementary to at least 90 contiguous nucleotides of a sequence selected from SEQ ID NOs: 71-87. In an aspect, the method comprises providing an effective amount of a composition comprising a nucleic acid that is essentially identical or essentially complementary to at least 100 contiguous nucleotides of a sequence selected from SEQ ID NOs: 71-87. In an aspect, the method comprises providing an effective amount of a composition comprising a nucleic acid that is essentially identical or essentially complementary to at least 110 contiguous nucleotides of a sequence selected from SEQ ID NOs: 71-87. In an aspect, the method comprises providing an effective amount of a composition comprising a nucleic acid that is essentially identical or essentially complementary to at least 120 contiguous nucleotides of a sequence selected from SEQ ID NOs: 71-87. In an aspect, the method comprises providing an effective amount of a composition comprising a nucleic acid that is essentially identical or essentially complementary to at least 130 contiguous nucleotides of a sequence selected from SEQ ID NOs: 71-87. In an aspect, the method comprises providing an effective amount of a composition comprising a nucleic acid that is essentially identical or essentially complementary to at least 140 contiguous nucleotides of a sequence selected from SEQ ID NOs: 71-87. In an aspect, the method comprises providing an effective amount of a composition comprising a nucleic acid that is essentially identical or essentially complementary to a sequence selected from SEQ ID NOs: 71-87. In an aspect, the method comprises providing an effective amount of a composition comprising a nucleic acid according to a sequence selected from SEQ ID NOs: 71-87.

The present disclosure provides for, and includes, methods for reducing the parasite load of a host organism. In an aspect, the parasite load refers to the number of parasites per individual host. In an aspect, the parasite load refers to the average number of parasites per 100 host organisms. In an aspect, the parasite load may refer to the number of parasites per colony of parasite hosts. In aspects according to the present disclosure the parasite is *Varroa destructor* and the host is the honey bee, *Apis mellifera*. In certain aspects, the parasite load refers to the number of *Varroa destructor* parasites per 100 honeybees in a colony. In some embodiments, the present disclosure provides for, and includes, methods and compositions for reducing the parasite load to less than 6 *Varroa destructor* parasites per 100 honeybees in a colony. In some embodiments, the present disclosure provides for, and includes, methods and compositions for reducing the parasite load to less than 5 *Varroa destructor* parasites per 100 honeybees in a colony. In some embodiments, the present disclosure provides for, and includes, methods and compositions for reducing the parasite load to less than 4 *Varroa destructor* parasites per 100 honeybees in a colony. In some embodiments, the present disclosure provides for, and includes, methods and compositions for reducing the parasite load to less than 2 *Varroa destructor* parasites per 100 honeybees in a colony.

In an aspect, the methods of reducing a parasite load comprises providing an effective amount of an anti-parasitic, anti-pest or insecticidal nucleic acid composition to a host organism. An effective amount of a composition of the present disclosure results in a decrease in the parasite load over a period of time. In an aspect, a decrease in parasite load may measured within one day of providing an effective amount of a nucleic acid composition. In an aspect, the parasite load may be measured after two days. In an aspect, the parasite load may be measured after 3 days. In other aspects, the parasite load may be measured after 5 days or after 1 week. In another aspect, the parasite load may be measured more than one time, for example every 3 days, every 5 days, every week or once a month. In certain aspects, according to the present disclosure, a decrease in the number of parasites may be measured and compared to an untreated control organism or colony. In aspects according to the present disclosure the parasite is *Varroa destructor* and the host is the honey bee, *Apis mellifera*.

In aspects according to the present disclosure, a reduction in parasite load after a period of time means a decrease in the number of parasites. In an aspect, the number of parasites may decrease by 10%, 20%, 30% or more between measurements. In another aspect, the number of parasites may decrease by 40% or more between measurements. In another aspect, the number of parasites may decrease by 50% or more between measurements. In another aspect, the number of parasites may decrease by 60% or more between measurements. In another aspect, the number of parasites may decrease by 70% or more between measurements. In another aspect, the number of parasites may decrease by 80% or more between measurements. In another aspect, the number of parasites may decrease by 90% or more between measurements.

In other aspects, the parasite load may be measured as the average number of parasites per host organism. In an aspect, a decreased parasitic load may comprise fewer than 20 parasites per 100 host organisms. In an aspect, a decreased parasitic load may comprise fewer than 15 parasites per 100 host organisms. In an aspect, a decreased parasitic load may comprise fewer than 10 parasites per 100 host organisms. In an aspect, a decreased parasitic load may comprise fewer than 5 parasites per 100 host organisms. In an aspect, a decreased parasitic load may comprise fewer than 4 parasites per 100 host organisms. In an aspect, a decreased parasitic load may comprise fewer than 3 parasites per 100 host organisms. In an aspect, a decreased parasitic load may comprise fewer than 2 parasites per 100 host organisms. In an aspect, a decreased parasitic load may comprise fewer than 1 parasite per 100 host organisms. In an aspect, a decreased parasitic load may comprise fewer than 20 parasites per 1000 host organisms. In an aspect, a decreased parasitic load may comprise fewer than 15 parasites per 1000 host organisms. In an aspect, a decreased parasitic load may comprise fewer than 10 parasites per 1000 host organisms. In an aspect, a decreased parasitic load may comprise fewer than 5 parasites per 1000 host organisms. In an aspect, a decreased parasitic load may comprise fewer than 4 parasites per 1000 host organisms. In an aspect, a decreased parasitic load may comprise fewer than 3 parasites per 1000 host organisms. In an aspect, a decreased parasitic load may comprise fewer than 2 parasites per 1000 host organisms. In an aspect, a decreased parasitic load may comprise fewer than 1 parasite per 1000 host organisms.

In aspects according to the present disclosure, a colony of host organisms has an initial parasite load, prior to being provided a source of an effective amount of a nucleic acid. In an aspect, an initial parasite load may comprise fewer than 20 parasites per 100 host organisms. In an aspect, an initial parasite load may comprise fewer than 15 parasites per 100 host organisms. In an aspect, an initial parasite load may comprise fewer than 10 parasites per 100 host organisms. In an aspect, an initial parasite load may comprise fewer than 5 parasites per 100 host organisms.

In an aspect, an initial parasite load may comprise fewer than 4 parasites per 100 host organisms. In an aspect, an initial parasite load may comprise fewer than 3 parasites per 100 host organisms. In an aspect, an initial parasite load may comprise fewer than 2 parasites per 100 host organisms. In an aspect, an initial parasite load may comprise fewer than 1 parasite per 100 host organisms.

In aspects according to the present disclosure, an effective amount may be provided periodically or continually. In an aspect, an effective amount of an anti-parasitic, anti-pest or insecticidal nucleic acid composition may be provided once, twice or three times a day. In other aspects, an effective amount of an anti-parasitic, anti-pest or insecticidal nucleic acid composition may be provided once a day. In another aspect, an effective amount of an anti-parasitic, anti-pest or insecticidal nucleic acid composition may be provided one or more times every other day. In an aspect, an effective amount of an anti-parasitic, anti-pest or insecticidal nucleic acid composition may be provided every two days, every three days, or once a week. In an aspect, an effective amount of an anti-parasitic, anti-pest or insecticidal nucleic acid composition may be provided every two weeks. In an aspect, an effective amount of an anti-parasitic, anti-pest or insecticidal nucleic acid composition may be provided every three weeks. In an aspect, an effective amount of an anti-parasitic, anti-pest or insecticidal nucleic acid composition may be provided once a month. In an aspect, an effective amount of an anti-parasitic, anti-pest or insecticidal nucleic acid composition may be provided every two months. In an aspect, an effective amount of a nucleic acid composition may be provided continuously to an organism in need, for example by providing a continuous source of food. In one aspect, an effective amount of a nucleic acid composition may be provided continuously as a bee-ingestible composition. In aspects according to the present disclosure the parasite is *Varroa destructor* and the host is the honey bee, *Apis mellifera*. In aspects according to the present disclosure, an anti-parasitic, anti-pest or insecticidal nucleic acid may be a dsRNA.

In aspects according to the present disclosure, the parasitic load may decrease over a period of time. In an aspect, the time period necessary for a parasitic load decrease may be 15 weeks. In another aspect, the time period for a parasitic load decrease may be 12 weeks. In an aspect, the parasitic load decrease occurs of a period of 10 weeks. In an aspect, the time period necessary for a parasitic load decrease may be 5 weeks. In another aspect, the time period for a parasitic load decrease may be 2 weeks. In an aspect, the parasitic load decrease occurs of a period of 1 weeks. In some aspects, the parasitic load may decrease after one day, two days or three days.

The present disclosure provides for methods of reducing the parasitation of a honey bee colony comprising providing a bee colony an effective amount of an anti-parasitic, anti-pest or insecticidal nucleic acid composition. An effective amount of a composition of the present disclosure results in a reduction of parasitation over a period of time. In an aspect, a reduction of parasitation may measured within one day of providing an effective amount of an anti-parasitic, anti-pest or insecticidal nucleic acid composition. In an aspect, the reduction of parasitation may be measured after two days. In an aspect, the reduction of parasitation may be measured after 3 days. In other aspects, the reduction of parasitation may be measured after 5 days or after 1 week. In another aspect, the reduction of parasitation may be measured more than one time, for example every 3 days, every 5 days, every week or once a month. In certain aspects, according to the present disclosure, a reduction of parasitation may be measured and compared to an untreated control organism or colony.

In aspects according to the present disclosure, a reduction of parasitation after a period of time means a decrease in the total number of parasites. In an aspect, the number of parasites may decrease by 10%, 20%, 30% or more between measurements. In another aspect, the number of parasites may decrease by 40% or more between measurements. In another aspect, the number of parasites may decrease by 50% or more between measurements. In another aspect, the number of parasites may decrease by 60% or more between measurements. In another aspect, the number of parasites may decrease by 70% or more between measurements. In another aspect, the number of parasites may decrease by 80% or more between measurements. In another aspect, the number of parasites may decrease by 90% or more between measurements.

In other aspects, reduction of parasitation may be measured as the average number of parasites per host organism. In an aspect, a reduction of parasitation may comprise fewer than 20 parasites per 100 host organisms. In an aspect, a reduction of parasitation may comprise fewer than 15 parasites per 100 host organisms. In an aspect, a reduction of parasitation may comprise fewer than 10 parasites per 100 host organisms. In an aspect, a reduction of parasitation may comprise fewer than 5 parasites per 100 host organisms. In an aspect, a reduction of parasitation may comprise fewer than 4 parasites per 100 host organisms. In an aspect, a reduction of parasitation may comprise fewer than 3 parasites per 100 host organisms. In an aspect, a reduction of parasitation may comprise fewer than 2 parasites per 100 host organisms. In an aspect, a reduction of parasitation may comprise fewer than 1 parasite per 100 host organisms.

In aspects according to the present disclosure, an effective amount of an anti-parasitic, anti-pest or insecticidal nucleic acid resulting in a reduction of parasitation may be provided periodically or continually. In an aspect, an effective amount of a nucleic acid composition may be provided once, twice or three times a day. In other aspects, an effective amount of an anti-parasitic, anti-pest or insecticidal nucleic acid composition may be provided once a day. In another aspect, an effective amount of an anti-parasitic, anti-pest or insecticidal nucleic acid composition may be provided one or more times every other day. In an aspect, an effective amount of an anti-parasitic, anti-pest or insecticidal nucleic acid composition may be provided provide every two days, every three days, or once a week. In an aspect, an effective amount of an anti-parasitic, anti-pest or insecticidal nucleic acid composition may be provided continuously to an organism in need, for example by providing a continuous source of food. In one aspect, an effective amount of an anti-parasitic, anti-pest or insecticidal nucleic acid composition may be provided continuously as a bee-ingestible composition. In aspects according to the present disclosure the parasite is *Varroa destructor* and the host is the honey bee, *Apis mellifera*. In aspects according to the present disclosure, an anti-parasitic, anti-pest or insecticidal nucleic acid may be a dsRNA.

In aspects according to the present disclosure, the reduction of parasitation may decrease over a period of time. In an aspect, the time period necessary for a reduction of parasitation may be 15 weeks. In another aspect, the time period for a reduction of parasitation may be 12 weeks. In an aspect, the reduction of parasitation occurs of a period of 10 weeks. In an aspect, the time period necessary for a reduction of parasitation may be 5 weeks. In another aspect, the time period for a reduction of parasitation may be 2 weeks. In an aspect, the reduction of parasitation occurs of a period of 1 weeks. In some aspects, the reduction of parasitation may occur after one day, two days or three days.

In aspects according to the present disclosure, a reduction of parasitation is measured by the number of surviving parasites as compared to an initial measurement of the number of parasites in a colony of host organisms. In an aspect, the parasite may be a *Varroa destructor* mite and the host may be a honey bee, *Apis mellifera*. In an aspect, the number of surviving parasites may be 25% of the initial number of parasites. In an aspect, the number of surviving parasites may be 15% of the initial number of parasites. In an aspect, the number of surviving parasites may be 10% of the initial number of parasites. In an aspect, the number of surviving parasites may be 5% of the initial number of parasites. In an aspect the number of surviving parasites may be less than 5% or even undetectable after providing a host colony an effective amount of an anti-parasitic, anti-pest or insecticidal nucleic acid composition.

In an aspect, the present disclosure provides for methods and compositions for reducing the susceptibility of bees to *Varroa* mite infestation. In other aspects, the present disclosure provides for methods and compositions to prevent the infestation of colonies of bees. In another aspect, the present disclosure provides methods and compositions for reducing the parasitation of honeybees by the mite *Varroa destructor.*

According to the present disclosure, a host organism provided with a source of an anti-parasitic, anti-pest or insecticidal nucleic acid, can accumulate nucleic acid in the host body, usually the hemolymph. By harboring nucleic acid, such host organisms become resistant, or less susceptible to parasitation. In other aspects, a colony of host organisms, provided with a source of nucleic acid, can accumulate nucleic acid in the host body of multiple members of the colony, thereby providing resistance or decreased susceptibility to a parasite. nucleic acid found in host organisms provided with a source of nucleic acid, can be detected using methods known to those of ordinary skill in the art. In aspects according to the present disclosure, an anti-parasitic, anti-pest or insecticidal nucleic acid may be a dsRNA.

In an aspect of the present disclosure, methods and compositions for treating *Varroa* mite infestations in bees by down-regulating calmodulin and calmodulin related *Varroa* mite gene products, are provided. In an aspect, the compositions comprise an anti-parasitic, anti-pest or insecticidal nucleic acid corresponding to the *Varroa destructor* calmodulin sequence of SEQ ID NO: 1. In an aspect, the compositions comprise an anti-parasitic, anti-pest or insecticidal nucleic acid corresponding to the *Varroa destructor* calmodulin sequence of SEQ ID NO: 2. In an aspect, the compositions comprise an anti-parasitic, anti-pest or insecticidal nucleic acid corresponding to the *Varroa destructor* calmodulin sequence of SEQ ID NO: 69. In an aspect, the compositions comprise an anti-parasitic, anti-pest or insecticidal nucleic acid corresponding to the *Varroa destructor* calmodulin sequence of SEQ ID NO: 70. In some aspects, the compositions comprise an anti-parasitic, anti-pest or insecticidal nucleic acid corresponding to a *Varroa destructor* calmodulin sequence selected from SEQ ID NOs: 71-87. In another aspect, the compositions comprise an anti-parasitic, anti-pest or insecticidal nucleic acid corresponding to a *Varroa destructor* calmodulin sequence selected from SEQ ID NOs: 3, 4, 88 and 89. In an aspect, the compositions comprise a small RNA corresponding to the *Varroa destructor* calmodulin sequence of SEQ ID NO: 1. In an aspect, the compositions comprise a small RNA corresponding to the *Varroa destructor* calmodulin sequence of SEQ ID NO: 2. In an aspect, the compositions comprise a small RNA corresponding to the *Varroa destructor* calmodulin sequence of SEQ ID NO: 69. In an aspect, the compositions comprise a small RNA corresponding to the *Varroa destructor* calmodulin sequence of SEQ ID NO: 70. In some aspects, the compositions comprise a small RNA corresponding to a *Varroa destructor* calmodulin sequence selected from SEQ ID NOs: 71-87. In another aspect, the compositions comprise a small RNA corresponding to a *Varroa destructor* calmodulin sequence selected from SEQ ID NOs: 3, 4, 88 and 89. In an aspect, the compositions comprise a dsRNA corresponding to the *Varroa destructor* calmodulin sequence of SEQ ID NO: 1. In an aspect, the compositions comprise a dsRNA corresponding to the *Varroa destructor* calmodulin sequence of SEQ ID NO: 2. In an aspect, the compositions comprise a dsRNA corresponding to the *Varroa destructor* calmodulin sequence of SEQ ID NO: 69. In an aspect, the compositions comprise a dsRNA corresponding to the *Varroa destructor* calmodulin sequence of SEQ ID NO: 70. In some aspects, the compositions comprise a dsRNA corresponding to a *Varroa destructor* calmodulin sequence selected from SEQ ID NOs: 71-87. In another aspect, the compositions comprise a dsRNA corresponding to a *Varroa destructor* calmodulin sequence selected from SEQ ID NOs: 3, 4, 88 and 89. In an aspect, the compositions comprise an siRNA corresponding to the *Varroa destructor* calmodulin sequence of SEQ ID NO: 1. In an aspect, the compositions comprise a siRNA corresponding to the *Varroa destructor* calmodulin sequence of SEQ ID NO: 2. In an aspect, the compositions comprise a siRNA corresponding to the *Varroa destructor* calmodulin sequence of SEQ ID NO: 69. In an aspect, the compositions comprise a siRNA corresponding to the *Varroa destructor* calmodulin sequence of SEQ ID NO: 70. In some aspects, the compositions comprise a siRNA corresponding to a *Varroa destructor* calmodulin sequence selected from SEQ ID NOs: 71-87. In another aspect, the compositions comprise a siRNA corresponding to a *Varroa destructor* calmodulin sequence selected from SEQ ID NOs: 3, 4, 88 and 89. In aspects according to the present disclosure the composition may comprise an anti-parasitic, anti-pest or insecticidal nucleic acid corresponding to a region of SEQ ID NO: 1 or 2. In other aspects according to the present disclosure the composition may comprise an anti-parasitic, anti-pest or insecticidal nucleic acid corresponding to a region of SEQ ID NO: 69 or 70. In yet other aspects according to the present disclosure the composition may comprise a nucleic acid corresponding to a region of a sequence selected from SEQ ID NOs: 3, 4, 88 and 89.

*Varroa* mites parasitize pupae and adult bees and reproduce in the pupal brood cells. The mites use their mouths to puncture the exoskeleton and feed on the bee's hemolymph. The present inventors unexpectedly found that polynucleotide agents administered to the bees to treat *Varroa* mite infestations presented in the bee's hemolymph thereby becoming available to the mite.

The present inventors have shown that calmodulin-targeting dsRNA fragments can successfully be transferred to *Varroa* mites (see, e.g., FIG. 2), that the dsRNA can serve to down-regulate expression of calmodulin genes in the *Varroa* mite (see, e.g., FIG. 3A) and further that targeting of calmodulin genes for down-regulation can result in a reduction in the number of *Varroa* mites (see, e.g., FIG. 3B).

Thus, according to one aspect of the present disclosure there is provided a method of preventing or treating a *Varroa destructor* mite infestation of a bee, the method comprising administering to the bee an effective amount of a nucleic acid agent comprising a nucleic acid sequence which down-regulates expression of a calmodulin gene of a *Varroa destructor* mite, thereby preventing or treating a *Varroa destructor* mite infestation of a bee.

According to this aspect of the present disclosure the agents of the present disclosure are used to prevent the *Varroa destructor* mite from living as a parasite on the bee, or larvae thereof. The phrase "*Varroa destructor* mite" refers to the external parasitic mite that attacks honey bees *Apis cerana* and *Apis mellifera*. The mite may be at an adult stage, feeding off the bee, or at a larval stage, inside the honey bee brood cell.

As mentioned, the agents of the present disclosure are capable of selectively down-regulating expression of a gene product of a *Varroa destructor* mite. As used herein, the phrase "gene product" refers to an RNA molecule or a protein. According to one aspect, the *Varroa destructor* mite gene product is one which is essential for mite viability. Down-regulation of such a gene product would typically result in killing of the *Varroa* mite. According to another aspect, the *Varroa destructor* mite gene product is one which is essential for mite reproduction. Down-regulation of such a gene product would typically result in the prevention of reproduction of the *Varroa* mite and the eventual extermination of the mite population. According to yet another aspect, the *Varroa destructor* mite gene product is one which is required to generate pathogenic symptoms in the bee. In some aspects, the *Varroa destructor* gene product is a calmodulin gene. In certain aspects, the calmodulin gene may comprise a nucleic acid sequence according to SEQ ID NO: 1 or SEQ ID NO: 2. In certain aspects, the calmodulin gene may comprise a nucleic acid sequence according to SEQ ID NO: 69 or SEQ ID NO: 70.

Examples of gene products that may be down-regulated according to this aspect of the present disclosure include, but are not limited to a calmodulin gene.

In an aspect according to the present disclosure, agents capable of down-regulating expression of a gene product of a *Varroa destructor* mite or other parasite, may downregulate to a lesser extent expression of the gene product in other animals, such as the bee or other non-target organism. Accordingly, certain agents of the present disclosure are able to distinguish between the mite gene and the bee gene, down-regulating the former to a greater extent than the latter. In some aspects, certain agents of the present disclosure are able to distinguish between the target gene in the target organism and orthologs in non-target organisms, down-regulating the former to a greater extent than the latter. In other aspects, the target gene of the parasite is downregulated while the homologous host gene is not. In yet another aspect, the target gene of the parasite does not have a homologue in the host. According to another aspect the agents of the present disclosure do not down-regulate the bee gene whatsoever. For example, this may be effected by targeting a gene that is expressed differentially in the mite and not in the bee e.g. the mite sodium channel gene—FJ216963. Alternatively, the agents of the present disclosure may be targeted to mite-specific sequences of a gene that is expressed both in the mite and in the bee.

According to one aspect, the agents of the present disclosure target segments of *Varroa* genes that are at least 100 bases long and do not carry any sequence longer than 19 bases that is entirely homologous to any bee-genome sequence or human-genome sequence. While it will be appreciated that more than one gene may be targeted in order to maximize the cytotoxic effect on the *Varroa* mites, compositions that comprise one, or a few, small RNA's would increase the probability of being a selective insecticide composition as cross reactivity with other insects may be reduced.

According to one aspect, a dsRNA composition can be prepared corresponding to the *Varroa destructor Calmodulin*-1 and *Calmodulin*-2 genes (e.g. using nucleic acid agents having the sequence as set forth in SEQ ID NOs: 1 to 4, and 69 to 89, their complements or nucleic acids directed to regions thereof).

It will be appreciated that as well as down-regulating a number of genes, the present disclosure further provides for, and includes, using a number of agents to down-regulate the same gene (e.g. a number of nucleic acids, or dsRNAs, each hybridizing to a different segment of the same gene). For example, in an aspect a combination of one or more nucleic acids corresponding to a sequence selected from the group consisting of SEQ ID NOs: 1 to 4, 6, 23, 26 to 35, and 69 to 89 may be used to increase the cytotoxic and anti-parasitic effects of the composition. Tools which are capable of identifying species-specific sequences may be used for this purpose—e.g. BLASTN and other such computer programs. U.S. Patent Publication NOs. 20090118214 and 20120108497 provide for the use of dsRNA for preventing and treating viral infections in honeybees. U.S. Patent Publication Nos. 20120258646 provides for the use of dsRNA to control *Varroa destructor* in honeybee. Each publication is hereby incorporated in their entireties.

The present disclosure provides for, and includes, compositions and methods for down-regulating the expression of a gene in a target organism. In an aspect the target organism may be a parasite. In certain aspects, the parasite may be *Varroa destructor*. As used herein, the term "down-regulating expression" refers to causing, directly or indirectly, reduction in the transcription of a desired gene, reduction in the amount, stability or translatability of transcription products (e.g. RNA) of the gene, and/or reduction in translation of the polypeptide(s) encoded by the desired gene. Downregulating expression of a gene product of a *Varroa destructor* mite can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in the *Varroa destructor* mite (for example, reduced proliferation of the mite, reduced virulence of the mite, reduced motility of the mite etc) and by testing bee infectivity/pathogenicity.

Downregulation of a pest or parasite gene product can be effected on the genomic and/or the transcript level using a variety of agents which interfere with transcription and/or translation (e.g., RNA silencing agents, Ribozyme, DNAzyme and antisense nucleic acid molecules). Downregulation of a *Varroa destructor* mite gene product can be effected on the genomic and/or the transcript level using a variety of agents which interfere with transcription and/or translation (e.g., RNA silencing agents, Ribozyme, DNAzyme and antisense nucleic acid molecules).

According to one aspect, the agent which down-regulates expression of a pest or parasite gene product is a small RNA, such as an RNA silencing agent. According to this aspect, the small RNA is greater than 15 base pairs in length. In another aspect, the small RNA is greater than 50 base pairs in length. In an aspect, the small RNA is greater than 50 base pairs in length but less than about 500 base pairs. In an aspect, the small RNA is greater than 100 base pairs in length but less than about 500 base pairs. In an aspect, the small RNA is greater than 200 base pairs in length but less than about 500 base pairs. In an aspect, the pest or parasite may be a *Varroa destructor* mite.

Another method of down-regulating a pest or parasite gene product is by introduction of small inhibitory RNAs (siRNAs). Another method of down-regulating a *Varroa* mite gene product is by introduction of small inhibitory RNAs (siRNAs).

In one aspect of the present disclosure, synthesis of RNA silencing agents suitable for use with the present disclosure can be effected as follows. First, the pest or parasite target mRNA is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex (Tuschl ChemBiochem. 2:239-245). It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (available on the internet at www.ambion.com/techlib/tn/91/912.html).

Second, potential target sites are compared to an appropriate genomic database (e.g., human, bee, monarch butterfly, mouse, rat etc.) using any sequence alignment software, such as the BLAST software available from the NCBI server (available on the internet at www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene or pest or parasite target sequence. An example of a scrambled nucleotide sequence is provided at SEQ ID NO. 5.

For example, a siRNA that may be used in this aspect of the present disclosure is one which targets a mite-specific calmodulin gene. Examples of siRNAs are provided in SEQ ID NOs: 3, 4, 88 and 89.

It will be appreciated that the RNA silencing agent of the present disclosure need not be limited to those molecules containing only RNA, but further encompasses chemically-modified nucleotides and non-nucleotides.

In some aspects, the RNA silencing agent provided herein can be functionally associated with a cell-penetrating peptide. As used herein, a "cell-penetrating peptide" is a peptide that comprises a short (about 12-residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present disclosure preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present disclosure preferably include, but are not limited to, penetratin, transportan, pls1, TAT(48-60), pVEC, MTS, and MAP.

Another agent capable of down-regulating a pest or parasite gene product is a DNAzyme molecule capable of specifically cleaving an mRNA transcript or DNA sequence of the bee pathogen polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for a review of DNAzymes, see Khachigian, L M, Curr Opin Mol Ther 4:119-21 (2002)). In an aspect, the pest or parasite gene product may be a *Varroa* mite gene product. Downregulation of pest or parasite gene products can also be effected by using an antisense polynucleotide capable of specifically hybridizing with an mRNA transcript encoding the pest or parasite gene product. Design of antisense molecules which can be used to efficiently downregulate a pest or parasite gene product must be effected while considering two aspects important to the antisense approach.

The first aspect is delivery of the oligonucleotide into the cytoplasm of the appropriate cells, while the second aspect is design of an oligonucleotide which specifically binds the designated mRNA or RNA target sequence within cells in a way which inhibits translation thereof. In an aspect, the pest or parasite gene product may be a *Varroa* mite gene product. In another aspect, the pest or parasite gene product may be calmodulin gene product.

A number of delivery strategies which can be used to efficiently deliver oligonucleotides into a wide variety of cell types (see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)).

In addition, algorithms for identifying those sequences with the highest predicted binding affinity for their target mRNA based on a thermodynamic cycle that accounts for the energetics of structural alterations in both the target mRNA and the oligonucleotide are also available (see, for example, Walton et al. Biotechnol Bioeng 65: 1-9 (1999)). Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp1) in cell culture as evaluated by a kinetic PCR technique proved effective in almost all cases, including tests against three different targets in two cell types with phosphodiester and phosphorothioate oligonucleotide chemistries. In addition, several approaches for designing and predicting efficiency of specific oligonucleotides using an in vitro system were also published (Matveeva et al., Nature Biotechnology 16: 1374-1375 (1998)).

Another agent capable of down-regulating a pest or parasite gene product is a ribozyme molecule capable of specifically cleaving an mRNA transcript encoding the *Varroa* mite gene product. Ribozymes are being increasingly used for the sequence-specific inhibition of gene expression by the cleavage of mRNAs encoding proteins of interest (Welch et al., Curr Opin Biotechnol. 9:486-96 (1998)). The possibility of designing ribozymes to cleave any specific target RNA, including viral RNA, has rendered them valuable tools in both basic research and therapeutic applications. In an aspect, the pest or parasite gene product may be a *Varroa* mite gene product. In another aspect, the pest or parasite gene product may be calmodulin gene product.

An additional method of down-regulating the expression of a pest or parasite gene product in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science (1989) 245:725-7; Moser, H. E., et al., Science, (1987) 238:645-6; Beal, P. A., et al., Science (1992) 251: 1360-1363; Cooney, M., et al., Science (1988) 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94). In an aspect, the pest or parasite gene product may be a *Varroa* mite gene product. In another aspect, the pest or parasite gene product may be calmodulin gene product.

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression.

Detailed description of the design, synthesis and administration of effective TFOs can be found in U.S. Patent Publication Nos. 2003/017068 and 2003/0096980 to Froehler et al., and 2002/0128218 and 2002/0123476 to Emanuele et al., and U.S. Pat. No. 5,721,138 to Lawn.

The polynucleotide down-regulating agents of the present disclosure may be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The polynucleotide agents of the present disclosure may comprise heterocylic nucleosides consisting of purines and the pyrimidines bases, bonded in a 3' to 5' Sphosphodiester linkage. Preferably used polynucleotide agents are those modified in either backbone, internucleoside linkages or bases, as is broadly described hereinunder.

Specific examples of polynucleotide agents useful according to this aspect of the present disclosure include polynucleotide agents containing modified backbones or non-natural internucleoside linkages. Polynucleotide agents having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, 0, S and $CH_2$ component parts, as disclosed in U.S. Pat. Nos. 5,034,506; 5,166,315; 5,185,444; 5,216,141; 5,235,033; 5,264,562; 5,264,564; 5,405,938; 5,470,967; 5,489,677; 5,541,307; 5,561,225; 5,596,086; 5,602,240; 5,602,240; 5,608,046; 5,610,289; 5,618,704; 5,623,070; 5,663,312; 5,214,134; 5,466,677; 5,610,289; 5,633,360; 5,677,437; and 5,677,439.

Other polynucleotide agents which can be used according to the present disclosure, are those modified in both sugar and the internucleoside linkage, i.e., the backbone, of the nucleotide units are replaced with novel groups. The base units are maintained for complementation with the appropriate polynucleotide target. An example for such an polynucleotide mimetic, includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present disclosure are disclosed in U.S. Pat. No. 6,303,374.

Polynucleotide agents of the present disclosure may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 613, and those disclosed by Sanghvi, Y. S., Chapter 15, Antisense Research and Applications, pages 289-2, Crooke, S. T. and Lebleu, B., ed., CRC Press, 1993. Such bases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi Y S et al. (1993) Antisense Research and Applications, CRC Press, Boca Raton 276-278) and are presently preferred base substitutions, even more particularly when combined with 2'-O-methoxyethyl sugar modifications.

Following synthesis, the polynucleotide agents of the present disclosure may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing, and/or stabilization of the duplex strands.

It will be appreciated that a polynucleotide agent of the present disclosure may be provided per se, or as a nucleic acid construct comprising a nucleic acid sequence encoding the polynucleotide agent. Typically, the nucleic acid construct comprises a promoter sequence which is functional in the host cell, as detailed herein below.

The polynucleotide sequences of the present disclosure, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the pest or parasite in a great variety of ways. According to one aspect, the nucleic acid agents are delivered directly to the pest or parasite (e.g. by spraying a mite infested hive). The nucleic acid agents, or constructs encoding same may enter the mites bodies by diffusion. In this aspect, the promoter of the nucleic acid construct is typically operational in mite cells. In an aspect, the pest or parasite may be *Varroa destructor.*

It will be appreciated that since many parasites use their mouths to puncture the host arthropod exoskeleton and feed on the arthropod's hemolymph, the present disclosure contemplates delivering the polynucleotide agents of the present disclosure to the arthropod, whereby they become presented in the arthropod hemolymph thereby becoming available to the pest or parasite. Thus, according to another aspect, the nucleic acid agents are delivered indirectly to the pest or parasite (for example to a mite via a host bee). In this aspect, the promoter of the nucleic acid construct is typically operational in host cells. In certain aspects, the pest or parasite may be *Varroa destructor* and the host arthropod may be a bee.

According to one aspect, the nucleic acid agents are delivered to the infested hosts by spraying. The nucleic acid agents, or constructs encoding same may enter the host's bodies by diffusion.

In certain aspects, the pest or parasite may be *Varroa destructor* and the host arthropod may be a bee.

According to another aspect, the nucleic acid agents are delivered to the host via its food. The present inventors consider that following ingestion of the nucleic acid agents of the present disclosure, the agents can be presented, for example in a host arthropod in the host's hemolymph, whereby it becomes available to the parasite, for example a *Varroa* mite.

Thus the polynucleotides of the present disclosure may be synthesized in vitro or in vivo, for example in a bacterial or yeast cell, and added to the food. For example double stranded RNA may be synthesized by adding two opposing promoters (e.g. T7 promoters) to the ends of the gene segments, wherein the promoter is placed immediately 5' to the gene and the promoter is placed immediately 3' to the gene segment in the opposite orientation. The dsRNA may then be prepared by transcribing in vitro with the T7 RNA polymerase.

Examples of sequences for synthesizing nucleic acids, including dsRNA, according to aspects of the present disclosure are provided in SEQ ID NOs: 1 to 4, 6, 23, 26 to 35, and 69 to 89.

It will be appreciated that some pests or parasites cause wound sites in the exoskeleton of a host arthropod. Such wound sites harbor bacterial infections. For example, a host bee wound site may harbor a bacteria such as Melissococcus pluton, which causes European foulbrood. In addition, to their parasitic effects, parasites are known to act as vectors for a number of other pathogens and parasites. For example, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections.

Thus, by killing the pest or parasite (or preventing reproduction thereof), the anti-parasitic, anti-pest or insecticidal agents of the present disclosure may be used to prevent and/or treat bacterial infections of host organisms. For example, Melissococcus pluton and viral infections in host bees caused by the above named viruses. Since *Varroa* mite infestation and viral infections are thought to be responsible for colony collapse disorder (CCD), the present agents may also be used to prevent or reduce the susceptibility of a bee colony to CCD.

It will be appreciated that in addition to feeding of anti-parasitic, anti-pest or insecticidal nucleic acid agents for reduction of the bee pathogen infection and infestation, enforcement of proper sanitation (for example, refraining from reuse of infested hives) can augment the effectiveness of treatment and prevention of infections.

Also included and provided for by the present disclosure are transgenic bacteria and yeast cells that express a selective insecticide. In one aspect, a nucleic acid encoding a small RNA, dsRNA, miRNA or a small or miRNA-resistant target nucleic acid molecule used herein is operably linked to a promoter and optionally a terminator. In some embodiments, the transgenic bacteria and yeast cells are killed, for example, by applying heat or pressure. In some embodiments, the transgenic bacteria and yeast cells are lysed prior to providing the selective insecticide to the target organism. In some embodiments, the transgenic bacteria and yeast cells are not lysed.

In one aspect, an exogenous nucleic acid molecule used herein is or encodes a small RNA, or in a particular aspect a siRNA, which can modulate the expression of a gene in a target organism. In an aspect, an exogenous nucleic acid encodes a small RNA having at least 80%, 85%, 88%, 90%, 92%, 95%, 96%, 97%, 98%, or 99% sequence identity to a sequence selected from the group consisting of SEQ ID NOs: 1-4 and 6-89. In a further aspect, an exogenous nucleic acid molecule used herein is or encodes a dsRNA molecule. In another aspect, an exogenous nucleic acid molecule used herein is or encodes an artificial miRNA. In a further aspect, an exogenous nucleic acid molecule used herein is or encodes an siRNA. In one aspect, an exogenous nucleic acid molecule used herein is or encodes a precursor of a small RNA. In another aspect, an exogenous nucleic acid molecule used herein is or encodes a precursor of a miRNA or siRNA. In one aspect, an exogenous nucleic acid molecule used herein is a naturally-occurring molecule. In another aspect, an exogenous nucleic acid molecule used herein is a synthetic molecule.

In one aspect, an exogenous nucleic acid molecule used herein is or encodes a stem-loop precursor of a small RNA or in a particular aspect a miRNA, comprising a sequence having at least 80%, 85%, 88%, 90%, 92%, 95%, 96%, 97%, 98%, or 99% sequence identity to a sequence selected from the group consisting of SEQ ID NOs: 1-4 and 6-89. A stem-loop precursor used herein comprises a sequence having at least 60%, 65%, 70%, 75%, 80%, 85%, 88%, 90%, 92%, 95%, 96%, 97%, 98%, or 99% sequence identity to a sequence selected from the group consisting of SEQ ID NOs: 1-4 and 6-89.

In one aspect, an exogenous nucleic acid molecule used herein is naked RNA or expressed from a nucleic acid expression construct, where it is operably linked to a regulatory sequence.

In one aspect, a recombinant DNA construct or a transgene disclosed herein further comprises a transcription terminator.

It is expected that during the life of a patent maturing from this application many relevant methods for down-regulating expression of gene products can be developed and the scope of the term "down-regulating expression of a gene product of a *Varroa destructor* mite" is intended to include all such new technologies a priori.

It is appreciated that certain features of the disclosure, which are, for clarity, described in the context of separate aspects, may also be provided in combination in a single aspect. Conversely, various features of the disclosure, which are, for brevity, described in the context of a single aspect, may also be provided separately or in any suitable subcombination or as suitable in any other described aspect of the disclosure. Certain features described in the context of various aspects are not to be considered essential features of those aspects, unless the aspect is inoperative without those elements. Various aspects and aspects of the present disclosure as delineated hereinabove and as claimed in the claims section below find experimental support in the following examples.

EXAMPLES

Example 1

*Varroa* Mite *Calmodulin* Gene Sequences

The *Calmodulin* (CAM) genes provided in Table 1 (SEQ ID NO: 1 and 2), or their corresponding transcripts, were used as targets of polynucleotide compositions comprising a polynucleotide that is at least 18 contiguous nucleotides identical or complementary to those genes or transcripts. The gene sequences provided in Table 1, protein sequences encoded by those genes, or sequences contained within those genes were used to obtain orthologous *Calmodulin* (CAM) genes from other arthropod pest and parasitic species not listed in Table 1. Such orthologous genes and their transcripts can then serve as targets of polynucleotides provided herein or as a source of anti-parasitic, anti-pest or insecticidal polynucleotides that are specifically designed to target the orthologous genes or transcripts.

For each *Calmodulin* DNA gene sequence provided in SEQ ID NO: 1 and 2, single stranded or double stranded DNA or RNA fragments in sense or antisense orientation or both are fed in vitro to *Varroa* mites grown on a petri plate or applied topically to bee hives to effect the expression of the CAM target genes and obtain a reduction in *Varroa destructor* mite population.

Example 2

Suppression of *Calmodulin* (CAM) Genes of *Varroa destructor*

Polynucleotides for the suppression of expression of *Calmodulin* (CAM) genes in *Varroa destructor* mite corresponding to SEQ ID NOs: 3 and 4 (Table 2) are provided and were used to used to suppress expression of *Calmodulin* (CAM) genes in *Varroa destructor* mite. The SEQ ID NOs: 3 and 4 describe a 373 bp dsRNA polynucleotide sequence and a 186 bp dsRNA polynucleotide sequence, respectively, selected from CAM-1 (SEQ ID NO: 1). SEQ ID NO: 3, corresponding to dsRNA polynucleotide CAM_L/CAM373 covers most of the open reading frame of the *Calmodulin* CAM-1 (SEQ ID NO: 1) gene. SEQ ID NO 4, corresponding to dsRNA polynucleotide CAM_S/CAM186 is a partial fragment of CAM_L/CAM373 (SEQ ID NO: 3) and is also derived from CAM-1 (SEQ ID NO: 1). SEQ ID NO: 5 in Table 2 is a control dsRNA sequence polynucleotide sequence with no more than 19 bp sequence identity to any known *Varroa destructor* gene.

TABLE 1

Target Calmodulin (CAM) genes of *Varroa destructor*

| Gene name | SEQ ID | Open reading frame DNA sequence |
|---|---|---|
| CAM-1 | 1 | ATGGCTGATCAGCTAACTGAGGAACAGATCGCCGAGTTCAAAGAGGCGTTTAGCCTGTTTGACAAGG ACGGAGATGGCACGATCACGACAAAGGAGCTCGGTACGGTAATGCGATCTCTCGGCCAGAACCCCAC TGAGGCTGAACTGCAGGACATGATCAACGAGGTCGACGCCGACGGCTCCGGAACGATAGATTTCCCT GAGTTCCTCACAATGATGGCAAGAAAGATGAAGGACACCGACTCGGAGGAGGAGATCCGAGAGGCGT TCCGCGTATTCGACAAGGATGGCAACGGTTTCATTTCGGCGGCCGAGCTCAGGCACGTTATGACCAA CCTTGGCGAGAAGCTTACGGACGAGGAGGTAGATGAGATGATTCGGGAGGCAGATATTGACGGTGAT GGTCAGGTCAACTACGAGGAGTTCGTCACCATGATGACGTCCAAGTAA |
| CAM-2 | 2 | ATGGCGGATCAGCTGACCGAGGAGCAAATCGCCGAATTCAAGGAGGCTTTCAGCCTGTTCGATAAAG ACGGTGATGGCACAATTACGACCAAGGAACTAGGGACCGTCATGCGGTCCCTCGGCCAGAACCCTAC TGAGGCTGAGCTTCAAGACATGATCAACGAGGTCGACGCTGACGGTAACGGCACTATTGACTTTCCA GAGTTTCTCACGATGATGGCGCGTAAAATGAAGGACACCGACTCCGAGGAGGAGATCCGGGAAGCTT TTAGGGTTTTTGATAAAGACGGAAATGGCTTCATTTCGGCTGCAGAGCTGAGGCACGTAATGACCAA CCTTGGCGAAAAGCTCACGGACGAGGAAGTGGACGAGATGATCCGCGAGGCGGATATCGACGGCGAC GGACAGGTCAACTACGAGGAGTTCGTCACGATGATGACATCAAAATGA |

TABLE 2 dsRNAs targeting *Varroa destructor* Calmodulin (CAM) genes

| dsRNA name | SEQ ID | Nucleic acid sequence |
|---|---|---|
| CAM L/CAM 373 | 3 | ACAGAUCGCCGAGUUCAAAGAGGCGUUUAGCCUGUUUGACAAGGACGGAGAUGGCACGAUCACGACAAAGGAG CUCGGUACGGUAAUGCGAUCUCUCGGCCAGAACCCCACUGAGGCUGAACUGCAGGACAUGAUCAACGAGGUCG ACGCCGACGGCUCCGGAACGAUAGAUUUCCCUGAGUUCCUCACAAUGAUGGCAAGAAAGAUGAAGGACACCGA CUCGGAGGAGGAGAUCCGAGAGGCGUUCCGCGUAUUCGACAAGGAUGGCAACGGUUUCAUUUCGGCGGCCGAG CUCAGGCACGUUAUGACCAACCUUGGCGAGAAGCUUACGGACGAGGAGGUAGAUGAGAUGAUUCGGGAGGCAG AUAUUGAC |
| CAM_S/CAM 186 | 4 | ACAAUGAUGGCAAGAAAGAUGAAGGACACCGACUCGGAGGAGGAGAUCCGAGAGGCGUUCCGCGUAUUCGACA AGGAUGGCAACGGUUUCAUUUCGGCGGCCGAGCUCAGGCACGUUAUGACCAACCUUGGCGAGAAGCUUACGGA CGAGGAGGUAGAUGAGAUGAUUCGGGAGGCAGAUAUUGAC |
| SCRAM | 5 | AUACUUACUGGUGCUAAUUUUUAUCGAGGAUGCCCAACUCCCCCCACUUUAAAACUGCGAUCAUACUAACGAA CUCCCGAAGGAGUGAAAGGUGUCUAUGUUGAGCUUAAUAACCUACCUUGCGAGCAAAGAAGGACUAGUUGACC CUGGGCACCCUAUAUUGUUAUGUUGUUUCGAACUGAGUUGGCACCCAUGCUGCACAUGCAACAAACAUGUCGG CCUUCGUGUCUAUCCUAGAAAAGUACCUGUGAACUUGGCUGUCUACAUCAUCAUC |

Example 3

*Varroa destructor* Bioassay at 3 Day Post-Treatment with Specific dsRNAs

Figure 2:
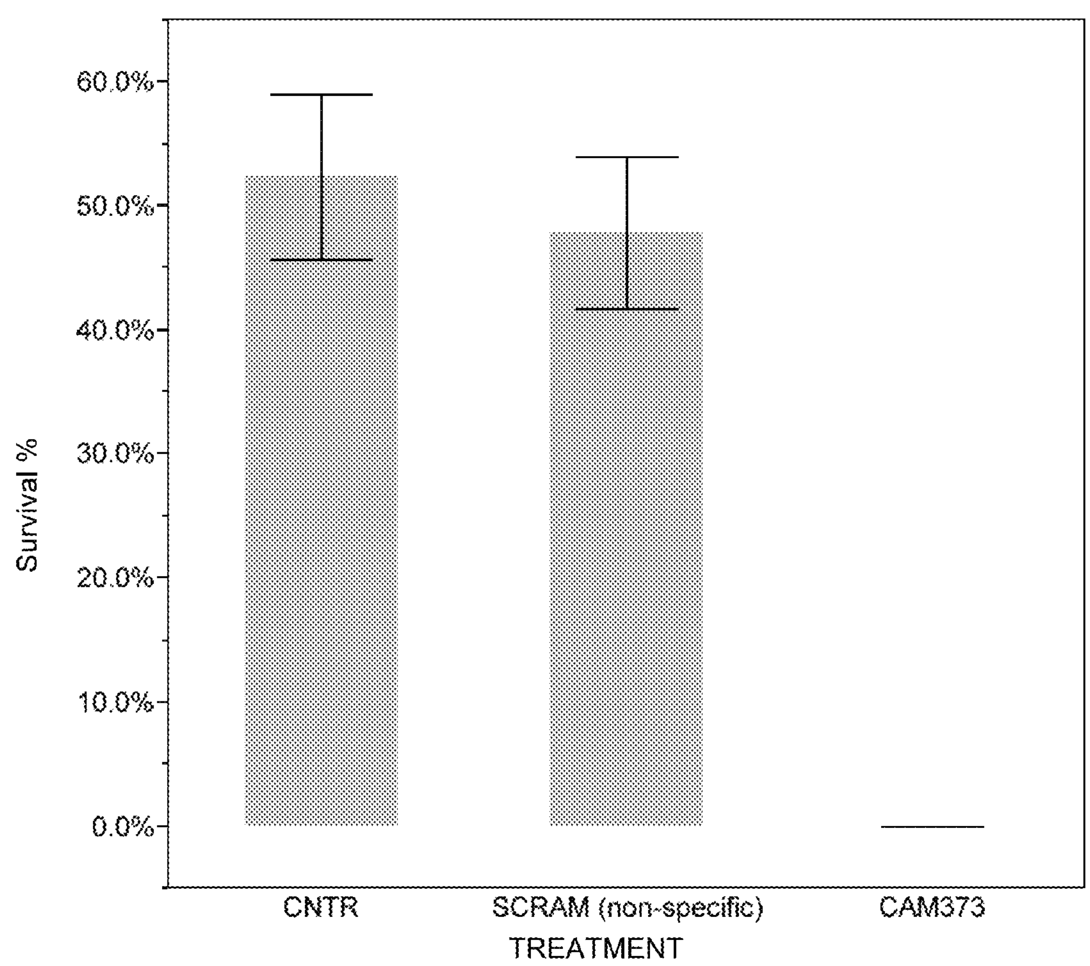
FIG. 2 presents the survival rate of mites exposed to a nucleic acid of SEQ ID NO: 3 (CAM373) in a direct feeding bioassay at 3 day post treatment relative to a non treated control (CNTR) or a non-specific sequence (SCRAM, SEQ ID NO: 5).

Adult female mites were collected from honeybee colonies and placed in a petri dish plate on top of an artificial diet solution containing a mixture of 1% tryptone, 0.5% yeast extract, 1% NaCl and 15 mg/mL agar. In this example the diet was supplemented with 50 μg kanamycin per 1 mL of diet solution. The diet/agar solution was further supplemented with 200-500 μg/mL of dsRNA and the resulting solution was poured on a petri dish. The dsRNA in this example consisted of either SEQ ID NO: 3 (CAM_L/CAM373) or SEQ ID NO: 5 (SCRAM). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted three days after being placed on the diet (FIG. 2). FIG. 2 shows that all mites were dead at three day after treatment compared to untreated plates or plates where the mites were fed on a diet supplemented with the non-specific (SCRAM) dsRNA polynucleotide.

Example 4

*Varroa destructor* Bioassay at 5 Day Post-Treatment with dsRNAs Targeting *Calmodulin*

Figure 3:
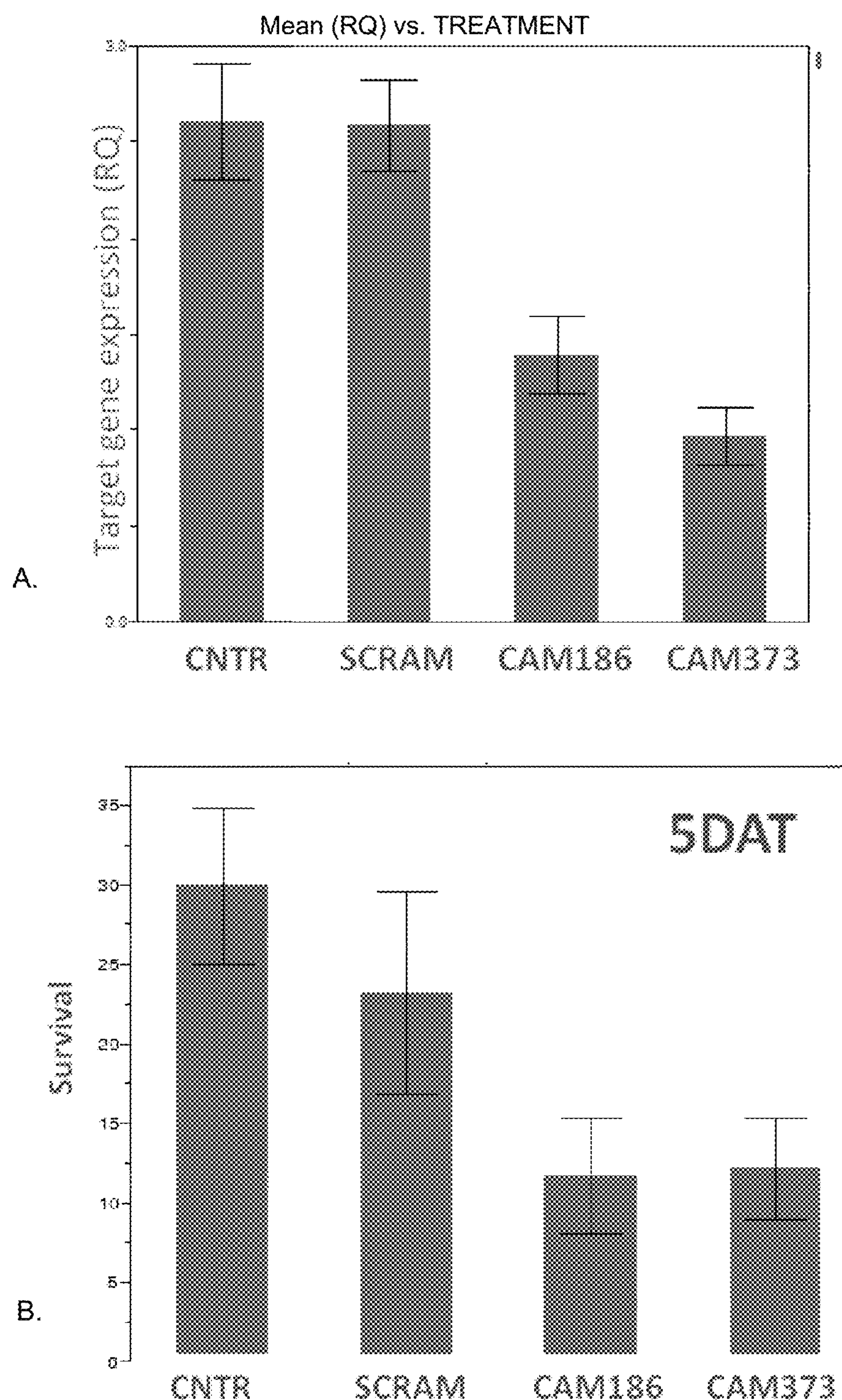
FIG. 3 Panel A presents a gene expression analysis at five day post treatment with a nucleic acid of SEQ ID NO: 3 (CAM373) or SEQ ID NO: 4 (CAM186) relative to controls. Panel B shows the survival rate of mites exposed to nucleic acids of SEQ ID NOS: 3 (CAM373) and 4 (CAM186) relative to controls.

Adult female mites were collected from honeybee colonies and placed in a petri dish plate on top of an artificial diet solution. The artificial diet contained a mixture of 1% tryptone, 0.5% yeast extract, 1% NaCl and 15 mg/mL agar. In this example the diet was further supplemented with Antimycotic Solution (100×, Sigma Aldrich) at 8× final concentration, 500 μg/mL kanamycin and 220 U/mL nystatin. The diet/agar solution was further supplemented with 200-500 μg/mL of dsRNA and the resulting solution was poured on a petri dish. The dsRNA in this example consisted of either SEQ ID NO: 3 (CAM_L/CAM373), or SEQ ID NO: 4 (CAM_S/CAM186), or SEQ ID NO: 5 (SCRAM). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted at five days after being placed on the diet (FIG. 3). For molecular analysis, live mites were removed from the plates, snap frozen in liquid nitrogen and TAQMAN™ analysis was performed to assess the levels of *Calmodulin* (CAM) RNA. FIG. 3, Panel A. the RNA levels for *Calmodulin* (CAM) genes in mites exposed to SEQ ID NO: 3 (CAM_L/CAM373) or SEQ ID NO: 4 (CAM_S/CAM186) was highly reduced compared to the non-specific (SCRAM) treatment or no treatment (CNTR). FIG. 3, Panel B, a statistically significant mortality in mites that were exposed to dsRNA against *Calmodulin* (CAM) was observed at 5 days after treatment.

Example 5

Method for Delivering of dsRNA Polynucleotides Targeting *Varroa* Genes Using a Spray-Dried or Semi-Solid Formulation dsRNA used to suppress expression of *Varroa* target *Calmodulin* (CAM) genes was prepared in a formulation containing 1 part dsRNA and ~14 parts trehalose in a phosphate buffer (a solution of 1.15 mM $KH_2PO_4$ (monobasic) and 8 mM $Na_2HPO_4$ (dibasic), pH 8.0) as illustrated in Table 3. Using a Büchi B-290 mini spray dryer, the liquid formulation was atomized into droplets and heated with gas to produce a flowable powder.

TABLE 3

Formulation Preparation

| dsRNA | Stock buffer (X % w/v trehalose + phosphate buffer) | Final buffer (X % w/v trehalose + phosphate buffer) | Total vol (mL) | Stock buffer (mL) | dsRNA stock (mL) | Ratio | Active Ingredient (AI) conc (mg/mL) | Active Ingredient (AI) conc (% solids) | Ratio of AI (dsRNA) to Buffer (trehalose + phosphate buffer) |
|---|---|---|---|---|---|---|---|---|---|
| CAM_L/CAM373 | 40 | 10 | 1100 | 275.00 | 825.00 | ¼ | 7.20 | 0.720 | 13.9 |
| CAM_S/CAM186 | 40 | 10 | 1285 | 321.21 | 963.75 | ¼ | 6.75 | 0.675 | 14.8 |

The resulting particles were formulated with powdered sugar and applied evenly to hives by spreading the powdered sugar evenly on top of the frames. In other aspects, a semi-solid preparation of the spray-dried material is prepared with water and the sugar-water ("bee-candy") formulation is fed to the bee hives by allowing the bees to feed on it.

Example 6

In Vivo Reduction of *Varroa* Mite in Bee Hives after Treatment with dsRNA Targeting *Calmodulin* (CAM) Genes

Figure 4:
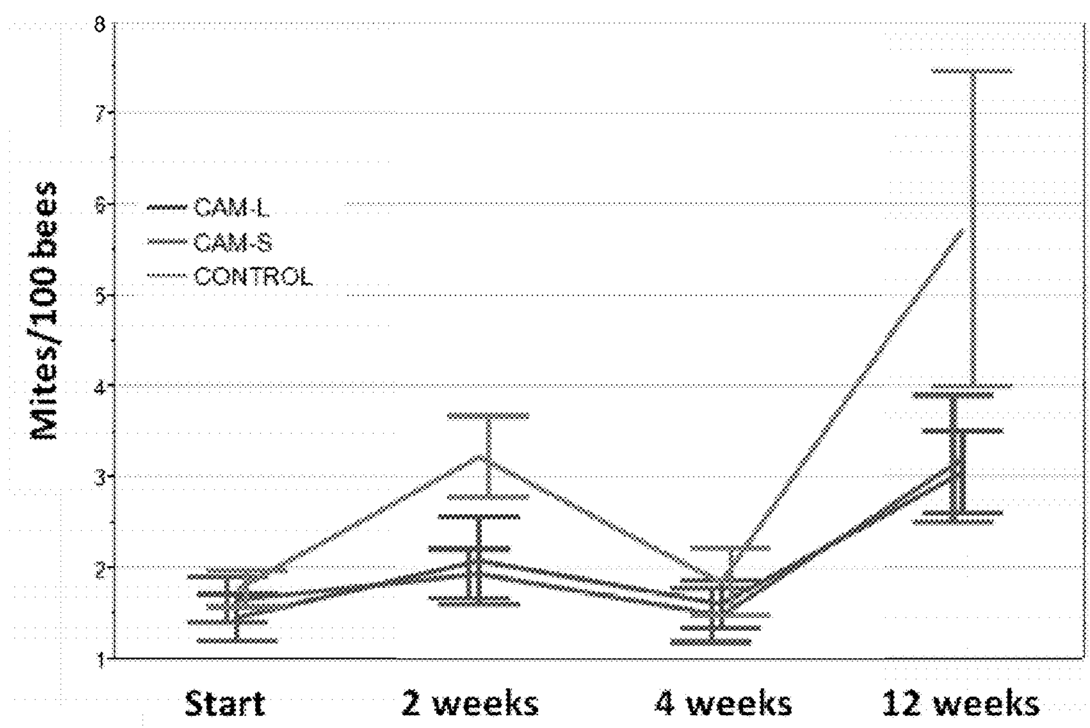
FIG. 4 presents a mite load/100 bees of treated hives relative to untreated controls over a distinct time period.

*Varroa* mites infesting adult honey bees in the hives were collected and counted using standard mite counting methodology. Hives were treated with spray dried dsRNA according to Example 7 comprising SEQ ID NO: 3 (CAM-L), SEQ ID NO: 4 (CAM-S), or no treatment (CONTROL). The mite load of each hive was assessed at the beginning of the experiment and at 2 weeks, 4 weeks and 12 weeks after treatment. FIG. 4 shows the mite load of the treated hives compared to the hives that did not receive the treatment. The number of mites counted was normalized to 100 adult bees and is representative of the *Varroa* mite load.

Example 7

Detection of Transitive Small RNAs in *Varroa* Following Treatment with dsRNA Targeting *Calmodulin* (CAM) Genes

*Varroa* mites were collected from hives treated with SEQ ID NO: 3 dsRNA polynucleotides and collected from the hive at 7 day after treatment. *Varroa* RNA was extracted and small RNA sequencing analysis performed using the SOLiD platform. The majority of small RNA molecules were detected outside the dsRNA sequence region and specifically toward the 3' portion of the dsRNA region of SEQ ID NO: 3. Additionally, the majority of the transitive reads were in the antisense orientation relative to the *Calmodulin* (CAM) gene transcript sequence. Further, small RNAs specific for CAM-2 (SEQ ID NO: 2) were detected in this experiment despite the hives being treated with dsRNA for SEQ ID NO: 3, which is predicted to be specific for CAM-1 (SEQ ID NO: 1). This observation supports the hypothesis that suppression of RNA expression and transitive small RNA generation in *Varroa* works even when only a small fragment between the two genes shares complete identity at the DNA level (in this case 23 nucleotides).

Example 8

*Calmodulin* (CAM) Gene Homologs from Arthropod Pest and Parasite Species and Corresponding dsRNA Polynucleotides Using standard bioinformatics technique and the sequences SEQ ID NOs: 1 and 2 for *Varroa destructor* a set of 31 conserved *Calmodulin* (CAM) gene sequences were identified in arthropod pest species that infest either other arthropods or mammals and that will be targeted for gene regulation. These sequences were identified and presented as a phylogenetic tree in FIG. 1. The DNA sequences in FIG. 1 were further analyzed by identifying the conserved 373 bp domain within each sequence that corresponds to SEQ ID NO: 3 (CAM_L/CAM373). Table 4 lists the SEQ ID NOs of the newly identified *Calmodulin* (CAM) gene sequences as well as the corresponding 373 bp dsRNA polynucleotide trigger sequences. The 373 bp polynucleotide dsRNA sequences will be tested either alone or in combination in direct feeding assays against their respective arthropod species.

TABLE 4

Calmodulin (CAM) gene sequences identified from arthropod pests or parasites and their corresponding 373 bp RNA polynucleotides.

| SEQ ID NO | Gene Name | Organism/Species | Type |
|---|---|---|---|
| 6 | CAM-3 | *Varroa destructor* | cDNA |
| 7 | CAM-1 | *Ixodes scapularis* | cDNA |
| 8 | CAM-1 | *Aedes aegypti* | cDNA |
| 9 | CAM-1 | *Culex quinquefasciatus* | cDNA |
| 10 | CAM-1 | *Acyrthosiphon pisum* | cDNA |
| 11 | CAM-1 | *Harpegnathos saltator* | cDNA |
| 12 | CAM-1 | *Pediculus humanus corporis* | cDNA |
| 13 | CAM-1 | *Anopheles gambiae* | cDNA |
| 14 | CAM-1 | *Solenopsis invicta* | cDNA |
| 15 | CAM-1 | *Ixodes scapularis* | RNA |
| 16 | CAM-1 | *Aedes aegypti* | RNA |
| 17 | CAM-1 | *Culex quinquefasciatus* | RNA |
| 18 | CAM-1 | *Acyrthosiphon pisum* | RNA |
| 19 | CAM-1 | *Harpegnathos saltator* | RNA |
| 20 | CAM-1 | *Pediculus humanus corporis* | RNA |
| 21 | CAM-1 | *Anopheles gambiae* | RNA |
| 22 | CAM-1 | *Solenopsis invicta* | RNA |
| 23 | CAM-3 | *Varroa destructor* | RNA |
| 24 | CAM-1 | *Tetranychus urticae* | cDNA |
| 25 | CAM-1 | *Tetranychus urticae* | RNA |
| 26 | CAM-4 | *Varroa destructor* | cDNA |
| 27 | CAM-4 | *Varroa destructor* | RNA |
| 28 | CAM-5 | *Varroa destructor* | cDNA |
| 29 | CAM-5 | *Varroa destructor* | RNA |
| 30 | CAM-7 | *Varroa destructor* | cDNA |
| 31 | CAM-7 | *Varroa destructor* | RNA |
| 32 | CAM-8 | *Varroa destructor* | cDNA |
| 33 | CAM-8 | *Varroa destructor* | RNA |
| 34 | CAM-9 | *Varroa destructor* | cDNA |
| 35 | CAM-9 | *Varroa destructor* | RNA |
| 36 | CAM | *Ixodes scapularis* | cDNA |
| 37 | CAM | *Ixodes scapularis* | RNA |
| 38 | CAM | *Ixodes scapularis* | cDNA |
| 39 | CAM | *Ixodes scapularis* | RNA |
| 40 | CAM | *Ixodes scapularis* | cDNA |
| 41 | CAM | *Ixodes scapularis* | cDNA |
| 42 | CAM | *Ixodes scapularis* | RNA |
| 43 | CAM | *Aedes aegypti* | cDNA |
| 44 | CAM | *Aedes aegypti* | RNA |
| 45 | CAM | *Aedes aegypti* | cDNA |
| 46 | CAM | *Aedes aegypti* | RNA |
| 47 | CAM | *Aedes aegypti* | cDNA |
| 48 | CAM | *Aedes aegypti* | RNA |
| 49 | CAM | *Culex quinquefasciatus* | cDNA |
| 50 | CAM | *Culex quinquefasciatus* | RNA |
| 51 | CAM | *Culex quinquefasciatus* | cDNA |
| 52 | CAM | *Culex quinquefasciatus* | RNA |
| 53 | CAM | *Culex quinquefasciatus* | cDNA |
| 54 | CAM | *Culex quinquefasciatus* | RNA |
| 55 | CAM | *Culex quinquefasciatus* | cDNA |
| 56 | CAM | *Culex quinquefasciatus* | RNA |
| 57 | CAM | *Acyrthosiphon pisum* | cDNA |
| 58 | CAM | *Acyrthosiphon pisum* | RNA |
| 59 | CAM | *Acyrthosiphon pisum* | cDNA |
| 60 | CAM | *Acyrthosiphon pisum* | RNA |
| 61 | CAM | *Pediculus humanus* | cDNA |
| 62 | CAM | *Pediculus humanus* | RNA |
| 63 | CAM | *Pediculus humanus* | cDNA |
| 64 | CAM | *Pediculus humanus* | RNA |
| 65 | CAM | *Pediculus humanus* | cDNA |
| 66 | CAM | *Pediculus humanus* | RNA |
| 67 | CAM | *Pediculus humanus* | cDNA |
| 68 | CAM | *Pediculus humanus* | RNA |

Example 9

*Varroa Calmodulin* (CAM) Gene Transcripts and dsRNA Trigger Sequences

The *Calmodulin* (CAM) sequences provided in Table 5 (SEQ ID NOs: 69 and 70), or their corresponding transcripts, were used as targets of polynucleotide compositions comprising a polynucleotide that is at least 18 contiguous nucleotides identical or complementary to those genes or transcripts. The 5' and 3'UTR sequences for the *Varroa Calmodulin* sequences were identified by RNA sequencing.

TABLE 5

Target transcripts for Calmodulin (CAM) genes of *Varroa destructor*

| Gene name and Species | SEQ ID NO | Type |
|---|---|---|
| CAM-1; *Varroa destructor* | 69 | RNA |
| CAM-2; *Varroa destructor* | 70 | RNA |

SEQ ID NOs: 69 and 70 were tiled in 150 bp fragments. Table 6 illustrates the top strand (5'-3') for the 150 bp fragments that tile across SEQ ID NOs: 69 and 70.

TABLE 6

Tiled polynucleotide sequences for CAM-1 and CAM-2 genes

| Gene name | SEQ ID NO | Position within transcript sequence |
|---|---|---|
| CAM-1 | 71 | 1-150 |
| CAM-1 | 72 | 151-300 |
| CAM-1 | 73 | 301-450 |
| CAM-1 | 74 | 451-600 |
| CAM-1 | 75 | 601-750 |
| CAM-1 | 76 | 751-900 |
| CAM-1 | 77 | 901-1050 |
| CAM-1 | 78 | 1051-1200 |
| CAM-1 | 79 | 1201-1350 |
| CAM-1 | 80 | 1351-1500 |
| CAM-2 | 81 | 1-150 |
| CAM-2 | 82 | 151-300 |
| CAM-2 | 83 | 301-450 |
| CAM-2 | 84 | 451-600 |
| CAM-2 | 85 | 601-750 |
| CAM-2 | 86 | 751-900 |
| CAM-2 | 87 | 901-1050 |

One or more dsRNA comprising a sequence selected from SEQ ID NOs: 71-87 is provided in vitro to *Varroa* mites grown on a petri plate or applied topically to bee hives to effect the expression of the CAM target genes and obtain a reduction in *Varroa destructor* mite population.

Example 10

In Vitro Bioassay of *Calmodulin* (CAM) Targeting Triggers in *Varroa* Mite

Polynucleotide trigger sequences targeting *Calmodulin* (CAM)-1 and 2 were generated based on conserved sequence overlap between CAM-1 and CAM-2 sequences. These are presented as SEQ ID NOs: 88 and 89 (targeting CAM-1 and CAM-2, respectively).

Figure 5:
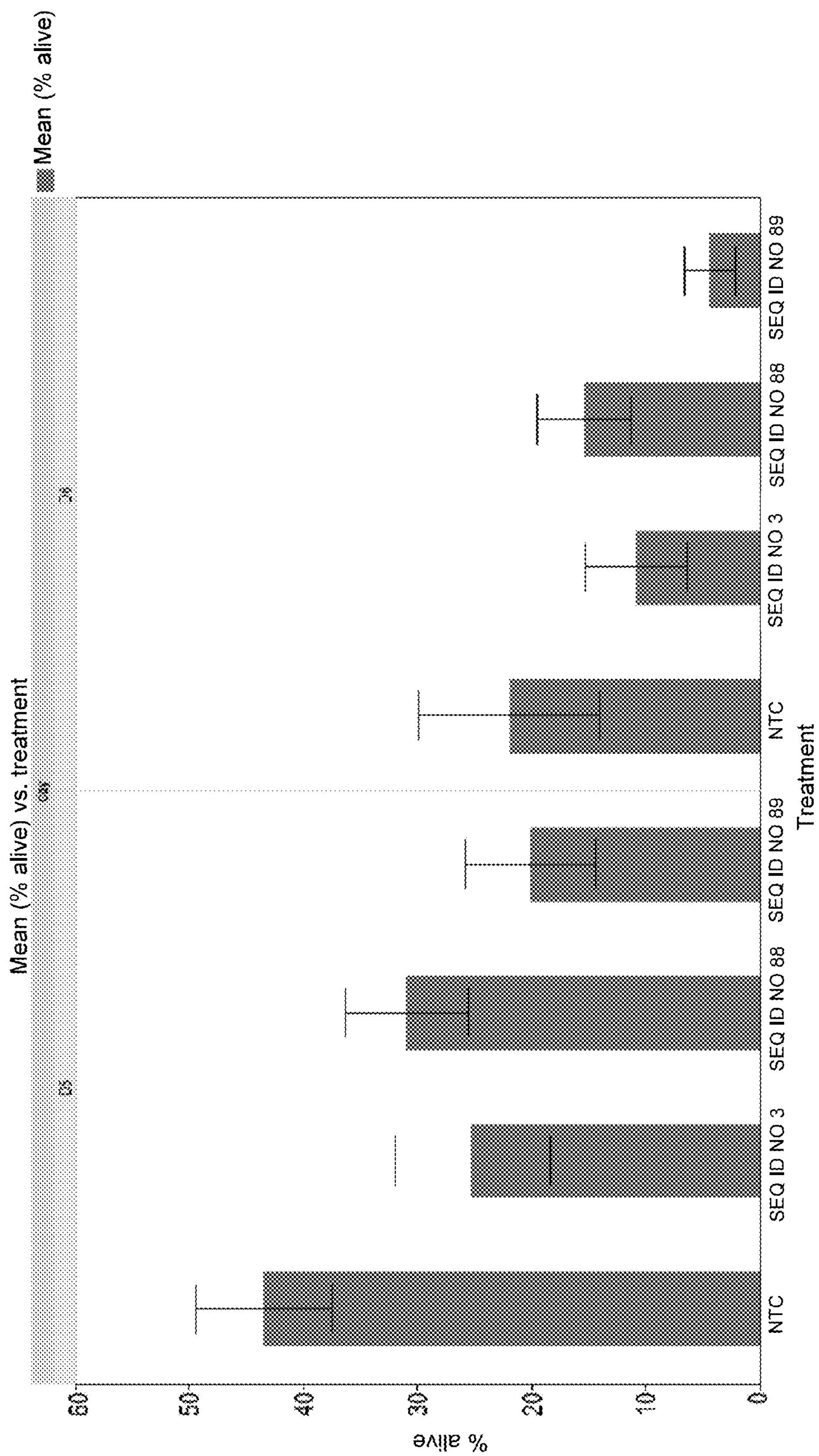
FIG. 5 presents the % survival of mites treated with SEQ ID NO: 3, SEQ ID NO: 88 or SEQ ID NO: 89 relative to untreated (NTC) at Day 5 (D %) or Day 6 (D6) post-treatment.
Figure 6:
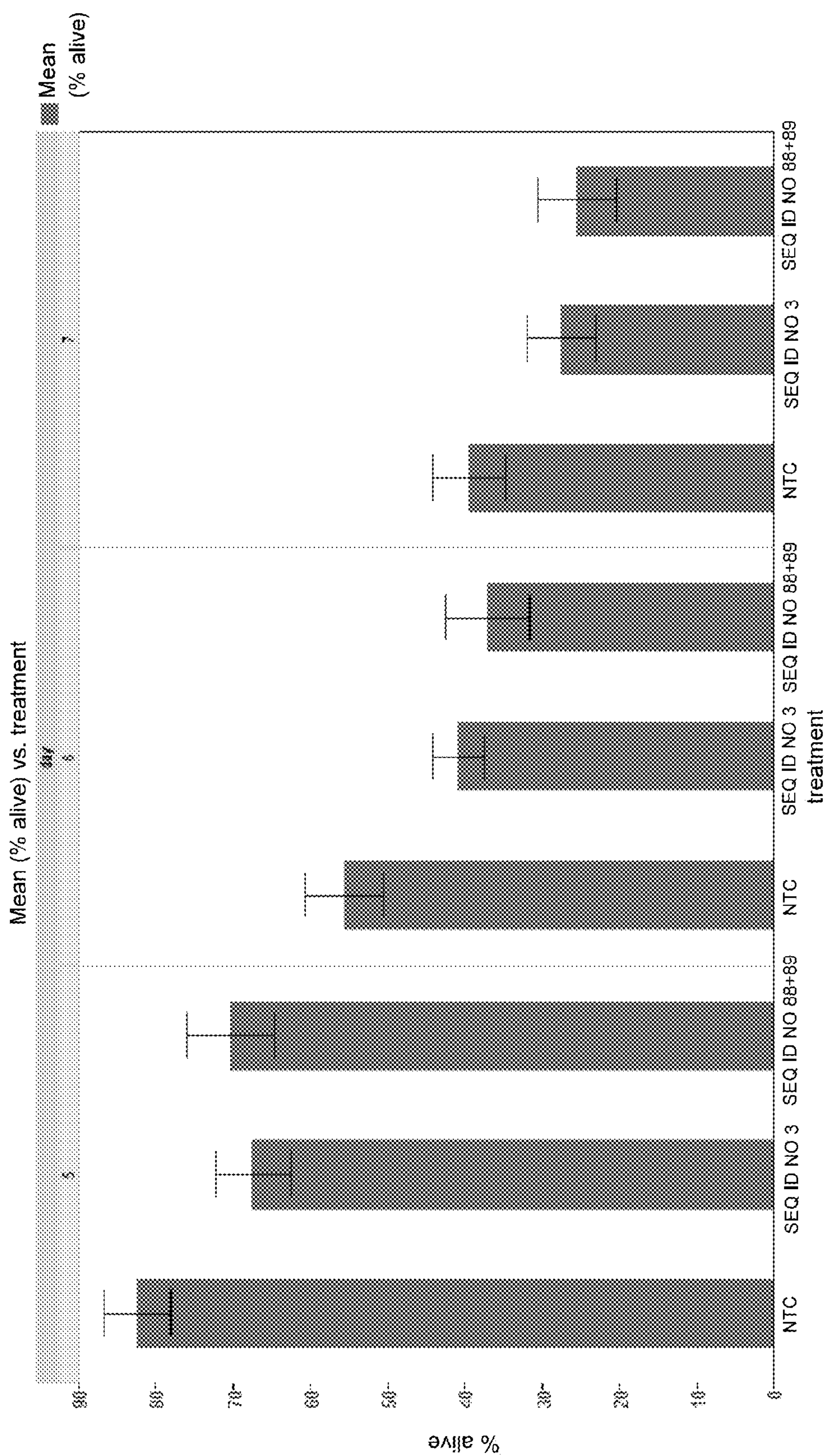
FIG. 6 presents the % survival of mites treated with SEQ ID NO: 3 or a mixture of SEQ ID NO: 88 and SEQ ID NO: 89 relative to untreated (NTC) at Day 5 (5), Day 6 (6) and Day 7 (7).

Polynucleotide sequences selected from SEQ ID NOs: 88 and 89 were tested in an in vitro bioassay for their ability to suppress viability of adult *Varroa* mites. Adult female mites were collected from honeybee colonies and placed in a petri dish plate on top of an artificial diet solution. The artificial diet contained a mixture of 1% tryptone, 0.5% yeast extract, 1% NaCl and 15 mg/mL agar. In this example, the diet was further supplemented with Antimycotic Solution (100×, Sigma Aldrich) at 8× final concentration, 500 μg/mL kanamycin and 220 U/mL nystatin. The diet/agar solution was further supplemented with 200-500 μg/mL of dsRNA and the resulting solution was poured on a petri dish. The dsRNA in this example consisted of either SEQ ID NO: 3 (CAM373), SEQ ID NO: 88 (CAM-1), or SEQ ID NO: 89 (CAM-2) or non-treated control (NTC). Fifteen mites were applied to each plate and the experiment was conducted in triplicate. The diet plates with the mites were incubated at 29° C. with 50-60% relative humidity. At specific time intervals the plates were inspected and dead mites were counted and removed. For mortality studies the mites were counted at five and six days after being placed on the diet (FIG. 5). Additionally, the dsRNA for SEQ ID NO: 88 (CAM-1) and SEQ ID NO: 89 (CAM-2) were mixed in equimolar amount and fed as described above to the mites. FIG. 6 shows the result of this application.

For molecular analysis, live mites are removed from the plates, snap frozen in liquid nitrogen and TAQMAN™ analysis is performed to assess the levels of *Calmodulin* (CAM) RNA.

Example 11

Figure 7:
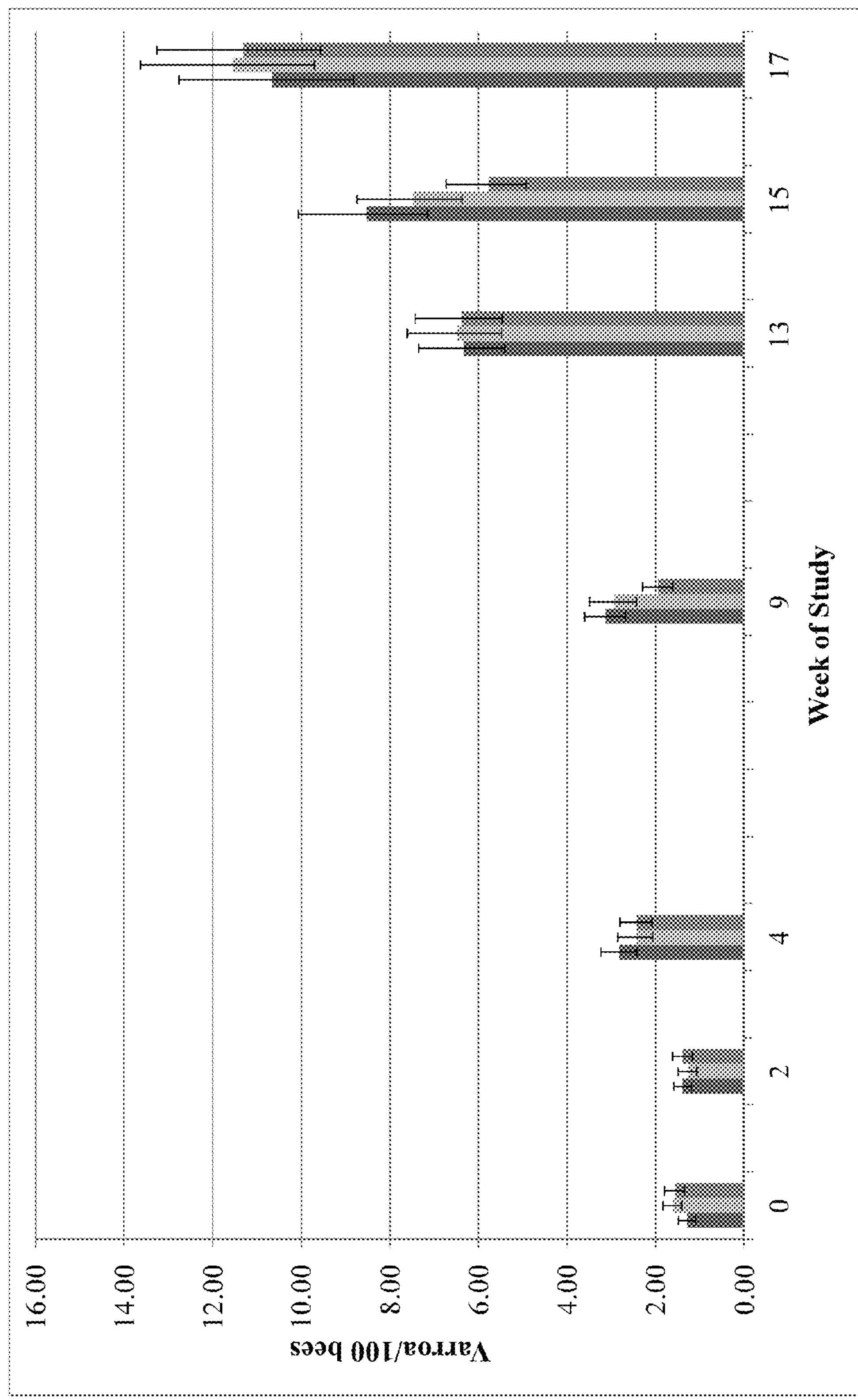
FIG. 7 presents the *Varroa* mite load/100 bees of treated hives relative to untreated controls over a 17 week time period. The leftmost bars represent hives treated with the non-specific sequence (SCRAM, SEQ ID NO: 5), the middle bars are hives left untreated, and the rightmost bar are hives treated with SEQ ID NO: 3 (CAM 373).

In Vivo Field Reduction of *Varroa* Mite Infestation in Field Treated Bee Hives after Treatment with dsRNA Targeting *Calmodulin* (CAM) Gene dsRNA used to suppress expression of *Varroa* targeted *Calmodulin* (CAM) genes was prepared by mixing dsRNA stock in Phosphate Buffer with 66% sugar syrup. The liquid formulation was supplied as a syrup to the bees, allowed to feed on it until fully consumes (approximately 2-3 days). Each field testing group consisted of 33 hives. The groups consisted of non-treated hives, non-specific trigger treated (SEQ ID NO: 5) and specific trigger treated (SEQ ID NO: 3). Bees were treated in two rounds, each round consisted of two feedings two weeks apart: at the start of the delivery (week 0) and two weeks later (week 2), then again on week 13 and 15. Assessment of bee survival was done at 4, 9, 13, 15 and 17 weeks (FIG. 7). Significant suppression of *Varroa* population was observed following treatment with the specific trigger (SEQ ID NO:3) at week 9.

What is claimed is:

1. A bee-ingestible, bee-absorbable, mite-ingestible, or mite-absorbable composition comprising an excipient and a nucleic acid molecule having a sequence that is at least 96% identical or complementary to at least 21 contiguous nucleotides of SEQ ID NO: 3.

2. The composition of claim 1, wherein said nucleic acid sequence is a dsRNA.

3. The composition of claim 1, wherein said excipient is selected from the group consisting of protein, pollen, carbohydrate, polymer, liquid solvent, sugar syrup, sugar solid, and semi-solid feed.

4. The composition of claim 2, wherein said dsRNA is an siRNA.

5. The composition of claim 1, wherein said nucleic acid sequence comprises at least 23 contiguous nucleotides of SEQ ID NO: 3.

6. The composition of claim 2, wherein said dsRNA sequence comprises at least 23 contiguous nucleotides of SEQ ID NO: 3.

7. A nucleic acid construct comprising a nucleic acid that encodes a sequence that is at least 95% identical or complementary to SEQ ID NO: 3 operably linked to a promoter sequence functional in a host cell and capable of producing a dsRNA when introduced into said host cell.

8. The nucleic acid construct of claim 7, further comprising at least one regulatory element selected from the group consisting of translation leader sequences, introns, enhancers, stem-loop structures, repressor binding sequences, termination sequences, pausing sequences, and polyadenylation recognition sequences.

9. The nucleic acid construct of claim 7, wherein said host cell is selected from the group consisting of a bacteria cell and a yeast cell.

10. A method of providing a composition to a honeybee, comprising providing the bee an effective amount of the composition of claim 1, whereby the nucleic acid is present in honeybee tissue.

11. The method of claim 10, wherein said calmodulin gene sequence is a *Varroa destructor* calmodulin gene sequence.

12. The method of claim 10, wherein said honeybee is a forager or a hive bee.

13. The method of claim 11, wherein said honeybee is a bee of a colony and said providing reduces the susceptibility of said bee colony to *Varroa destructor*, reduces the parasitation of said bee colony by *Varroa destructor*, or reduce the parasite load of said bee colony by *Varroa destructor*.

14. The method of claim 11, wherein said providing reduces the susceptibility of said honeybee to *Varroa destructor*, reduces the parasitation of said honeybee by *Varroa destructor*, or reduce the parasite load of said honeybee by *Varroa destructor*.

15. The composition of claim 1, further comprising one or more nucleic acid molecules having a second nucleic acid sequence that is essentially identical or essentially complementary to a different region of a calmodulin gene sequence.

* * * * *

SEQUENCE LISTING

```
<160> NUMBER OF SEQ ID NOS: 89

<210> SEQ ID NO 1
<211> LENGTH: 450
<212> TYPE: DNA
<213> ORGANISM: Varroa destructor

<400> SEQUENCE: 1

atggctgatc agctaactga ggaacagatc gccgagttca aagaggcgtt tagcctgttt     60

gacaaggacg gagatggcac gatcacgaca aaggagctcg gtacggtaat gcgatctctc    120

ggccagaacc ccactgaggc tgaactgcag gacatgatca acgaggtcga cgccgacggc    180

tccggaacga tagatttccc tgagttcctc acaatgatgg caagaaagat gaaggacacc    240

gactcggagg aggagatccg agaggcgttc cgcgtattcg acaaggatgg caacggtttc    300

atttcggcgg ccgagctcag gcacgttatg accaaccttg gcgagaagct tacggacgag    360
```

```
gaggtagatg agatgattcg ggaggcagat attgacggtg atggtcaggt caactacgag    420

gagttcgtca ccatgatgac gtccaagtaa                                     450


<210> SEQ ID NO 2
<211> LENGTH: 450
<212> TYPE: DNA
<213> ORGANISM: Varroa destructor

<400> SEQUENCE: 2

atggcggatc agctgaccga ggagcaaatc gccgaattca aggaggcttt cagcctgttc     60

gataaagacg gtgatggcac aattacgacc aaggaactag ggaccgtcat gcggtccctc    120

ggccagaacc ctactgaggc tgagcttcaa gacatgatca acgaggtcga cgctgacggt    180

aacggcacta ttgactttcc agagtttctc acgatgatgg cgcgtaaaat gaaggacacc    240

gactccgagg aggagatccg ggaagctttt agggtttttg ataaagacgg aaatggcttc    300

atttcggctg cagagctgag gcacgtaatg accaaccttg gcgaaaagct cacggacgag    360

gaagtggacg agatgatccg cgaggcggat atcgacggcg acggacaggt caactacgag    420

gagttcgtca cgatgatgac atcaaaatga                                     450


<210> SEQ ID NO 3
<211> LENGTH: 373
<212> TYPE: RNA
<213> ORGANISM: Varroa destructor

<400> SEQUENCE: 3

acagaucgcc gaguucaaag aggcguuuag ccuguuugac aaggacggag auggcacgau     60

cacgacaaag gagcucggua cgguaaugcg aucucucggc cagaacccca cugaggcuga    120

acugcaggac augaucaacg aggucgacgc cgacggcucc ggaacgauag auuucccuga    180

guuccucaca augauggcaa gaaagaugaa ggacaccgac ucggaggagg agauccgaga    240

ggcguuccgc guauucgaca aggauggcaa cgguuucauu ucggcggccg agcucaggca    300

cguuaugacc aaccuuggcg agaagcuuac ggacgaggag guagaugaga ugauucggga    360

ggcagauauu gac                                                       373


<210> SEQ ID NO 4
<211> LENGTH: 186
<212> TYPE: RNA
<213> ORGANISM: Varroa destructor

<400> SEQUENCE: 4

acaaugaugg caagaaagau gaaggacacc gacucggagg aggagauccg agaggcguuc     60

cgcguauucg acaaggaugg caacgguuuc auuucggcgg ccgagcucag gcacguuaug    120

accaaccuug gcgagaagcu uacggacgag gagguagaug agaugauucg ggaggcagau    180

auugac                                                               186


<210> SEQ ID NO 5
<211> LENGTH: 274
<212> TYPE: RNA
<213> ORGANISM: Artificial Sequence
<220> FEATURE:
<223> OTHER INFORMATION: Synthetic sequence as negative control

<400> SEQUENCE: 5

auacuuacug gugcuaauuu uuaucgagga ugcccaacuc cccccacuuu aaaacugcga     60

ucauacuaac gaacucccga aggagugaaa ggugucuaug uugagcuuaa uaaccuaccu    120
```

```
ugcgagcaaa gaaggacuag uugacccugg gcacccuaua uuguuauguu guuucgaacu    180

gaguuggcac ccaugcugca caugcaacaa acaugucggc cuucgugucu auccuagaaa    240

aguaccugug aacuuggcug ucuacaucau cauc                                274


<210> SEQ ID NO 6
<211> LENGTH: 432
<212> TYPE: DNA
<213> ORGANISM: Varroa destructor

<400> SEQUENCE: 6

ctgccggagg aacaggtggc tgaatttaaa gaggcctttc ttttgtttga caaggacgcc     60

gatggaatga ttacggccgc cgaactaggc gtcgtcatgc gatcgcttgg ccagcgacct    120

acggagcaag agctcaagaa aatggttacc atggttgacc aggacggcaa tggtacaatc    180

gagttcaacg agtttttgat gatgatgtct cgcaagatga aggaggcaga ctcggaggaa    240

gaactccggg aggcgttccg tgtgttcgat cgagacggtg acggattcat ctcgcgggac    300

gagctcagtg tcgtcatgaa caacctcggc gagaaattaa gtgacgatga tgttgaggat    360

atgattcgag aggccgatct ggacggcgat ggcaagatta actaccaaga gtttgtgctc    420

attatcacct cc                                                        432


<210> SEQ ID NO 7
<211> LENGTH: 480
<212> TYPE: DNA
<213> ORGANISM: Ixodes scapularis

<400> SEQUENCE: 7

atggctgatc agcttacaga agaacagatt gcagttcaag gaggcgttct tcgctgttcg     60

acaaggacgg aggatggcac catcacgacc aaggagctgg gcacggtcat gcgctcgctc    120

ggccagaacc cgacggaggc ggagctgcag gacatgatca acgaggtgga cgcagacggc    180

aacggaacga tcgacttccc cgagttcctt acgatgatgg cgcgcaagat gaaggacacg    240

gactctgagg aggagatccg ggaggcgttc cgggtgttcg acaaggacgg caacggcttc    300

atctctgcgg cggagctgcg ccacgtcatg accaacctgg gcgagaagct gacggacgag    360

gaggtggacg agatgatccg ggaggcggac atcgacgggg acgggcaggt caactacgaa    420

ggtgggcacg ctttccctcc cttggttatc ctcctgctat gctttctgca gttgctgtga    480


<210> SEQ ID NO 8
<211> LENGTH: 450
<212> TYPE: DNA
<213> ORGANISM: Aedes aegypti

<400> SEQUENCE: 8

atggccgatc aacttacaga agagcagatt gccgaattca aagaagcgtt ttcgctgttc     60

gacaaagacg gtgacggcac aatcacaacc aaggaactgg gaaccgtgat gcgatcgtta    120

ggccagaacc ccacagaagc agaactgcaa gatatgataa acgaagtcga cgcggacggc    180

aacggcacga tcgatttccc cgaattcctg accatgatgg ctcgcaaaat gaaggacacc    240

gatagcgaag aggaaatccg ggaggcgttc cgagtcttcg acaaggacgg caacggcttc    300

atctcggcag ctgagctgcg tcatgtcatg accaatctcg gcgagaagct aacggacgag    360

gaggtggatg agatgatccg cgaagccgac atagatggcg atggccaagt taattatgaa    420

gaattcgtaa caatgatgac atcgaagtga                                     450
```

<210> SEQ ID NO 9
<211> LENGTH: 450
<212> TYPE: DNA
<213> ORGANISM: Culex quinquefasciatus

<400> SEQUENCE: 9

```
atggccgatc aacttacaga ggaacagatc gccgagttca aagaagcgtt ctcgctgttc     60

gacaaagacg gtgacggcac gatcacgacc aaggagctgg gcaccgtgat gcgatcgtta    120

ggccagaacc ccacagaagc agagctgcaa gacatgataa acgaggtcga tgcggacggc    180

aacggcacga tcgacttccc cgagtttctc accatgatgg ctcgcaaaat gaaggacacc    240

gatagcgaag aggaaatccg ggaggcgttc cgagtcttcg acaaggacgg caacggcttc    300

atctcggcgg ccgagctgcg ccacgtcatg accaatctcg gcgagaagct cacggacgag    360

gaggtggatg agatgatccg cgaggccgac attgacggcg atggccaagt taattatgaa    420

gaattcgtaa caatgatgac atcgaagtga                                    450
```

<210> SEQ ID NO 10
<211> LENGTH: 450
<212> TYPE: DNA
<213> ORGANISM: Acyrthosiphon pisum

<400> SEQUENCE: 10

```
atggctgatc aactaacaga agaacagatt gccgaattca aagaggcgtt ttcgctattc     60

gacaaggacg gagatggtac catcaccacc aaagaacttg gaaccgtcat gaggtcttta    120

ggccaaaatc cgactgaagc tgaactccaa gatatgatta acgaggtcga tgctgatggc    180

aacggcacga tagatttccc agagttcttg actatgatgg cccgcaaaat gaaggatacc    240

gatagtgagg aagaaatcag agaggctttc cgtgtatttg ataaggatgg aaacggcttt    300

attagtgcag ctgagctgcg tcatgtgatg actaaccttg gagaaaagct caccgatgaa    360

gaggttgatg aaatgatcag ggaagctgac attgatggtg atggtcaagt caactatgaa    420

gagttcgtga ccatgatgac ttctaagtga                                    450
```

<210> SEQ ID NO 11
<211> LENGTH: 441
<212> TYPE: DNA
<213> ORGANISM: Harpegnathos saltator

<400> SEQUENCE: 11

```
caactcacag aggaacagat cgcagagttt aaggaagcct tctcgctatt cgacaaagat     60

ggcgatggca ctataacgac taaagaattg ggtacagtca tgcgatccct gggtcaaaat    120

cccacagagg ccgagttaca agacatgatt aatgaagtag acgcagatgg taacggtaca    180

atcgactttc cggagttctt gaccatgatg gcacgcaaaa tgaaggatac ggacagcgag    240

gaggagatca gggaggcctt cagagtgttc gataaggatg gaaatggttt catatccgca    300

gcggaactca gacatgttat gacaaatctg ggcgagaaac tgaccgatga ggaagtagat    360

gaaatgatac gggaggcaga tatcgacggc gatggccaag tgaattatga agaatttgtg    420

acgatgatga catcaaagtg a                                              441
```

<210> SEQ ID NO 12
<211> LENGTH: 459
<212> TYPE: DNA
<213> ORGANISM: Pediculus humanus corporis

<400> SEQUENCE: 12

```
atggtttctt tttttttgcg agctgatcag ttgaccgaag aacaaattgc cgaattcaag     60

gaagcatttt ccttattcga caaagatggc gatggtacca taacaactaa ggaattgggt    120

acggttatga gatcactcgg tcagaatccc acagaagcag aattacaaga tatgattaat    180

gaagtggatg cagatggtaa tggtaccatc gattttcccg agttcctcac catgatggct    240

agaaaaatga aggatacaga cagcgaagaa gaaattagag aagcattcag agttttcgat    300

aaggatggta atggttttat atcggcagcc gagctaaggc acgtcatgac gaacctgggt    360

gaaaaattaa cagacgaaga agtggatgaa atgattcgag aggctgatat cgacggagat    420

ggacaagtga attacgaaga atttgtggaa aacttgtga                           459

<210> SEQ ID NO 13
<211> LENGTH: 459
<212> TYPE: DNA
<213> ORGANISM: Anopheles gambiae

<400> SEQUENCE: 13

atggccgatc aacttacgga agaacagatc gctgaattca aagaagcgtt ctcgctgttc     60

gacaaggacg gcgatggcac aatcaccacc aaggaattag gcaccgtgat gcgatcgcta    120

ggccagaacc ccacagaagc tgaattgcaa gacatgatca acgaagtcga cgcggacggt    180

aacggcacga tcgatttccc cgagtttcta acaatgatgg ctcgtaaaat gaaggacacg    240

gacagtgaag aggaaatccg ggaggcattc cgagtcttcg acaaggacgg caacggtttt    300

atctctgcag ctgagctgcg ccacgtcatg actaatctgg gcgagaagct aacagacgag    360

gaggtcgacg agatgatccg tgaagccgat atagatggcg atggccaggt taattatgaa    420

ggtaagagtt gcctttcgcg cccacaccaa gcattgttt                           459

<210> SEQ ID NO 14
<211> LENGTH: 501
<212> TYPE: DNA
<213> ORGANISM: Solenopsis invicta

<400> SEQUENCE: 14

atgatcggca cgataacgac gagaaattcc attatttcag aattcaaaga ggcatttatg     60

cttttcgaca aggacgaaga tggcacgatt acgatggcgg aattaggggt tgtcatgcgg    120

tctctcggtc aaagaccgtc ggagacggaa ctgcgcgata tggtgaatga ggtagatcaa    180

gatggaaatg gtaccatcga gtttaacgaa tttctgcaga tgatgtcgaa gaagatgaaa    240

agcgccgacg gagaggacga acttcgcgag gcgttccgag tgttcgataa gaacaacgat    300

ggcttaatat cttcgaaaga gttgcgacac gtaatgacga atcttggtga aaagctctct    360

gaggaggagg tcgatgatat gattaaggag gcggatctag atggcgacgg aatggtcaac    420

tacgaaggta acattttgtt ttgcctagat gtttattcta taatagattt agaatttatt    480

ctaagcgata tagatgaatt g                                              501

<210> SEQ ID NO 15
<211> LENGTH: 364
<212> TYPE: RNA
<213> ORGANISM: Ixodes scapularis

<400> SEQUENCE: 15

aguucaagga ggcguucuuc gcuguucgac aaggacggag gauggcacca ucacgaccaa     60

ggagcugggc acggucaugc gcucgcucgg ccagaacccg acggaggcgg agcugcagga    120
```

caugaucaac gagguggacg cagacggcaa cggaacgauc gacuuccccg aguuccuuac 180
gaugauggcg cgcaagauga aggacacgga cucugaggag gagauccggg aggcguuccg 240
gguguucgac aaggacggca acggcuucau cucugcggcg gagcugcgcc acgucaugac 300
caaccugggc gagaagcuga cggacgagga gguggacgag augauccggg aggcggacau 360
cgac 364

<210> SEQ ID NO 16
<211> LENGTH: 372
<212> TYPE: RNA
<213> ORGANISM: Aedes aegypti

<400> SEQUENCE: 16
gcagauugcc gaauucaaag aagcguuuuc gcuguucgac aaagacggug acggcacaau 60
cacaaccaag gaacugggaa ccgugaugcg aucguuaggc cagaacccca cagaagcaga 120
acugcaagau augauaaacg aagucgacgc ggacggcaac ggcacgaucg auuuccccga 180
auuccugacc augauggcuc gcaaaaugaa ggacaccgau agcgaagagg aaauccggga 240
ggcguuccga gucuucgaca aggacggcaa cggcuucauc ucggcagcug agcugcguca 300
ugucaugacc aaucucggcg agaagcuaac ggacgaggag guggaugaga ugauccgcga 360
agccgacaua ga 372

<210> SEQ ID NO 17
<211> LENGTH: 373
<212> TYPE: RNA
<213> ORGANISM: Culex quinquefasciatus

<400> SEQUENCE: 17
acagaucgcc gaguucaaag aagcguucuc gcuguucgac aaagacggug acggcacgau 60
cacgaccaag gagcugggca ccgugaugcg aucguuaggc cagaacccca cagaagcaga 120
gcugcaagac augauaaacg aggucgaugc ggacggcaac ggcacgaucg acuuccccga 180
guuucucacc augauggcuc gcaaaaugaa ggacaccgau agcgaagagg aaauccggga 240
ggcguuccga gucuucgaca aggacggcaa cggcuucauc ucggcggccg agcugcgcca 300
cgucaugacc aaucucggcg agaagcucac ggacgaggag guggaugaga ugauccgcga 360
ggccgacauu gac 373

<210> SEQ ID NO 18
<211> LENGTH: 372
<212> TYPE: RNA
<213> ORGANISM: Acyrthosiphon pisum

<400> SEQUENCE: 18
acagauugcc gaauucaaag aggcguuuuc gcuauucgac aaggacggag augguaccau 60
caccaccaaa gaacuuggaa ccgucaugag gucuuuaggc caaaauccga cugaagcuga 120
acuccaagau augauuaacg aggucgaugc ugauggcaac ggcacgauag auuucccaga 180
guucuugacu augauggccc gcaaaaugaa ggauaccgau agugaggaag aaaucagaga 240
ggcuuuccgu guauuugaua aggauggaaa cggcuuuauu agugcagcug agcugcguca 300
ugugaugacu aaccuuggag aaaagcucac cgaugaagag guugaugaaa ugaucaggga 360
agcugacauu ga 372

<210> SEQ ID NO 19
<211> LENGTH: 373

```
<212> TYPE: RNA
<213> ORGANISM: Harpegnathos saltator

<400> SEQUENCE: 19

acagaucgca gaguuuaagg aagccuucuc gcuauucgac aaagauggcg auggcacuau     60

aacgacuaaa gaauugggua cagucaugcg aucccugggu caaaauccca cagaggccga    120

guuacaagac augauuaaug aaguagacgc agaugguaac gguacaaucg acuuuccgga    180

guucuugacc augauggcac gcaaaaugaa ggauacggac agcgaggagg agaucaggga    240

ggccuucaga guguucgaua aggauggaaa ugguuucaua uccgcagcgg aacucagaca    300

uguuaugaca aaucugggcg agaaacugac cgaugaggaa guagaugaaa ugauacggga    360

ggcagauauc gac                                                       373

<210> SEQ ID NO 20
<211> LENGTH: 373
<212> TYPE: RNA
<213> ORGANISM: Pediculus humanus corporis

<400> SEQUENCE: 20

acaaauugcc gaauucaagg aagcauuuuc cuuauucgac aaagauggcg augguaccau     60

aacaacuaag gaauugggua cgguuaugag aucacucggu cagaauccca cagaagcaga    120

auuacaagau augauuaaug aaguggaugc agaugguaau gguaccaucg auuuucccga    180

guuccucacc augauggcua gaaaaaugaa ggauacagac agcgaagaag aaauuagaga    240

agcauucaga guuuucgaua aggaugguaa ugguuuuaua ucggcagccg agcuaaggca    300

cgucaugacg aaccugggug aaaaauuaac agacgaagaa guggaugaaa ugauucgaga    360

ggcugauauc gac                                                       373

<210> SEQ ID NO 21
<211> LENGTH: 372
<212> TYPE: RNA
<213> ORGANISM: Anopheles gambiae

<400> SEQUENCE: 21

acagaucgcu gaauucaaag aagcguucuc gcuguucgac aaggacggcg auggcacaau     60

caccaccaag gaauuaggca ccgugaugcg aucgcuaggc cagaacccca cagaagcuga    120

auugcaagac augaucaacg aagucgacgc ggacgguaac ggcacgaucg auuuccccga    180

guuucuaaca augauggcuc guaaaaugaa ggacacggac agugaagagg aaauccggga    240

ggcauuccga gucuucgaca aggacggcaa cgguuuuauc ucugcagcug agcugcgcca    300

cgucaugacu aaucugggcg agaagcuaac agacgaggag gucgacgaga ugauccguga    360

agccgauaua ga                                                        372

<210> SEQ ID NO 22
<211> LENGTH: 364
<212> TYPE: RNA
<213> ORGANISM: Solenopsis invicta

<400> SEQUENCE: 22

cagaauucaa agaggcauuu augcuuuucg acaaggacga agauggcacg auuacgaugg     60

cggaauuagg gguugucaug cggucucucg gucaaagacc gucggagacg gaacugcgcg    120

auauggugaa ugagguagau caagauggaa augguaccau cgaguuuaac gaauuucugc    180

agaugauguc gaagaagaug aaaagcgccg acggagagga cgaacuucgc gaggcguucc    240
```

```
gaguguucga uaagaacaac gauggcuuaa uaucuucgaa agaguugcga cacguaauga    300

cgaaucuugg ugaaaagcuc ucugaggagg aggucgauga uaugauuaag gaggcggauc    360

uaga                                                                 364


<210> SEQ ID NO 23
<211> LENGTH: 373
<212> TYPE: RNA
<213> ORGANISM: Varroa destructor

<400> SEQUENCE: 23

acagguggcu gaauuuaaag aggccuuucu uuuguuugac aaggacgccg auggaaugau     60

uacggccgcc gaacuaggcg ucgucaugcg aucgcuuggc cagcgaccua cggagcaaga    120

gcucaagaaa augguuacca ugguugacca ggacggcaau gguacaaucg aguucaacga    180

guuuuugaug augaugucuc gcaagaugaa ggaggcagac ucggaggaag aacuccggga    240

ggcguuccgu guguucgauc gagacgguga cggauucauc ucgcgggacg agcucagugu    300

cgucaugaac aaccucggcg agaaauuaag ugacgaugau guugaggaua ugauucgaga    360

ggccgaucug gac                                                       373


<210> SEQ ID NO 24
<211> LENGTH: 627
<212> TYPE: DNA
<213> ORGANISM: Tetranychus urticae

<400> SEQUENCE: 24

attcatcaga tttaaaatta ttcaccttgt acctgaatta aaacaatagt attatataag     60

atggctgacc agctaactga agagcaaatt gctgaattta aggaggcctt ttcattgttt    120

gataaagatg gtgatggtac aattaccacc aaggaattgg gaactgttat gagaagtcta    180

ggtcaaaatc caacagaagc ggaattacaa gatatgatca atgaagttga tgccgatggt    240

aatggtacta ttgattttcc tgaattcttg actatgatgg ctagaaaaat gaaggataca    300

gactcagagg aggaaatccg tgaagctttc cgtgtttttg ataaagatgg taatggtttt    360

atttctgctg ctgaattgag acatgtaatg accaatttgg gtgaaaaatt gaccgacgaa    420

gaagtagatg aaatgattcg tgaagccgat attgacggtg atggtcaagt taattatgaa    480

gaatttgtaa cgatgatgac atccaaatga ataaaagcac aaggttaatt gttcatttta    540

attagatcca atggatccca tcagtgacag ggataaaaat taatcaataa aagatgaaaa    600

gcaaaaaata catggaagct atcatca                                        627


<210> SEQ ID NO 25
<211> LENGTH: 372
<212> TYPE: RNA
<213> ORGANISM: Tetranychus urticae

<400> SEQUENCE: 25

caaauugcug aauuuaagga ggccuuuuca uuguuugaua aagaugguga ugguacaauu     60

accaccaagg aauugggaac uguuaugaga agucuagguc aaaauccaac agaagcggaa    120

uuacaagaua ugaucaauga aguugaugcc gaugguaaug guacuauuga uuuuccugaa    180

uucuugacua ugauggcuag aaaaaugaag gauacagacu cagaggagga aauccgugaa    240

gcuuuccgug uuuuugauaa agaugguaau gguuuuauuu cugcugcuga auugagacau    300

guaaugacca auuuggguga aaaauugacc gacgaagaag uagaugaaau gauucgugaa    360

gccgauauug ac                                                        372
```

<210> SEQ ID NO 26
<211> LENGTH: 1114
<212> TYPE: DNA
<213> ORGANISM: Varroa destructor
<220> FEATURE:
<221> NAME/KEY: unsure
<222> LOCATION: (1)..(1114)
<223> OTHER INFORMATION: unsure at all n locations
<220> FEATURE:
<221> NAME/KEY: misc_feature
<222> LOCATION: (1100)..(1110)
<223> OTHER INFORMATION: n is a, c, g, or t

<400> SEQUENCE: 26

```
ggctcgtaca ccgagagaga acggtggact ccattgctgt cctgagtgcg tttctcgtcg     60

gctgtgtcgt attgcgtgtc tgtccgtgct ttcgtgcaca taagttttct ttccacattg    120

gagatattgt gaatagtatc ctttgtgttt agtgcctgaa caatatttga aatcgtcgaa    180

cgtatcaaga cataaaaacg agccaaaatg gctgatcaac ttacggaaga acaaatcgca    240

gaatttaagg aagcattttc actatttgat aaagatggag atggtaccat cacaactaaa    300

gagttgggta cagttatgcg atcactaggt caaaatccca cagaagctga gcttcaggat    360

atgattaatg aagttgatgc agatggtaat ggcacaatcg attttccgga attcttaact    420

atgatggctc gtaaaatgaa agatactgat agtgaggaag aaattaggga ggccttcaga    480

gtatttgata aggatggaaa tggtttcata tccgcagcag aactcagaca tgttatgaca    540

aatcttggcg agaaactcac tgatgaagaa gttgatgaaa tgattcggga ggctgacatt    600

gatggtgatg gccaagttaa ttatgaagaa ttcgtcacaa tgatgacatc aaagtgaatg    660

caacctgtgt aatggaaaaa cttgcaactt ggagtggtgt tgacgtatta agataaatca    720

agaaacaaag aaaaatataa tgttaacaaa aaacgaatcg accagaaagt gaaaaaaatc    780

ttgtatctgg acgcaaagat gtctataaaa cgcgaaaaat taacgtccaa cacgcgttaa    840

tcatcattaa cgataagtaa tacagggcaa ttgtttaatt aaaagagtta taccactaaa    900

aatcattatc tctaaataca caaaacttaa ttacacaaca tgaacataaa aatacatatt    960

actcgcgcac atacatgaat acaaaaaaat atacagcaca cagaaatacc atctacataa   1020

aagataattt atttccgtat taaaaagtat ataattaaaa aatgttagag atatatatat   1080

ataatatata tatatatatn nnnnnnnnnn gtaa                               1114
```

<210> SEQ ID NO 27
<211> LENGTH: 372
<212> TYPE: RNA
<213> ORGANISM: Varroa destructor

<400> SEQUENCE: 27

```
acaaaucgca gaauuuaagg aagcauuuuc acuauuugau aaagauggag augguaccau     60

cacaacuaaa gaguugggua caguuaugcg aucacuaggu caaaauccca cagaagcuga    120

gcuucaggau augauuaaug aaguugaugc agaugguaau ggcacaaucg auuuuccgga    180

auucuuaacu augauggcuc guaaaaugaa agauacugau agugaggaag aaauuaggga    240

ggccuucaga guauuugaua aggauggaaa ugguuucaua uccgcagcag aacucagaca    300

uguuaugaca aaucuuggcg agaaacucac ugaugaagaa guugaugaaa ugauucggga    360

ggcugacauu ga                                                        372
```

<210> SEQ ID NO 28

<211> LENGTH: 822
<212> TYPE: DNA
<213> ORGANISM: Varroa destructor

<400> SEQUENCE: 28

```
tttttttttt ttttcgaaga aatcgtatca tcgaacatcg gatcgaattt cgatccacga     60

cgctcgaatt acatgcaacg aagtgaatgt cagagggggg ggggcagggg aaaagtatgc    120

gacgaacgtg tacgtccgtc gtccgctggc tcgtcgttaa ttcgttctat ctaacacaga    180

cacgagaata agtaagatcc tagtagcccg gggacagcac ctcctcctcc tcgtcctcct    240

cgtcgtcgtc gatccccggc tctccgagcg cgtggacgaa ttcgtagaaa tcgatacggc    300

cgtctccgtc cacgtccact tccttgatca tatcctcgat ctcttcttcc gacaagtcct    360

cgccgagaca ttgcagcact gccctcaaat cggatgcggt gatgtatcct cgattgtgtt    420

tatcgaatac ccggaacgca tccctcagct cctgctcttc ctgatcctga tccgtggggg    480

cggtttcatt cgcacctatg ttgctcacga tttccacgaa ctcttcgaag ctgacatttc    540

catccccgtc gatgtcgatc tcctgcaaca tggtgcgcag ctcctcggcc ctcgcgaatt    600

gccccaacga gcgcatcacc ctcccgagct cctccttcgt gatgctcccg tccccgtcct    660

tgtcgaacag tctgaacgct tccctgaatt ctttcatttg agatttggat atattgctcg    720

gtatcttggt ggacgactca gaggcggatt ttttcggcga cgcaggtaag gagaagagga    780

cgttggtcga caatttgccg gcctccgtgg acgaggaggc cg                       822
```

<210> SEQ ID NO 29
<211> LENGTH: 300
<212> TYPE: RNA
<213> ORGANISM: Varroa destructor

<400> SEQUENCE: 29

```
aacguguacg uccgucgucc gcuggcucgu cguuaauucg uucuaucuaa cacagacacg     60

agaauaagua agauccuagu agcccgggga cagcaccucc uccuccucgu ccuccucguc    120

gucgucgauc cccggcucuc cgagcgcgug gacgaauucg uagaaaucga uacggccguc    180

uccguccacg uccacuuccu ugaucauauc cucgaucucu ucuuccgaca aguccucgcc    240

gagacauugc agcacugccc ucaaaucgga ugcggugaug uauccucgau uguguuuauc    300
```

<210> SEQ ID NO 30
<211> LENGTH: 2577
<212> TYPE: DNA
<213> ORGANISM: Varroa destructor

<400> SEQUENCE: 30

```
ctgctgctgc tgctgctgct gctgctgccg tgttaagaac tagacaaagg caacaaccgg     60

aagacatctg ttaggccagt tgggtgaagg gaaataaact cgcaacaaag agctactgtt    120

gcaaaagcta tctgttctga gtcctagact agactgggat cgactaacaa ctctgcaggc    180

cgtggaccac tatcactgaa caacgccgca ggaccgagcg attgagaagt tggccgcggc    240

tgggacgctc tggctcactt gatctgatta ctacttacac caggtcaatt taaccaagcc    300

gttgaaccac tcctacatgg aaacacacat ctacactctc atccaattgt gtacacgcga    360

agcaaacgac aacggtatta gcagcgacac taacaaaaac gaatctgcca gaaaccgagt    420

aacgctgatt tctgcagcgg cgttcctacg aacttaccac agacccggtc ggcacaatag    480

tttgaaggtt agcatcggcc cgtgaactat agtgaaagga actgagcgaa atactatagt    540

tgttgaacag caggcttcaa agtaaagaag tgaatattct tatggtgaca acaaattttg    600
```

```
tctgtagtgg tcaagaccct actcaatgaa gtgagaagcg aattcatatg tgctcagtta    660
tagcagttgt ttgtcgtaat gccgccaata tacgacgtct gtgtgtctcg atactggcgt    720
atctgactga ttccgatcgg tgtcattgat ctgcaaagcc aattgttttc tttacgtccc    780
ggatagagca aacgatcatg gcaacggaaa catttggcct gccggaggaa caggtggctg    840
aatttaaaga ggcctttctt ttgtttgaca aggacgccga tggaatgatt acggccgccg    900
aactaggcgt cgtcatgcga tcgcttggcc agcgacctac ggagcaagag ctcaagaaaa    960
tggttaccat ggttgaccag gacggcaatg gtacaatcga gttcaacgag tttttgatga   1020
tgatgtctcg caagatgaag gaggcagact cggaggaaga actccgggag gcgttccgtg   1080
tgttcgatcg agacggtgac ggattcatct cgcgggacga gctcagtgtc gtcatgaaca   1140
acctcggcga gaaattaagt gacgatgatg ttgaggatat gattcgagag gccgatctgg   1200
acggcgatgg caagattaac taccaagagt ttgtgctcat tatcacctcc gccaagtagg   1260
ccttggagtt gctcgcgcac acacatgcta ttcctcttgt cctacacgac aaacactata   1320
cacgttacaa tacggaaaaa tgaaataaaa gcacagtcac acttattcat tcattcacag   1380
aggatcactg gcgtgtcctc attaatatgg ctgacaaata ctattgattt gtctcgactg   1440
agctatcagg cacacgcata ttgtctgttc cgatacgtgc aataataggt aaagtggtgt   1500
tagcttgagc accttacggt ttacatttat tccgtattaa cggtactatg tctcaatagt   1560
catgtcgcag cattagccag ctaacattaa atttagttga tttttatttt attttttttac  1620
acaacaagaa ttatcttact atttggcaag ctgactgcga gtagtaaaat taccctagta   1680
aaaaaaaaag gctttaaaaa cgatttaaca aaggtgcgtc catttaaaaa agtatgacac   1740
aagctaatgt gttcgatcgc ggtcggttgc attcggccag tttgtgagac gcgaaattta   1800
ccagcagccg tcaacaacga tggaataatt atatattaaa tataaataat aaaatatctg   1860
ttacacattc tatgtgaata aagttataca tatatatata catacaacag caatgatata   1920
tatgatgata cgtatactat atagaagtat ccactgatat aggataatgg gaaattctgg   1980
aaaggagaaa acatattctt ctttcataat taatgaatta tcatcgagca cctcaagaat   2040
ttgcttagac atattacaaa aaaaaaatta attcactata tataaataat cgcaattaat   2100
caaaaaaaaa atacggtcat ttatggcata ccctaggtta ataaacttca taaaggtacc   2160
tatatatata tcttttttac tgtctcttta atcgtcatta tacatagtga cgattaaaga   2220
gagagagtaa aaaagaggtc aaaataaaag acttgaagtc gattgaggtt aatttttatt   2280
ctaggttata tgtgttttag cggatttata gtgtgctcgt tgtaaaagtt gacgtaagga   2340
gttgaaacgc ggagagcagt ataacagtaa aatggagagg aagtttagaa gttgggaaat   2400
aaatgatttg ctactaattg gaaattacaa aaatgaccat ttaaagaact tatcattaga   2460
attttaatat ctgccacact gaaccgtttt gtcattattt cgaccatagc gattttcaca   2520
cagttgtctc acgtttgagg ccttatcgtt taaaggctaa cggaaatttc tctaaag      2577
```

<210> SEQ ID NO 31
<211> LENGTH: 373
<212> TYPE: RNA
<213> ORGANISM: Varroa destructor

<400> SEQUENCE: 31

```
acagguggcu gaauuuaaag aggccuuucu uuuguuugac aaggacgccg auggaaugau     60
uacggccgcc gaacuaggcg ucgucaugcg aucgcuuggc cagcgaccua cggagcaaga    120
```

```
gcucaagaaa augguuacca ugguugacca ggacggcaau gguacaaucg aguucaacga    180

guuuuugaug augaugucuc gcaagaugaa ggaggcagac ucggaggaag aacuccggga    240

ggcguuccgu guguucgauc gagacgguga cggauucauc ucgcgggacg agcucagugu    300

cgucaugaac aaccucggcg agaaauuaag ugacgaugau guugaggaua ugauucgaga    360

ggccgaucug gac                                                      373
```

<210> SEQ ID NO 32
<211> LENGTH: 693
<212> TYPE: DNA
<213> ORGANISM: Varroa destructor

<400> SEQUENCE: 32

```
cgcctctata cagtgaaaaa gtcggataag gttatgttac tcagtaactt aaccttatct     60

tggataacgt tatttgacac gtaaacgaaa agtaataaca aagttttgta ttatggctcg    120

ttattttcga gaggaagata tagatgaatt cagggaatgt ttttatctat ttgcaaggaa    180

tggtcaaata cgtactttgg atgagcttac aatcattatg agatcattag gattaagtcc    240

aactattgca gaattaaata aatatttgaa agataaaggt ggaaaaatgt cttttgccga    300

tttcttggaa gttatgcatc tacaaactag agctgaagat ttaccaaaag aagtgataga    360

tgcttttcaa gctgcagata aatttaggac tggcactata ccagctagac agttagcgca    420

tatgttactc cactggggtg aacaattaag taacaaagaa gtggagcaaa ttttcagaga    480

ggcaaatgtg tctccaaatg gacaagtaaa gtacgaagat tttgttaaaa tagcttgtgc    540

acctgtacct gattactatt aaaataaata tttttcatat tttttaaaga tatttatata    600

ctttttacac aatacacacg tatttaatta ataaaaggat aaaaatgatc ataaaagaaa    660

aagaatttat tcttccagca acttatcttc gac                                693
```

<210> SEQ ID NO 33
<211> LENGTH: 315
<212> TYPE: RNA
<213> ORGANISM: Varroa destructor

<400> SEQUENCE: 33

```
augcuuuuca agcugcagau aaauuuagga cuggcacuau accagcuaga caguuagcgc     60

auauguuacu ccacuggggu gaacaauuaa guaacaaaga aguggagcaa auuuucagag    120

aggcaaaugu gucuccaaau ggacaaguaa aguacgaaga uuuuguuaaa auagcuugug    180

caccuguacc ugauuacuau uaaaauaaau auuuuucaua uuuuuuaaag auauuuauau    240

acuuuuuaca caauacacac guauuuaauu aauaaaagga uaaaaaugau cauaaaagaa    300

aaagaauuua uucuu                                                    315
```

<210> SEQ ID NO 34
<211> LENGTH: 612
<212> TYPE: DNA
<213> ORGANISM: Varroa destructor

<400> SEQUENCE: 34

```
cgttttttta atttcaaaga ctcctgattt tcttttcttt tcctttccta caaaccaaac     60

acaagctaga aagaggttcg atttttgcag gaagaagaag gaacaatggc tgatcagctc    120

accgatgacc agatctctga gtttaaggaa gccttcagcc tcttcgataa ggatggagat    180

ggttgtatca ccaccaagga gcttggaact gtgatgaggt ctcttggcca gaaccccact    240

gaggcagagc tccaggacat gatcaacgag gtggatgctg atggcaatgg aacaattgac    300
```

```
tttcctgagt tcttaaacct catggccagg aagatgaagg atactgattc tgaggaggag    360

ctcaaggaag ctttccgcgt gtttgacaag gaccagaatg gcttcatttc tgcggctgag    420

ctccgccatg ttatgacgaa tcttggtgag aagctcacag acgaggaagt tgatgagatg    480

atccgtgagg ctgatgtaga tggtgacggc cagattaact acgaggagtt tgtcaaagtc    540

atgatggcca agtgaggatc attaaccaaa ccttaaaatt tcgaaagcat aaacatttaa    600

aaaaaaaaaa aa                                                        612
```

<210> SEQ ID NO 35
<211> LENGTH: 371
<212> TYPE: RNA
<213> ORGANISM: Varroa destructor

<400> SEQUENCE: 35

```
cagaucucug aguuuaagga agccuucagc cucuucgaua aggauggaga ugguuguauc     60

accaccaagg agcuuggaac ugugaugagg ucucuuggcc agaaccccac ugaggcagag    120

cuccaggaca ugaucaacga gguggaugcu gauggcaaug gaacaauuga cuuuccugag    180

uucuuaaacc ucauggccag gaagaugaag gauacugauu cugaggagga gcucaaggaa    240

gcuuuccgcg uguuugacaa ggaccagaau ggcuucauuu cugcggcuga gcuccgccau    300

guuaugacga aucuugguga gaagcucaca gacgaggaag uugaugagau gauccgugag    360

gcugauguag a                                                         371
```

<210> SEQ ID NO 36
<211> LENGTH: 659
<212> TYPE: DNA
<213> ORGANISM: Ixodes scapularis

<400> SEQUENCE: 36

```
acaccgcgct cgacgagaac tcgcgcaagg agcgcgtgct aacgccgata gctctcgtac     60

aaaagaaaac taaagacttg acacgctcaa taccgatctt tcacattttc agcaaaattt    120

gagcattccg aatatggacc tgactccgga agagatcgcg gacatcaagg gagcgtttct    180

gctgtttgac cgcaacggcg acggaaccat ctccacgact gagctagaga tggtcctccg    240

cgccatgggc gaacggccca gtccttccca gctggcccgt atagtgcggc aaattgacag    300

cgaccgcaat ggaagcatcg acttccaaga gtttctcttt ttcatggccg gcaggatttc    360

ccacaaaggc ctctccaaaa gcgcagtcct caaggccttc caactcttcg accgcgatgg    420

caatggatac atcaccaggg aggaactcgt ccacattttc acgcacgttg ggcagagcat    480

gagccaagaa gacgccgaaa agataatccg cgaagtggat gtggacaagg acggaaagat    540

ccattacact gaattggtca acaaggtgct gcccaccaag aagcaaaaag aagaaaccaa    600

aacctagaag gtcgtcgctt ggcacggtct ttattattaa acaagtgctt tatcgcttg     659
```

<210> SEQ ID NO 37
<211> LENGTH: 374
<212> TYPE: RNA
<213> ORGANISM: Ixodes scapularis

<400> SEQUENCE: 37

```
agaucgcgga caucaaggga gcguuucugc uguuugaccg caacggcgac ggaaccaucu     60

ccacgacuga gcuagagaug guccuccgcg ccaugggcga acggcccagu ccuucccagc    120

uggcccguau agugcggcaa auugacagcg accgcaaugg aagcaucgac uuccaagagu    180
```

```
uucucuuuuu cauggccggc aggauuuccc acaaaggccu cuccaaaagc gcaguccuca    240

aggccuucca acucuucgac cgcgauggca auggauacau caccagggag gaacucgucc    300

acauuuucac gcacguuggg cagagcauga gccaagaaga cgccgaaaag auaauccgcg    360

aaguggaugu ggac                                                      374
```

<210> SEQ ID NO 38
<211> LENGTH: 549
<212> TYPE: DNA
<213> ORGANISM: Ixodes scapularis

<400> SEQUENCE: 38

```
gattcgtcca cttattttgt ccctattctt cgtccgcagt cgtcctcgag gaaaagtgcg     60

tcaggtgcgg gctacaagcg gaaactgagc ggaaagccag aaccgagcga ggagcagaag    120

aatgacatga aggaagcgtt cagtctcttc gatcccagtg gcacgggctt catggagtct    180

aaagatatga agtttgcaat gagagcactg ggttttgaac caaaaaagga ggaagtgaaa    240

aaactgatag cagagattga caagcagggg actggaaaaa ttcccttgga ggagttcatg    300

agcgtcatgt ccacgaggct ggctgagaaa gacataaatg aggagattat gaaggcgttt    360

cagctgtttg atgaggatgg cactgggaag atttctttta agaacctcaa gaatgtggcc    420

aaggaactgt cggagaacct cacagatgag gagcttcagg aaatgatcaa tgaagctgac    480

agggatggag atggcgaagt gaaccaagag gagttcctta ggataatgaa gaagacctgc    540

ctctactga                                                            549
```

<210> SEQ ID NO 39
<211> LENGTH: 373
<212> TYPE: RNA
<213> ORGANISM: Ixodes scapularis

<400> SEQUENCE: 39

```
ugaaggaagc guucagucuc uucgauccca guggcacggg cuucauggag ucuaaagaua     60

ugaaguuugc aaugagagca cuggguuuug aaccaaaaaa ggaggaagug aaaaaacuga    120

uagcagagau ugacaagcag gggacuggaa aaauucccuu ggaggaguuc augagcguca    180

uguccacgag gcuggcugag aaagacauaa augaggagau uaugaaggcg uuucagcugu    240

uugaugagga uggcacuggg aagauuucuu uuaagaaccu caagaaugug gccaaggaac    300

ugucggagaa ccucacagau gaggagcuuc aggaaaugau caaugaagcu gacagggaug    360

gagauggcga agu                                                       373
```

<210> SEQ ID NO 40
<211> LENGTH: 234
<212> TYPE: DNA
<213> ORGANISM: Ixodes scapularis

<400> SEQUENCE: 40

```
atggccaaga acgtccgcgc cctggacacc gaggaggaga ttttggaggc cttcaaagtc     60

ttcgaccgca acggcgacgg cttcgtgagc acagccgagc tccgtcacgt gatgaccacg    120

ttaggcgaga agttgacgca cgaagaagtg gacgagatga tccgcgaggc cgaccgcgac    180

ggcgacggac agatcaacta cgacgagttc gtggccatga tgacttccaa gtga          234
```

<210> SEQ ID NO 41
<211> LENGTH: 213
<212> TYPE: DNA
<213> ORGANISM: Ixodes scapularis

<400> SEQUENCE: 41

```
cctggaaccg aggaggagat tctggaggcc ttcaaagtct tcgaccgcaa cggcgacggc     60

ttcgtgagca cggccgagct ccgtcacgtg atgaccacgc taggcgagaa gttgacgcac    120

gaagaagtgg acgagatgat ccgcgaggcc gaccgtgacg gcgacggaca gatcaactac    180

gacgagttcg tggccatgat gacctccaag tga                                 213
```

<210> SEQ ID NO 42
<211> LENGTH: 200
<212> TYPE: RNA
<213> ORGANISM: Ixodes scapularis

<400> SEQUENCE: 42

```
gaggaggaga uucuggaggc cuucaaaguc uucgaccgca acggcgacgg cuucgugagc     60

acggccgagc uccgucacgu gaugaccacg cuaggcgaga aguugacgca cgaagaagug    120

gacgagauga uccgcgaggc cgaccgugac ggcgacggac agaucaacua cgacgaguuc    180

guggccauga ugaccuccaa                                                200
```

<210> SEQ ID NO 43
<211> LENGTH: 450
<212> TYPE: DNA
<213> ORGANISM: Aedes aegypti

<400> SEQUENCE: 43

```
atgtccgccc atagtctaac agaggaacaa gggcgccagt tccgtcagat gttcgagatg     60

ttcgacaaaa atggcgacgg ttcgatcagc acatcggaac tgggatcggt cattcgggcc    120

ttgggtatga atccctccat tgcggaaatc gagcaaatga tccacgaggt cgatttggac    180

ggaagtgggt cgattgagtt gaacgaattt ctcatactga tggcacgtaa gtcacgggag    240

ggttccacac aggaagagct acgggatgcg ttcaaaattt ttgacaagga tggagatgga    300

tttctcacgg ttgacgagtt gtcggctgtt atgaagaact ttggcgagag attgaccgat    360

gacgaactag cagatctgct ggaggaagcc gacatcgatg gagacggaaa gatcaactat    420

gaagaatttg tcatcatgtt gagcaagtga                                     450
```

<210> SEQ ID NO 44
<211> LENGTH: 300
<212> TYPE: RNA
<213> ORGANISM: Aedes aegypti

<400> SEQUENCE: 44

```
acagaggaac aagggcgcca guuccgucag auguucgaga uguucgacaa aaauggcgac     60

gguucgauca gcacaucgga acugggaucg gucauucggg ccuuggguau gaaucccucc    120

auugcggaaa ucgagcaaau gauccacgag gucgauuugg acggaagugg gucgauugag    180

uugaacgaau uucucauacu gauggcacgu aagucacggg aggguuccac acaggaagag    240

cuacgggaug cguucaaaau uuuugacaag gauggagaug gauuucucac gguugacgag    300
```

<210> SEQ ID NO 45
<211> LENGTH: 465
<212> TYPE: DNA
<213> ORGANISM: Aedes aegypti

<400> SEQUENCE: 45

```
atgtccgccc aaaccccgcc agacaagctt tcccaggatc aaatcgaaga actgcgggaa     60
```

```
gctttctccc tgttcgacac caacggcgac ggaaccataa cctgttcaga acttggcaca    120

gtccttcgat cccttggcaa aaatgtatcc gacgcggaag tggaagaact gctcaaagaa    180

gtcaacgtcg accacgaagg aatgatccac tttccggact tcgtggcaat gatgtccatc    240

cgattgcggg acttcaatag cgaggaggaa ctcaaggaag ccttccggat cttcgaccgc    300

aacggagatg ggctgatttc ggcggacgaa ttgcgagcgg ctctccaatc tttcggggaa    360

cagctggccg aggaggaaat cgaagaactg ctccgggagg cggatgtcaa ctgcgacgga    420

caaatagact acgaggagtt tgttaaaatg atcacgctga aataa                    465
```

<210> SEQ ID NO 46
<211> LENGTH: 300
<212> TYPE: RNA
<213> ORGANISM: Aedes aegypti

<400> SEQUENCE: 46

```
caaaucgaag aacugcggga agcuuucucc cuguucgaca ccaacggcga cggaaccaua     60

accuguucag aacuuggcac aguccuucga ucccuuggca aaaauguauc cgacgcggaa    120

guggaagaac ugcucaaaga agucaacguc gaccacgaag gaaugaucca cuuuccggac    180

uucguggcaa ugauguccau ccgauugcgg gacuucaaua gcgaggagga acucaaggaa    240

gccuuccgga ucuucgaccg caacggagau gggcugauuu cggcggacga auugcgagcg    300
```

<210> SEQ ID NO 47
<211> LENGTH: 1150
<212> TYPE: DNA
<213> ORGANISM: Aedes aegypti

<400> SEQUENCE: 47

```
tcgtcaagga tatccggcaa ctgattatga cccggcaaac caacgatccc aacggccagc     60

aacaggaaca gaacgaacca gaatccagtc agaacaccca gagcgaccaa agcaacaacc    120

agcccacgca gcgattggga ggaaccacct cggacttcag tgtcagctcc gcggccacta    180

atcgaagtat gccccgccac caggaggaca atcccaatca accggccagc gactgttcca    240

gcctcgaggg aaatgtattc gtcgaaggcg gatccggcac cggagcgcac ccgaaaacac    300

gccgctcgca aacttccgat tcgatcacct ccagcaactt caactacagt ctcaaccgga    360

ggttcatatc gaagaaccag atgaaggagt ttcgagaagc gttccggctg ttcgacaagg    420

ataatgacgg ctcaatcacc aaggaagaac tgggaactgt catgaggtcg ttgggacaat    480

ttgctcgcgt ggaagaatta caagagatgt tactggagat tgatgttgat ggcgatggaa    540

acgtaagttt cgaagagttt gtcgacatca tgtccaacat gacggatacc gtggcggaaa    600

catcggccga ccaggaggaa cgtgagctac gtgatgcctt ccgtgtcttc gacaagcaca    660

atcgaggtta cattacggca tcagatctac gggcggttct tcaatgtctg ggcgaagatt    720

tggatgaaga agaaattgaa gacatgatca aagaagtgga cgtggatgga gacggacgga    780

tcgatttcta cgaattcgta catgctcttg gagaaccgga agattcccaa gaaaacgacg    840

acgaagacga ggcagtgtcc ccccattcgc tgtcctgtga cgtgcatgtc taagaaccgc    900

caggagaaaa atagctaacg ccaacgaatc gcattcctaa caaaatgtcg aacaatctag    960

agacattgac cagatttttt ttaaatattt aacacacaaa aaaacttcgc ttaacgccat   1020

tgtacttctc catacgcttg ataacagatt ccagaacacc taatgaattt atcaatctat   1080

acataataac tattcatctc taatcacgaa aaaagtttaa ataaacatat caaattgagc   1140

aaccaataag                                                          1150
```

<210> SEQ ID NO 48
<211> LENGTH: 300
<212> TYPE: RNA
<213> ORGANISM: Aedes aegypti

<400> SEQUENCE: 48
gaguuucgag aagcguuccg gcuguucgac aaggauaaug acggcucaau caccaaggaa 60
gaacugggaa cugucaugag gucguuggga caauuugcuc gcguggaaga auuacaagag 120
auguuacugg agauugaugu ugauggcgau ggaaacguaa guuucgaaga guuugucgac 180
aucaugucca acaugacgga uaccguggcg gaaacaucgg ccgaccagga ggaacgugag 240
cuacgugaug ccuuccgugu cuucgacaag cacaaucgag guuacauuac ggcaucagau 300

<210> SEQ ID NO 49
<211> LENGTH: 450
<212> TYPE: DNA
<213> ORGANISM: Culex quinquefasciatus

<400> SEQUENCE: 49
atgtcggccc actcgctcac cgacgaacag cagcgccagt accggcaaat gttcgaaacg 60
ttcgacaagg atggcaacgg ttccatcacg acgacggaac tgggaacgct agtgcgagcg 120
ctaggtctta atccttcgat cgccgagatc gagcagatga tccacgaggt cgacctggac 180
ggaagcggga cgatcgagct gaacgagttt tacgtgctga tggcccggaa gcatcgggaa 240
gcctcgtcgg aggacgagct gaggcaggct ttcaaggtgt ttgacaagaa cgaggatggg 300
ttcttgacgg tggaggaact gtcgatggtg atgaagaact tggtgagcg gttgagcgat 360 gaagagttgg cggatttgtt ggaggaggcg gatgttgaca aggacggtcg gattaattac 420
gaggaatttg tgaccatgtt gaccaagtag 450

<210> SEQ ID NO 50
<211> LENGTH: 300
<212> TYPE: RNA
<213> ORGANISM: Culex quinquefasciatus

<400> SEQUENCE: 50
acagcagcgc caguaccggc aaauguucga aacguucgac aaggauggca acgguuccau 60
cacgacgacg gaacugggaa cgcuagugcg agcgcuaggu cuuaauccuu cgaucgccga 120
gaucgagcag augauccacg aggucgaccu ggacggaagc gggacgaucg agcugaacga 180
guuuuacgug cugauggccc ggaagcaucg ggaagccucg ucggaggacg agcugaggca 240
ggcuuucaag guguuugaca agaacgagga uggguucuug acgguggagg aacugucgau 300

<210> SEQ ID NO 51
<211> LENGTH: 477
<212> TYPE: DNA
<213> ORGANISM: Culex quinquefasciatus

<400> SEQUENCE: 51
atgtcatcgt cttcccgcca ccccaaaccc accgcggacc ccctgaccaa ggagcaaatc 60
gaagaactgc gcgaagcgtt caccctgttc gacaccaacg gcgacggaac gatttccggc 120
tcggaactgt ccaccgtgct gcgggccctc ggcaagaacg tctcggacgc cgaagtcgag 180
gaactgctga aggaggtccg caccgacgac gagggccgca tccggttcgg ggactttgtg 240
gccatgatga cggtccggtt gaaggacttt aacaacgagg accagctgca ggaggcgttt 300

```
cggatcttcg atcgggacgg gaatgggcgg atttcggcgg aagagctacg ggtcgcgttg    360

aggtcgtttg gggagcagtt gaccgaagag gagctggagg agttgctgcg cgaggcggac    420

gtcaacagtg acggccagat tgactacggg gagtttgtgc ggatgataac gcagtga       477


<210> SEQ ID NO 52
<211> LENGTH: 300
<212> TYPE: RNA
<213> ORGANISM: Culex quinquefasciatus

<400> SEQUENCE: 52

gcgaagcguu cacccuguuc gacaccaacg gcgacggaac gauuuccggc ucggaacugu     60

ccaccgugcu gcgggcccuc ggcaagaacg ucucggacgc cgaagucgag gaacugcuga    120

aggagguccg caccgacgac gagggccgca uccgguucgg ggacuuugug gccaugauga    180

cgguccgguu gaaggacuuu aacaacgagg accagcugca ggaggcguuu cggaucuucg    240

aucgggacgg gaaugggcgg auuucggcgg aagagcuacg ggucgcguug aggucguuug    300


<210> SEQ ID NO 53
<211> LENGTH: 927
<212> TYPE: DNA
<213> ORGANISM: Culex quinquefasciatus

<400> SEQUENCE: 53

atgaccgatt ttctccagct tccccaatgc aatactcgac aaaccaacga cccaaacagc     60

gccgagcagc aacaacagag cgaacccgaa tcgaaccaga gcagcacgca ccagagcagc    120

agccacagct accagcagcc gtcgtcaacg cagcaccggt tggccggatc tccgtcgagc    180

agtgccaacg cgagtcccgt gatcggccgg aacatgcccc gccaccagca ccaggacacc    240

gcgcccagtg acgatgggac ctcgagcagt ctggacggga gtgtctttgc cgccgacgga    300

actccgaccg ctccgggggc gttggccagg acgcgccgct cgcagacctc ggaatcgatc    360

acctccagca acttcaacta cagtttgaac cggaggttca tctccaagaa ccagatgaaa    420

gagttccggg aggcgttccg gctgtttgac aaggacaacg acgggtcgat cacgaaggag    480

gagctgggca cggtgatgcg atcactgggg cagtttgccc gtgtcgagga actgcaggag    540

atgctgctgg agattgacgt cgatggtgat ggcaacgtca gcttcgagga gtttgtcgac    600

atcatgtcca acatgaccga cacggtggcg gaggcatccg ccgaccagga ggagcgcgaa    660

ctccgggatg cgttccgcgt gtttgacaag cacaaccggg gctacatcac ggcgtctgat    720

ctgcgggcgg ttctgcagtg tctgggagaa gatttggacg aggaagaaat cgaagacatg    780

atcaaggagg tggacgtcga cggcgatgga cggatcgact tttacgagtt tgtgcacgcc    840

ctcggagagc cggaagattc acaggagaac gacgacgagg aggacccccct gtcacctccg    900

tcactgtcgt gtgacgtaaa cgcctaa                                        927


<210> SEQ ID NO 54
<211> LENGTH: 300
<212> TYPE: RNA
<213> ORGANISM: Culex quinquefasciatus

<400> SEQUENCE: 54

gaguuccggg aggcguuccg gcuguuugac aaggacaacg acgggucgau cacgaaggag     60

gagcugggca cggugaugcg aucacugggg caguuugccc gugucgagga acugcaggag    120

augcugcugg agauugacgu cgauggugau ggcaacguca gcuucgagga guuugucgac    180

aucaugucca acaugaccga cacgguggcg gaggcauccg ccgaccagga ggagcgcgaa    240
```

cuccgggaug cguuccgcgu guuugacaag cacaaccggg gcuacaucac ggcgucugau 300

<210> SEQ ID NO 55
<211> LENGTH: 333
<212> TYPE: DNA
<213> ORGANISM: Culex quinquefasciatus

<400> SEQUENCE: 55
atggtcggtg tccaagctgg ccatttgata tctcaatcac ggcggggcgg ctccgcgtgc 60
gaaaacgggg aaattttgat tgatgacggc ggcggcgggg agcggcgggt tttaaacctg 120
ttctacaagg ggaataaaaa tgccgatcaa cttacagagg aacagatcgc cgagttcaaa 180
gaagcgttct cgctgttcga caaagacggt gacggcacga tcacgaccaa ggagctgggc 240
accgtgatgc gatcgttagg ccagaacccc acagaagcag agctgcaaga catgataaac 300
gaggtcgatg cggacggact gcatccgctt taa 333

<210> SEQ ID NO 56
<211> LENGTH: 300
<212> TYPE: RNA
<213> ORGANISM: Culex quinquefasciatus

<400> SEQUENCE: 56
gucggugucc aagcuggcca uuugauaucu caaucacggc ggggcggcuc cgcgugcgaa 60
aacggggaaa uuuugauuga ugacggcggc ggcggggagc ggcggguuuu aaaccuguuc 120
uacaagggga auaaaaaugc cgaucaacuu acagaggaac agaucgccga guucaaagaa 180
gcguucucgc uguucgacaa agacggugac ggcacgauca cgaccaagga gcugggcacc 240
gugaugcgau cguuaggcca gaaccccaca gaagcagagc ugcaagacau gauaaacgag 300

<210> SEQ ID NO 57
<211> LENGTH: 934
<212> TYPE: DNA
<213> ORGANISM: Acyrthosiphon pisum

<400> SEQUENCE: 57
gctgtgcacg ttttgtttac ccgaaaaatg tgattcaaac tttcagtttt ttaaatctta 60
actgcgttgt ttaagaaaaa aaaaaaccta aatttattat tgtttattaa taataaatca 120
atcgatcgaa taatcgtttg cgggtatacc taagtacgaa gtaaaatatg agtgcacaaa 180
atagtgataa tgaccgttat aaaaaggaat attcgagaat aaggaaactg acgagtagat 240
atgacatacg gactcaatca aatgaatttg gtttgtcgga agatcaagtt gcggaattca 300
aagaagcatt tatgttgttc gataaagacc atgatggacg gattactgag gcagaactag 360
gagtggtcat gagatctttg ggtcaaaggc ctactgaaac tgatttgcga ggtatggtta 420
aagaagtgga taaagatggc aatggtagta ttgagtttga tgaattcctg ctaatgatgg 480
ctagaaaact aaaagcagca gatggcgagg aagaaatgca ccaagctttt aaagtatttg 540
acaaaaatgg cgatggattc ataacatttg atgaactcaa acgtgttatg tgcagtatcg 600
gagaaaggct cactgatgaa gaaattgagg acatgataaa agaagcagat ttaaatggtg 660
ataaaaaaat tgattataaa gaatttatta caataataag ttctaagaaa taaaacgaat 720
tacggacttg gatgtaccct catatggcat tcgttcctca tctgcatctg tgtcattggc 780
tgctaagact ttacttaata ataaaccttg atcttctcta ctagaataaa atagctctgg 840
atcctaaagt aaaatataca gtataatttt aaaatagtcg tatacaaatt ttttttaaa 900 tattgagtgt acctcatcca ttccagcaag tttc 934

<210> SEQ ID NO 58
<211> LENGTH: 372
<212> TYPE: RNA
<213> ORGANISM: Acyrthosiphon pisum

<400> SEQUENCE: 58
ucaaguugcg gaauucaaag aagcauuuau guuguucgau aaagaccaug auggacggau 60
uacugaggca gaacuaggag uggucaugag aucuuugggu caaaggccua cugaaacuga 120
uuugcgaggu augguuaaag aaguggauaa agauggcaau gguaguauug aguuugauga 180
auuccugcua augauggcua gaaaacuaaa agcagcagau ggcgaggaag aaaugcacca 240
agcuuuuaaa guauuugaca aaaauggcga uggauucaua acauuugaug aacucaaacg 300
uguuaugugc aguaucggag aaaggcucac ugaugaagaa auugaggaca ugauaaaaga 360
agcagauuua aa 372

<210> SEQ ID NO 59
<211> LENGTH: 2509
<212> TYPE: DNA
<213> ORGANISM: Acyrthosiphon pisum

<400> SEQUENCE: 59
gatttttcgt ttaaataacc cccccgggtt tcggataaac tcggtgtgcg tgtggacgcc 60
gccgccgccg cgtgagcgtt atttcgctcg ctgtgattac gaacgctcgt gcagtcgtcg 120
tcatgcagca tctccgagac ccggcgaaag accatcagag tacgtgaaca ctgcacatca 180
cactccatcg cgatatactt atctgtagga cgacaccctt taccgaggac acaatgatat 240
acacgttata atactatcgt acatcgtata tattgtattc ttatcatcta atattatatt 300
atcacaatcg ttatattgta ttatagaatt attgtatatc gttttaattt gacacgatac 360
gacatttggt gttgagaatc gcgcagagag agaaagagag agagaaaaag agagaataga 420
tattttgatg taaataatta ttacaatata atattgtatt tgaaaataga aacagataat 480
tggtcgttga ggcagttctc accttttttaa gatatacata ttatattata tataaacagt 540
attttgtttt actcctttga gtgaacattt cgtttaacta taccacaatt tattaatatt 600
atataatatc tatcatggac ggtaaaatat catcggtatt cgaaaaatac ttttcacctt 660
caccgctggt gaaccaaata aggaattttg tcaatcggca aatagacgag caaacgccac 720
aaaacgtaag cacacaacca accgctgtag cgaaacttca cagtaataat gtagtgaacg 780
gcaccactcc gaaacccatc acaagcaacg aaaaaccaac ggaagtccaa gtacatccac 840
aacccactca gcctgccgat agaaacttag tgcacgttac taaagcacag atgaaagaat 900
ttcaagaagc atttaggtta tttgataaag acggtgacgg cagcatcact aaagaggaat 960
tgggtcgagt tatgcggagt cttggacagt ttgctagaga agaagaattg gagacaatgt 1020
tacaagaagt cgacatcgat ggcgatggag cgttcagttt tcaagagttt gtagaaattg 1080
tgtacaatat gggtggtaca gcagaaaaga cggcggacca agaggaaaaa gagctccgag 1140
acgcatttag ggtatttgac aaacataacc gaggatatat aagtgcgtcg gacttgagag 1200
ctgtccttca atgtttgggt gaagatttgt cagaagaaga aatcgaggat atgatcaagg 1260
aagtagacgt ggacggagat ggaagaatcg atttttacga atttgtgaat gcccttggag 1320
aaccaggaga tgattatgat gaaaacgacg aagatgaaga agatatttat ccccaattgg 1380
acattcaaac ataacttata aacaattaca cgttttagta tgatgcgata acaagttcag 1440

```
ttaaaattga attatcaaaa atgataacaa tattttttgt aaacttaggt taaaatgtta   1500

aaaacttacc cattttgtaa tttctatcag gaataaacac accaatatct gttttttttt   1560

tgccaactaa tgatctctaa taagtaaaac atattttact ttaatatcaa tgtactactg   1620

tagtattgtt aagtaattta tgtcattttc aatgtttaat gtataaatta atcatttaat   1680

ggtacaatca gtaattcacc ttaagaccca attatttatt aaaaacatat tatatcatta   1740

atttacttaa tgtatacatt ttagtcaaaa aacattcagt tatatgttat aagtcgttat   1800

aactatttat ttaagaaact ataaaaaatt attatttatt ataatagttt acgtatctat   1860

ttacttccat ggaaggtatt tataaataga aaatgttaag gtaacttaat taaaacaata   1920

attatgaaca agtattttta ctttaaaaaa attacataat tatattgtca gtattctttc   1980

aaatacaatt aattcaaatt tgtgaaattg tccattcctc ctttatgctt tgtgaactaa   2040

atttaaatac attaagaacc agagtacaat taaaggaaat agtcagctgc gtgttttttt   2100

gttggcattc ctcggttttc ttgtggtgct gcctcaaata ttgtaaaatc tctttgaagt   2160

gtttcactga gttccaatat tgccgcaacg ttaccacatc tattatttac aattagtatt   2220

aacaattaaa taacagcatt aataaataaa tagtataatg taatttttag agtagtattt   2280

accgataaca atagttgggt gctgaccaaa cagtaagcac ggtttcatca aaatgccatt   2340

tatatccttc catgactagt tgatgagctc gacaaataat atctatatca tttgtagtat   2400

taaactggga gacaacatca gaaccaaata ggtatccagc accccgagga ctcacacccc   2460

atccctgagt atctaaaata attgtgtatg ttaaaaatct attttttt              2509
```

<210> SEQ ID NO 60
<211> LENGTH: 294
<212> TYPE: RNA
<213> ORGANISM: Acyrthosiphon pisum

<400> SEQUENCE: 60

```
acagaugaaa gaauuucaag aagcauuuag guuauuugau aaagacggug acggcagcau     60

cacuaaagag gaauugggucgaguuaugcg gagucuugga caguuugcua gagaagaaga    120

auuggagaca auguuacaag aagucgacau cgauggcgau ggagcguuca guuuucaaga    180

guuuguagaa auuguguaca auaugggugg uacagcagaa aagacggcgg accaagagga    240

aaaagagcuc cgagacgcau uuaggguauu ugacaaacau aaccgaggau auau         294
```

<210> SEQ ID NO 61
<211> LENGTH: 477
<212> TYPE: DNA
<213> ORGANISM: Pediculus humanus

<400> SEQUENCE: 61

```
atggccgacg aaacgacgac ggaattaccg gaggaaaatc tttcggttga aaaaatcgca     60

gaattccgcg aagctttcaa ccttttcgac aaagatggcg acggtaacat aacgaccaaa    120

gaattgggta cttgcatgag gtctctcggg cagaatccga cggaagcgga aatcgcggag    180

ctgatttgcg aagtagacgt agagggaaca ggtttaatcg atttcacatc gttcgttttg    240

ataatggcta aaaagataaa agacgtcgac aacgaggaag aactcagaga agcttttaga    300

atattcgata aggaaggtaa cggattcata accgcatccg agctcaggca cataatgatg    360

aacttgggtg aaaaattaac ggaagaagaa tgcgacgaaa tgattaggga agcggatgtc    420

atgggtgacg gaaatatcaa ttacgaagaa ttcgtcacca tgatgatgtc aaagtga      477
```

<210> SEQ ID NO 62
<211> LENGTH: 379
<212> TYPE: RNA
<213> ORGANISM: Pediculus humanus

<400> SEQUENCE: 62

```
aaaaaucgca gaauuccgcg aagcuuucaa ccuuuucgac aaagauggcg acgguaacau     60

aacgaccaaa gaauugggua cuugcaugag gucucucggg cagaauccga cggaagcgga    120

aaucgcggag cugauuugcg aaguagacgu agagggaaca gguuuaaucg auuucacauc    180

guucguuuug auaauggcua aaaagauaaa agacgucgac aacgaggaag aacucagaga    240

agcuuuuaga auauucgaua aggaagguaa cggauucaua accgcauccg agcucaggca    300

cauaaugaug aacuugggug aaaaauuaac ggaagaagaa ugcgacgaaa ugauuaggga    360

agcggauguc augggugac                                                 379
```

<210> SEQ ID NO 63
<211> LENGTH: 537
<212> TYPE: DNA
<213> ORGANISM: Pediculus humanus

<400> SEQUENCE: 63

```
atggatgcta ggaatgaagt ttacaacacc gaatataatc gtttaagaaa attgacgtgt     60

agaacggaaa ttaaattatc ttgctctgaa tatggtctta cggaggaaca agtcgctgaa    120

tttaaagaag cttttatgct ttttgacaaa gatgaagatg gacaaataac aatggccgaa    180

ttaggagtcg ttatgagatc tttgggacaa cgtccgacag aaacggaatt aagagacatg    240

gttaaagagg ttgatcaaga tggaaatggt acaatcgaat tcaatgaatt tttacaaatg    300

atggcaaaaa aaatgaaagg agctgatggt gaagaagaac ttcgagaagc attcagggtg    360

tttgataaaa ataacgatgg actcatttca tccattgaac ttcgacatgt catgacaaat    420

ttaggtgaga aactttcaga cgaagaagtt gatgatatga taaaagaagc agatttagat    480

ggagatggta tggttaacta caatgaattt gtaacgatat taacatcaaa aaattaa       537
```

<210> SEQ ID NO 64
<211> LENGTH: 417
<212> TYPE: RNA
<213> ORGANISM: Pediculus humanus

<400> SEQUENCE: 64

```
acaagucgcu gaauuuaaag aagcuuuuau gcuuuuugac aaagaugaag auggacaaau     60

aacaauggcc gaauuaggag ucguuaugag aucuuuggga caacguccga cagaaacgga    120

auuaagagac augguuaaag agguugauca agauggaaau gguacaaucg aauucaauga    180

auuuuuacaa augauggcaa aaaaaaugaa aggagcugau ggugaagaag aacuucgaga    240

agcauucagg guguuugaua aaaauaacga uggacucauu ucauccauug aacuucgaca    300

ugucaugaca aauuuaggug agaaacuuuc agacgaagaa guugaugaua ugauaaaaga    360

agcagauuua gauggagaug guaugguuaa cuacaaugaa uuuguaacga uauuaac       417
```

<210> SEQ ID NO 65
<211> LENGTH: 648
<212> TYPE: DNA
<213> ORGANISM: Pediculus humanus

<400> SEQUENCE: 65

```
atgactacga aacataatat atctggaaga atacgggacg aaccaggggg acaaagggaa     60
```

```
aaaaatggaa atgtaaccgg tcgaacaata acatatccaa caacagggaa caaaagaaat    120

attgatacaa tgacgaaaaa taacatatca aaatcgcaaa tgaaggaatt tcgagaagct    180

tttcgacttt ttgacaaaga tggtgatggt agtataactc aagaagaact tggaagagtt    240

atgagatctt taggacaatt tgccagagaa gaagaactac aagaaatgct taaggaagtt    300

gatatagatg gagatggaaa ttttagcttt gaagaatttg ttgaaatcgt atcaaatatg    360

ggaggtgcag caactgaaaa aacagctgat gaagaagaga aagaacttag agatgctttt    420

agagtatttg ataaacataa tcgaggtttt ataagtgctt ctgatcttcg agctgttttg    480

caatgtctgg gtgaagaatt atcagaagaa gaaaaaatga taagagaagt tgatgtggat    540

ggagatggta gaattgattt tttcgaattt gttcgagctt tgggtacaca ctacaggcaa    600

aatttctttt tcaggtttct atccatttat attattagca cagtttga                648
```

<210> SEQ ID NO 66
<211> LENGTH: 449
<212> TYPE: RNA
<213> ORGANISM: Pediculus humanus

<400> SEQUENCE: 66

```
aucgcaaaug aaggaauuuc gagaagcuuu ucgacuuuuu gacaaagaug gugaugguag     60

uauaacucaa gaagaacuug gaagaguuau gagaucuuua ggacaauuug ccagagaaga    120

agaacuacaa gaaaugcuua aggaaguuga uauagaugga gauggaaauu uuagcuuuga    180

agaauuuguu gaaaucguau caaauauggg aggugcagca acugaaaaaa cagcugauga    240

agaagagaaa gaacuuagag augcuuuuag aguauuugau aaacauaauc gagguuuuau    300

aagugcuucu gaucuucgag cuguuuugca augucugggu gaagaauuau cagaagaaga    360

aaaaaugaua agagaaguug auguggaugg agaugguaga auugauuuuu ucgaauuugu    420

ucgagcuuug gguacacacu acaggcaaa                                      449
```

<210> SEQ ID NO 67
<211> LENGTH: 648
<212> TYPE: DNA
<213> ORGANISM: Pediculus humanus

<400> SEQUENCE: 67

```
atgatgaaaa acaaaactga cagcagtctc ggagctgagc attcagattt gaaacattcg     60

acgagtgaaa ccgaagaact ccaatcctcg gaactcgaag tgataaaaga tgaagagcct    120

caaatagatc tgagacagtt tctgacgaaa gaacaagtgc aagaattcaa aagaattttc    180

caggcttacg atgtcaacaa cgaagataaa atcccggtca aagccatcgg aatcattttg    240

agaaacatgg gattgaatcc gtccaaggcg attctcaaga gaatgacaaa ggaaatcgat    300

ccggataaaa acggttacgt ggatttcgaa atgtttttac atcccatggc acgaatgata    360

cacgaagtcc cggaaaatca cgaggacata atcgcagcat tcaaagtttt cgacgaagac    420

gacgaaggtt tcgtatccgt taaagctttg accgaatacc tcacgaacct gggcgaagat    480

ttggaagatt tcgaaattga taatttgatt aaaatggcgg atcccaaagg cacgggccga    540

gtctactacg aaggattcgt cgagaaaatt ttcggaatcg taagaaacgg gaaaaaaaag    600

aaaaatctca aagggaaaaa gggaaaaaaa cgaaaaaaaa atgaatga                648
```

<210> SEQ ID NO 68
<211> LENGTH: 451
<212> TYPE: RNA

<213> ORGANISM: Pediculus humanus

<400> SEQUENCE: 68

```
ucaaauagau cugagacagu uucugacgaa agaacaagug caagaauuca aaagaauuuu     60
ccaggcuuac gaugucaaca acgaagauaa aaucccgguc aaagccaucg gaaucauuuu    120
gagaaacaug ggauugaauc cguccaaggc gauucucaag agaaugacaa aggaaaucga    180
uccggauaaa aacgguuacg uggauuucga aauguuuuua caucccaugg cacgaaugau    240
acacgaaguc ccggaaaauc acgaggacau aaucgcagca uucaaaguuu ucgacgaaga    300
cgacgaaggu uucguauccg uuaaagcuuu gaccgaauac cucacgaacc ugggcgaaga    360
uuuggaagau uucgaaauug auaauuugau uaaaauggcg gaucccaaag gcacgggccg    420
agucuacuac gaaggauucg ucgagaaaau u                                   451
```

<210> SEQ ID NO 69
<211> LENGTH: 1546
<212> TYPE: RNA
<213> ORGANISM: Varroa destructor

<400> SEQUENCE: 69

```
guuuagccca uuuucgcgcu gugucugucg gcgacugcgg aaguacugag cuagcugagu     60
cgugguggcuu agaaggcagu ggcagugagu ggcaucagcg guaauaagug agggacaaca    120
gccggagagu cgugucgguu gguaggucgg uucguugccg auuaaugccc cacaugugag    180
uuacgugcgg ugcuuguucc gcugugcauu ggacguuaca uacagagagu cagguguagu    240
uuauuuuaga cgaaaaacua ccagcacuac cugauacagc gacccaacgu agagagggaa    300
agagaaagag cuguuguuuc gcuagguuag uucugaacaa uuggauugau ucgcaaaugu    360
acgcuuguac ggcuaacggu ugaacggacu gugcaaacug cggauagugc gugaacuagc    420
agacaacaua uccaauaacu aacuacacgg uuauuauuga uacaaacacc uaguucagac    480
agacaauuuc gguuugcuuu guuggcacua uaaggaguaa gugauauugu uuuuuguuua    540
ucagucggcc uaguauuguc ggugcacuua cggauaacag gagaggcagu acaaaggcaa    600
cucgauucac uaucguucac gggcgcuaau acagcgaaau auuaauaggc aaagcaagca    660
agccagccgg ccaagcccaa accccgggcg aaacgcagau accaacagcg cugaagugcg    720
uggcaaacga caacgggaca guagggcaua agcuagacag cauauagcuu uucuaaccau    780
ggcugaucag cuaacugagg aacagaucgc cgaguucaaa gaggcguuua gccuguuuga    840
caaggacgga gauggcacga ucacgacaaa ggagcucggu acgguaaugc gaucucucgg    900
ccagaacccc acugaggcug aacugcagga caugaucaac gaggucgacg ccgacggcuc    960
cggaacgaua gauuucccug aguuccucac aaugauggca agaaagauga aggacaccga   1020
cucggaggag gagauccgag aggcguuccg cguauucgac aaggauggca acgguuucau   1080
uucggcggcc gagcucaggc acguuaugac caaccuuggc gagaagcuua cggacgagga   1140
gguagaugag augauucggg aggcagauau ugacggugau ggucagguca acuacgagga   1200
guucgucacc augaugacgu ccaaguaaau auaugauaau guuggcuguc ucguguaaug   1260
ucgugagaaa gaaagcgcgc gcgaaagaaa gagagaaagg aauagaaaac uauaaauagc   1320
uuguuguuaa agcaacgcaa caacaagcug uaagcaacaa acaauauuua cgaaguauac   1380
gauaaugaaa gucgacaggg aagcaagcac ggauauauau gaaaacuaag cgaaaugacg   1440
ucgucaucau caccagcagc agcagcagca gcagcagcag cagcagcagc accaccacca   1500
ccaccaucac gaccaccacc accaccacca ccaucacgac caccac                  1546
```

<210> SEQ ID NO 70
<211> LENGTH: 1136
<212> TYPE: RNA
<213> ORGANISM: Varroa destructor

<400> SEQUENCE: 70
guucggcucg gggacuagcu gaucggucgg uguguauugu uggcuauugg caaagaccgu 60
uguugagugg gcucgcugca cugagcguuu aaaucuggug aaaucguugg caauggcgga 120
ucagcugacc gaggagcaaa ucgccgaauu caaggaggcu uucagccugu ucgauaaaga 180
cggugauggc acaauuacga ccaaggaacu agggaccguc augcgguccc ucggccagaa 240
cccuacugag gcugagcuuc aagacaugau caacgagguc gacgcugacg guaacggcac 300
uauugacuuu ccagaguuuc ucacgaugau ggcgcguaaa augaaggaca ccgacuccga 360
ggaggagauc cgggaagcuu uuaggguuuu ugauaaagac ggaaauggcu ucauuucggc 420
ugcagagcug aggcacguaa ugaccaaccu uggcgaaaag cucacggacg aggaagugga 480
cgagaugauc cgcgaggcgg auaucgacgg cgacggacag gucaacuacg aggaguucgu 540
cacgaugaug acaucaaaau gaagggcuca cuauugcgcg ggaaaagcag cccaacaaag 600
aaaccuagag ugcgaaagcg agaacguuaa acacgaugau augcuaauga uaauacauac 660
gacuagagga cagaaagaca gacagacaga cugagcagac gaacgggcaa guugaagaaa 720
agccgaguug aacuggcuaa ccguugggua cucauucaua uucgauaguu acagacaaca 780
acaugaaaaa cgacagcaac aauccgcaac aaacacacgg agauugcaca caaugagggu 840
aaacugaaca uggugcagcg gaaguuggau ggcagcggua cacagugcug cuacugcugc 900
ugcugcaaau gcuaacacuc aauaaugaua auaauaauua uaauuauaga aauaugauua 960
uguuguccaa aagagaaaca aacaacacaa acaaagcuau uaaaaaucug aauaaaagcu 1020
aagaagaaau caaguagcag ucgacauggg gaguggcaaa cgauaagagu ccacagaaaa 1080
cugaagcggc cgaaagaaaa cacgaggcaa aaggcaaugu auucauuaag acgagg 1136

<210> SEQ ID NO 71
<211> LENGTH: 150
<212> TYPE: RNA
<213> ORGANISM: Artificial Sequence
<220> FEATURE:
<223> OTHER INFORMATION: Synthetic Sequence

<400> SEQUENCE: 71
guuuagccca uuuucgcgcu gugucugucg gcgacugcgg aaguacugag cuagcugagu 60
cguggugcuu agaaggcagu ggcagugagu ggcaucagcg guaauaagug agggacaaca 120
gccggagagu cgugucgguu gguaggucgg 150

<210> SEQ ID NO 72
<211> LENGTH: 150
<212> TYPE: RNA
<213> ORGANISM: Artificial Sequence
<220> FEATURE:
<223> OTHER INFORMATION: Synthetic Sequence

<400> SEQUENCE: 72
uucguugccg auuaaugccc cacaugugag uuacgugcgg ugcuuguucc gcugugcauu 60
ggacguuaca uacagagagu cagguguagu uuauuuuaga cgaaaaacua ccagcacuac 120
cugauacagc gacccaacgu agagagggaa 150

<210> SEQ ID NO 73
<211> LENGTH: 150
<212> TYPE: RNA
<213> ORGANISM: Artificial Sequence
<220> FEATURE:
<223> OTHER INFORMATION: synthetic sequence

<400> SEQUENCE: 73
agagaaagag cuguuguuuc gcuagguuag uucugaacaa uuggauugau ucgcaaaugu 60
acgcuuguac ggcuaacggu ugaacggacu gugcaaacug cggauagugc gugaacuagc 120
agacaacaua uccaauaacu aacuacacgg 150

<210> SEQ ID NO 74
<211> LENGTH: 150
<212> TYPE: RNA
<213> ORGANISM: Artificial Sequence
<220> FEATURE:
<223> OTHER INFORMATION: synthetic sequence

<400> SEQUENCE: 74
uuauuauuga uacaaacacc uaguucagac agacaauuuc gguuugcuuu guuggcacua 60
uaaggaguaa gugauauugu uuuuuguuua ucagucggcc uaguauuguc ggugcacuua 120
cggauaacag gagaggcagu acaaaggcaa 150

<210> SEQ ID NO 75
<211> LENGTH: 150
<212> TYPE: RNA
<213> ORGANISM: Artificial Sequence
<220> FEATURE:
<223> OTHER INFORMATION: synthetic sequence

<400> SEQUENCE: 75
cucgauucac uaucguucac gggcgcuaau acagcgaaau auuaauaggc aaagcaagca 60
agccagccgg ccaagcccaa accccgggcg aaacgcagau accaacagcg cugaagugcg 120
uggcaaacga caacgggaca guagggcaua 150

<210> SEQ ID NO 76
<211> LENGTH: 150
<212> TYPE: RNA
<213> ORGANISM: Artificial Sequence
<220> FEATURE:
<223> OTHER INFORMATION: synthetic sequence

<400> SEQUENCE: 76
agcuagacag cauauagcuu uucuaaccau ggcugaucag cuaacugagg aacagaucgc 60
cgaguucaaa gaggcguuua gccuguuuga caaggacgga gauggcacga ucacgacaaa 120
ggagcucggu acgguaaugc gaucucucgg 150

<210> SEQ ID NO 77
<211> LENGTH: 150
<212> TYPE: RNA
<213> ORGANISM: Artificial Sequence
<220> FEATURE:
<223> OTHER INFORMATION: synthetic sequence

<400> SEQUENCE: 77
ccagaacccc acugaggcug aacugcagga caugaucaac gaggucgacg ccgacggcuc 60
cggaacgaua gauuucccug aguuccucac aaugauggca agaaagauga aggacaccga 120
cucggaggag gagauccgag aggcguuccg 150

-continued

<210> SEQ ID NO 78
<211> LENGTH: 150
<212> TYPE: RNA
<213> ORGANISM: Artificial Sequence
<220> FEATURE:
<223> OTHER INFORMATION: synthetic sequence

<400> SEQUENCE: 78
cguauucgac aaggauggca acgguuucau uucggcggcc gagcucaggc acguuaugac 60
caaccuuggc gagaagcuua cggacgagga gguagaugag augauucggg aggcagauau 120
ugacggugau ggucagguca acuacgagga 150

<210> SEQ ID NO 79
<211> LENGTH: 150
<212> TYPE: RNA
<213> ORGANISM: Artificial Sequence
<220> FEATURE:
<223> OTHER INFORMATION: synthetic sequence

<400> SEQUENCE: 79
guucgucacc augaugacgu ccaaguaaau auaugauaau guuggcuguc ucguguaaug 60
ucgugagaaa gaaagcgcgc gcgaaagaaa gagagaaagg aauagaaaac uauaaauagc 120
uuguuguuaa agcaacgcaa caacaagcug 150

<210> SEQ ID NO 80
<211> LENGTH: 150
<212> TYPE: RNA
<213> ORGANISM: Artificial Sequence
<220> FEATURE:
<223> OTHER INFORMATION: synthetic sequence

<400> SEQUENCE: 80
uaagcaacaa acaauauuua cgaaguauac gauaaugaaa gucgacaggg aagcaagcac 60
ggauauauau gaaaacuaag cgaaaugacg ucgucaucau caccagcagc agcagcagca 120
gcagcagcag cagcagcagc accaccacca 150

<210> SEQ ID NO 81
<211> LENGTH: 150
<212> TYPE: RNA
<213> ORGANISM: Artificial Sequence
<220> FEATURE:
<223> OTHER INFORMATION: synthetic sequence

<400> SEQUENCE: 81
guucggcucg gggacuagcu gaucggucgg uguguauugu uggcuauugg caaagaccgu 60
uguugagugg gcucgcugca cugagcguuu aaaucuggug aaaucguugg caauggcgga 120
ucagcugacc gaggagcaaa ucgccgaauu 150

<210> SEQ ID NO 82
<211> LENGTH: 150
<212> TYPE: RNA
<213> ORGANISM: Artificial Sequence
<220> FEATURE:
<223> OTHER INFORMATION: synthetic sequence

<400> SEQUENCE: 82
caaggaggcu uucagccugu ucgauaaaga cggugauggc acaauuacga ccaaggaacu 60
agggaccguc augcgguccc ucggccagaa cccuacugag gcugagcuuc aagacaugau 120
caacgagguc gacgcugacg guaacggcac 150

<210> SEQ ID NO 83
<211> LENGTH: 150
<212> TYPE: RNA
<213> ORGANISM: Artificial Sequence
<220> FEATURE:
<223> OTHER INFORMATION: synthetic sequence

<400> SEQUENCE: 83
uauugacuuu ccagaguuuc ucacgaugau ggcgcguaaa augaaggaca ccgacuccga 60
ggaggagauc cgggaagcuu uuaggguuuu ugauaaagac ggaaauggcu ucauuucggc 120
ugcagagcug aggcacguaa ugaccaaccu 150

<210> SEQ ID NO 84
<211> LENGTH: 150
<212> TYPE: RNA
<213> ORGANISM: Artificial Sequence
<220> FEATURE:
<223> OTHER INFORMATION: synthetic sequence

<400> SEQUENCE: 84
uggcgaaaag cucacggacg aggaagugga cgagaugauc cgcgaggcgg auaucgacgg 60
cgacggacag gucaacuacg aggaguucgu cacgaugaug acaucaaaau gaagggcuca 120
cuauugcgcg ggaaaagcag cccaacaaag 150

<210> SEQ ID NO 85
<211> LENGTH: 150
<212> TYPE: RNA
<213> ORGANISM: Artificial Sequence
<220> FEATURE:
<223> OTHER INFORMATION: synthetic sequence

<400> SEQUENCE: 85
aaaccuagag ugcgaaagcg agaacguuaa acacgaugau augcuaauga uaauacauac 60
gacuagagga cagaaagaca gacagacaga cugagcagac gaacgggcaa guugaagaaa 120
agccgaguug aacuggcuaa ccguugggua 150

<210> SEQ ID NO 86
<211> LENGTH: 150
<212> TYPE: RNA
<213> ORGANISM: Artificial Sequence
<220> FEATURE:
<223> OTHER INFORMATION: synthetic sequence

<400> SEQUENCE: 86
cucauucaua uucgauaguu acagacaaca acaugaaaaa cgacagcaac aauccgcaac 60
aaacacacgg agauugcaca caaugagggu aaacugaaca uggugcagcg gaaguuggau 120
ggcagcggua cacagugcug cuacugcugc 150

<210> SEQ ID NO 87
<211> LENGTH: 150
<212> TYPE: RNA
<213> ORGANISM: Artificial Sequence
<220> FEATURE:
<223> OTHER INFORMATION: synthetic sequence

<400> SEQUENCE: 87
ugcugcaaau gcuaacacuc aauaaugaua auaauaauua uaauuauaga aauaugauua 60
uguuguccaa aagagaaaca aacaacacaa acaaagcuau uaaaaaucug aauaaaagcu 120

```
aagaagaaau caaguagcag ucgacauggg                              150


<210> SEQ ID NO 88
<211> LENGTH: 156
<212> TYPE: RNA
<213> ORGANISM: Artificial Sequence
<220> FEATURE:
<223> OTHER INFORMATION: synthetic sequence

<400> SEQUENCE: 88

ggcaacgguu ucauuucggc ggccgagcuc aggcacguua ugaccaaccu uggcgagaag     60

cuuacggacg aggagguaga ugagaugauu cgggaggcag auauugacgg ugauggucag    120

gucaacuacg aggaguucgu caccaugaug acgucc                              156


<210> SEQ ID NO 89
<211> LENGTH: 257
<212> TYPE: RNA
<213> ORGANISM: Artificial Sequence
<220> FEATURE:
<223> OTHER INFORMATION: synthetic sequence

<400> SEQUENCE: 89

ggcggaucag cugaccgagg agcaaaucgc cgaauucaag gaggcuuuca gccuguucga     60

uaaagacggu gauggcacaa uuacgaccaa ggaacuaggg accgucaugc ggucccucgg    120

ccagaacccu acugaggcug agcuucaaga caugaucaac gaggucgacg cugacgguaa    180

cggcacuauu gacuuuccag aguuucucac gaugauggcg cguaaaauga aggacaccga    240

cuccgaggag gagaucc                                                   257
```